US007071158B2

(12) United States Patent
Chinery et al.

(10) Patent No.: US 7,071,158 B2
(45) Date of Patent: Jul. 4, 2006

(54) ANTIOXIDANT ENHANCEMENT OF THERAPY FOR HYPERPROLIFERATIVE CONDITIONS

(75) Inventors: Rebecca Chinery, Nashville, TN (US); R. Daniel Beauchamp, Nashville, TN (US); Robert J. Coffey, Woodside, CA (US); Russell M. Medford, Atlanta, GA (US); Brian E. Wadzinski, Nashville, TN (US)

(73) Assignee: Atherogenics, Inc., Norcross, GA (US)

( * ) Notice: Subject to any disclaimer, the term of this patent is extended or adjusted under 35 U.S.C. 154(b) by 558 days.

(21) Appl. No.: 09/779,086

(22) Filed: Feb. 7, 2001

(65) Prior Publication Data
US 2001/0049349 A1 Dec. 6, 2001

Related U.S. Application Data

(63) Continuation of application No. 09/108,609, filed on Jul. 1, 1998, now abandoned, which is a continuation of application No. 08/967,492, filed on Nov. 11, 1997, now abandoned, which is a continuation-in-part of application No. 08/886,653, filed on Jul. 1, 1997, now abandoned.

(51) Int. Cl.
*A61K 31/00* (2006.01)
*A61K 31/50* (2006.01)

(52) U.S. Cl. .......................... 514/1; 514/34; 514/183; 514/185; 514/284; 514/492

(58) Field of Classification Search .................. 514/1, 514/2, 548, 712, 34, 183, 185, 284, 492; 435/7.1
See application file for complete search history.

(56) References Cited

U.S. PATENT DOCUMENTS

| | | | |
|---|---|---|---|
| 3,479,407 A | 11/1969 | Laufer | |
| 3,576,883 A | 4/1971 | Neuworth | |
| 4,029,812 A | 6/1977 | Wagner et al. | |
| 4,076,841 A | 2/1978 | Wagner et al. | |
| 4,078,084 A | 3/1978 | Wagner et al. | |
| 4,752,616 A | 6/1988 | Hall et al. | |
| 4,954,514 A | 9/1990 | Kita et al. | |
| 5,035,878 A | 7/1991 | Borch | |
| 5,155,250 A | 10/1992 | Parker | |
| 5,206,247 A | 4/1993 | Regnier et al. | |
| 5,215,892 A | 6/1993 | Kishimoto et al. | |
| 5,262,409 A | 11/1993 | Margolis et al. | |
| 5,262,439 A | 11/1993 | Parthasarathy | |
| 5,294,430 A | 3/1994 | Borch | |
| 5,348,963 A | 9/1994 | Gandy et al. | |
| 5,360,894 A | 11/1994 | Kishimoto et al. | |
| 5,380,747 A | 1/1995 | Medford et al. | |
| 5,545,563 A | 8/1996 | Darlington et al. | |
| 5,608,095 A | 3/1997 | Parker et al. | |
| 5,627,205 A | 5/1997 | Regnier et al. | |
| 5,674,492 A | 10/1997 | Armitage et al. | |
| 5,750,351 A | 5/1998 | Medford et al. | |
| 5,773,209 A | 6/1998 | Medford et al. | |
| 5,773,231 A | 6/1998 | Medford et al. | |
| 5,783,596 A | 7/1998 | Medford et al. | |
| 5,792,787 A | 8/1998 | Medford et al. | |
| 5,807,884 A | 9/1998 | Medford et al. | |
| 5,811,449 A | 9/1998 | Medford et al. | |
| 5,821,260 A | 10/1998 | Medford et al. | |
| 5,846,959 A | 12/1998 | Medford et al. | |
| 5,877,203 A | 3/1999 | Medford et al. | |
| 6,121,319 A | 9/2000 | Somers | |
| 6,147,250 A | 11/2000 | Somers | |
| 6,448,019 B1 | 9/2002 | Mendelsohn et al. | |
| 6,548,699 B1 | 4/2003 | Somers | |
| 6,602,914 B1 | 8/2003 | Meng | |

FOREIGN PATENT DOCUMENTS

| | | |
|---|---|---|
| DE | DT 27 16125 A1 | 10/1977 |
| EP | 0292660 A2 | 11/1988 |
| EP | 0418648 B1 | 3/1991 |
| EP | 0348203 A1 | 2/1993 |
| EP | 0621255 A1 | 10/1994 |
| EP | 0405788 A2 | 1/1995 |
| EP | 0763527 B1 | 4/2000 |
| FR | 2168137 | 1/1972 |
| FR | 2130975 | 11/1972 |
| FR | 2133024 | 11/1972 |
| FR | 2134810 | 12/1972 |
| FR | 2140769 | 1/1973 |
| FR | 2140771 | 1/1973 |
| GB | L 136539 | 12/1968 |
| GB | L 199871 | 7/1970 |

(Continued)

OTHER PUBLICATIONS

Cheng et al. Cancer Letters (Shannon Ireland) (1990) vol. 51(3) pp. 213-220.*
American Heritage Dictionary of the English Language 4th Ed. (2000) definitin of "therapeutic index".*
Ripoll et al. J. Urology (1986) vol. 136(2) pp. 529-531.*
Yasunaga et al. Archiv Fuer Japnishe Chirurgie (1983) vol. 52(5) pp. 591-601.*

(Continued)

*Primary Examiner*—Bennett Celsa
(74) *Attorney, Agent, or Firm*—Sherry M. Knowles, Esq.; King & Spalding LLP

(57) ABSTRACT

A method to enhance the cytotoxic activity of an antineoplastic drug comprising administering an effective amount of the antineoplastic drug to a host exhibiting abnormal cell proliferation in combination with an effective cytotoxicity-increasing amount of an antioxidant. The invention also includes a method to decrease the toxicity to an antineoplastic agent or increase the therapeutic index of an antineoplastic agent administered for the treatment of a solid growth of abnormally proliferating cells, comprising administering an antioxidant prior to, with, or following the antineoplastic treatment.

14 Claims, 28 Drawing Sheets

FOREIGN PATENT DOCUMENTS

| | | |
|---|---|---|
| JP | 7-328425 | 12/1995 |
| JP | 8040888 A | 2/1996 |
| WO | WO 93/20691 | 10/1993 |
| WO | WO 93/20691 A1 | 10/1993 |
| WO | WO 94/20113 A1 | 9/1994 |
| WO | WO 95/09365 | 4/1995 |
| WO | WO 95/09365 A1 | 4/1995 |
| WO | WO 95/15760 | 6/1995 |
| WO | WO 95/15760 A1 | 6/1995 |
| WO | WO 95/26719 | 10/1995 |
| WO | WO 95/26719 A1 | 10/1995 |
| WO | WO 95/30415 A1 | 11/1995 |
| WO | WO 96/16989 A1 | 6/1996 |
| WO | WO 97/15546 A1 | 5/1997 |
| WO | WO 98/51289 A2 | 11/1998 |
| WO | WO 98/51289 A3 | 11/1998 |
| WO | WO 98/51662 A2 | 11/1998 |
| WO | WO 98/51662 A3 | 11/1998 |

OTHER PUBLICATIONS

Szczepanska et al. Eur. J. Haematology (1988) vol. 40(1) pp. 69-74.*
Siveski-Iliskovic et al. Circulation vol. 91, Issue 1 (Jan. 1995) pp. 10-15.*
Weijl et al. Cancer Treatment Reviews (Jul. 1997) vol. 23(4) pp. 209-240.*
Cloos et al. Carcinogenesis (1996) vol. 17(2) pp. 327-331.*
Chinery et al. Nature Medicine vol. 3, No. 11 (Nov. 1997) pp. 1233-1241.*
Biosis AN: 1990:428349 Abstract to Archives of Toxicology (1990) vol. 64, No. 5 pp. 393-400.*
Embase AN 9227964 Abstract to Anticancer Research (1992) vol. 12 (3) pp. 599-606.*
Coffey, et al., *Cancer Res.* 47, 4590 (1987).
Crook, et al. *Oncogene* 6, 873 (1991).
Scheffner, et al. *Proc. Natl. Acad. Sci. U.S.A.* 88, 5523 (1991).
Ripoll, et al., Vitimin E Enhances the Chemotherapeutic Effects of Adriamycin, *Biological Abstracts*, 82, 82084938.
Yaunaga et al., Vitimin E and Cancer Therapy-Experimental Study in Mice, Database National Cancer Institute, 1982.
Szczepanska et al., Inhibition of Leukocyte Migration by Cancer Chemotherapeutic Agents and its Prevention by Free Radical Scavengers and Thiols, Biological Abstracts vol. 85, 85106445.
Prasad et al., Vitamin E Increases the Growth Inhibitoryuy and Differenciating Effects of Tumor Therapeutic Agents on Neuro Blastoma and Glioma Cells in Culture, Biological Abstracts, vol. 70, 70052454.
Drago, et al., Chemptherapy and Vitamin E in Treatment of NB Rat Prostrate Tumors, Biological Abstracts vol. 88, 88006807.
Cloos Jacqueline Jan, Influence of the antioxidant N-acetylcysteine annd its metabolites on Damage induced by Bleomycin in PM2 Bacteriophage, *Biological Abstracts*, vol. 96, 98730849.
Riordan et al., Case study: High Dose Intravenous Vitamin C in the Treatment of a Patient with Adenocarcinoma of the Kidney, *J. Orthomolecular Med.*, 5:1, 1990, 5-7.
Campbell et al., Retticulum Cell Sarcoma: Two Complete "Spontaneous" Regressions, in Response to High-Dose Ascorbic Acid Therapy, *Oncology*, 48:6 (1991), 495-497.
Bongers, Antioxidant-Related Parameters in Patients Treated for Cancer Chemoprevention with N-acetylcysteine, *Biological Abstracts*, vol. 95, 98363146.
Offerman, etal. AntooxidantSensitive Regulation of Inflammatory_Response Genes in Kaposi's Sarcoma Cells, *J. of AIDS and Hum. Retro.*, (1996) 13:1-11.
Tyagi S C, Reduction-Oxidation state Regulation of Extracellular Matrix Metalloproteinases and Tissue Inhibitors in Cardiac Normal and Transformed Fibroblast Cells, *Biological Abstracts*, vol. 96, 98730849.
Roesl, Differential Regulation of the JE Gene Encoding the Monocyte Chemoattractant Protein (MCP-1) in Cervical Carcinoma Cells and Derived Hybrids, *Biological Abstracts*, vol. 94, 97193049.
Kowens-Leutz, et al., Novel Mechanism of C/EPBbeta (NF-M) Transciptional Control: Activation Through Derepression, *Genes and Development*, 8:1994, 2781-2791.
Favre et al., The catalytic Subunit of protein Phophatase 2A is Carboxyl-methylated in vivo. *J. of Biol. Chem.*, 269:23, (1994), 16311-16317.
Trautwien et al., Protein Kinase A and C Site-Specific Phosphorylations of LAP (nf-IL6) Modulate its Binding Affinity to DNA Recognition Elements, *J. of Clin. Investig.*, 93:6, (1994) 2554-2561.
WPI Derwent Publications Ltd., 97-373441 1995.
WPI Derwent Publications Ltd., 96-157002 1996.
Chinery, R. et al. *Antioxidant-induced Nuclear Translocation of CCAAT/Enhancer-binding Protein beta* Journal of Biological Chemistry 272: 30356-30361 (1997).
Chinery, R. et al. *Antioxidant-induced Nuclear Translocation of CCAAT/Enhancer-binding Protein beta* Journal of Biological Chemistry 272: 30356-30361 (1997).
Berkowitz et al. Tet. Lett. vol. 35, pp. 6445-6448 (Jul. 1994).
Mahoney et al., J. Biol. Chem. vol. 267, No. 27 pp. 19396-19403 (Jul. 1994).
Abstract to Hedricks-Taylor et al. Genomics, vol. 14(1) pp. 12-17 (Jan. 1992).
Advanced Cancer Meta-Analysis Project (P. Piedbois, et al.), "Modulation of fluorouracil by leucovorin in patients with advanced colorectal cancer: evidence in terms of response rate", *J. Clin. Oncol.*, 10(6):896-903 (Jun. 1992).
Akira, S., et al., "A nuclear factor for IL-6 expression (NF-IL6) is a member of a C/EBP family", *EMBO J.*, 9(6):1897-1906 (1990).
Akira, S., et al., "IL-6 and NF-IL6 in acute phase response to viral infection", *Immunol. Rev.*, 127:25-50 (1992).
Anderson, T.J., et al., "The effect of cholesterol-lowering and antioxidant therapy on endothelium-dependent coronary vasomotion", *N. Eng. J. Med.*, 332(8):488-493 (1995).
Anonymous, "AtheroGenics announces positive Phase II results from CART-1 clinical trial for restenosis: study analyses suggest AGI-1067 directly affects coronary artery disease", *Atherogenics, Inc., Press Release*, (2001).
Barnhart, J.W., et al., Chapter 10: The Synthesis, metabolism, and biological activity of probucol and its analogs, 277-299 XP002095165.
Baron, J.L., et al., "The pathogensis of adoptive murine autoimmune diabetes requires an interaction between $\alpha$-4-integrins and vascular cell adhesion molecule-1", *J. Clin. Invest.* 93:1700-1708 (Apr. 1994).
Berkowitz, D.B., et al., "Synthesis of the ($\alpha,\alpha$-difluoroalkyl)phosphonate analogue of phosphoserine", *Tet. Lett.*, 35(35):6445-6448 (Jul. 1994).
Bowry, V.W., et al., "Vitamin E in human low-density lipoprotein: when and how this antioxidant becomes a pro-oxidant", *Biochem. J.* 288:341-344 (1992).
Brown, et al., "Lipoprotein metabolism in the macrophage: implications for cholesterol deposition in antherosclerosis", *Ann. Rev. Biochem.*, 52:223-261 (1983).

Burkly, L.C., et al., "Protection against adoptive transfer of autoimmune diabetes mediated through very late antigen-4 integrin", *Diabetes,* 43:529-534 (Apr. 1994).

Campbell, A. et al., "Reticulum cell sarcoma: two complete "spontaneous" regressions, in response to high-dose ascorbic acid therapy", *Oncology,* 48(6):495-497 (1991). XP002074537.

Cao, et al., "Regulated expression of three C/EBP isoforms during adipose conversion of 3T3-L1 cells", *Genes & Dev.,* 5:1538-1552 (1991).

Carew, et al., "Antiatherogenic effect of probucol unrelated to its hypocholesterolemic effect: Evidence that antioxidants *in vivo* can selectively inhibit low density lipoprotein degradation in macrophage-rich fatty streaks and slow the progression of atherosclerosis in the Watanabe heritable hyperlipidemic rabbit", *Proc. Natl. Acad. Sci. U.S.A.,* 84:7725-7729 (Nov. 1987).

Chang, et al., "Molecular cloning of a transcription factor, AGP/EBP, that belongs to members of the C/EBP family", *Mol. Cell. Biol.,* 10(12):6642-6653 (Dec. 1990).

Chinery, R., et al., "Antioxidant-induced nuclear translocation of CCAAT/enhancer-binding protein beta. A critical role for protein kinase A-mediated phosphorylation of Ser$^{299}$", *J. Biol. Chem.,* 272(48):30356-30361 (Nov. 28, 1997). Erratum: *J. Biol. Chem.,* 273:15308 (1998).

Chinery, R., et al., "Antioxidants enhance the cytotoxicity of chemotherapeutic agents in colorectal cancer: a p53-independent induction of p21$^{WAF1/CIP1}$ via C/EPBβ", *Nat. Med.,* 3(11):1233-1241 (Nov. 1997).

Coffey, R.J., Jr., et al., "Transforming growth factor α and β expression in human colon cancer lines: Implications for an autocrine model", *Cancer Res.* 47:4590-4594 (Sep. 1, 1987).

Cohen, B., et al., "Prognosis of node-positive colon cancer", *Cancer* (Phila.), 67:1859-1861 (1991).

Cominacini, L., et al., "Antioxidants inhibit the expression of intercellular cell adhesion molecule-1 and vascular cell adhstion molecule 1 induced by oxidized LDL on human umbilical vein endothelial cells", *Free Radical Biol. Adhesion Med.* 22(1/2):117-127 (1997). XP002095164.

Crook, et al., "p53 Point mutation in HPV neative human cervical carcinoma cell lines", *Oncogene,* 6:873-875 (1991).

DeMeglio, P., et al., "Nuovl derivati del clopibrato e del probucol. Studio preliminare dell'attivita ipolipemizzante", *Farmaco, Ed. Sci.,* 40(11):833-844 (1985) (in Italian); "New derivatives of clofibrate and probucol. Preliminary studies on hypolipemic activity" *Chem. Abstracts* 104:28675 XP-002124424.

El-Deiry, W., et al., "WAF1, a potential mediator of p53 tumor suppresion", *Cell.* 75:817-825 (Nov. 19, 1993).

Fariss, M.W., et al., "The selective antiproliferative effects of α-tocopheryl hemisuccinate and cholesteryl hemisuccinate on murine leukemia cells result from the action of the intact compounds", Cancer Res., 54(13):3346-3351 (Jul. 1, 1994).

Faure, H., et al., "5-Hydroxymethyluracil excretion, plasma TBARS and plasma antioxidant vitamins in Adriamycin-treated patients", *Free Radical Biol. & Med.,* 20(7):979-983 (1996).

Favre, B., et al., "The catalytic subunit of protein phosphatase 2A is carboxyl-methylated in vivo", *J. of Biol. Chem.,* 269(23):16311-16317 (1994). XP002090665.

Fearon, E.R., et al., "Progressing toward a molecular description of colorectal cancer development", *FASEB J.,* 6:2783-2790 (Jul. 1992).

Folkman, J., et al., "Angiogenesis", *J. Biol. Chem.,* 267(16):10931-10934 (Jun. 5, 1992).

Fruebis, J.A., et al., "A comparison of the antiatherogenic effects of probucol and of a structural analogue of probucol in low density lipoprotein receptor-deficient rabbits", *J. Clinical Investigation, Inc.,* 94:392-398 (Jul. 1994).

Geetha, A., et al., "Levels of serum antioxidants in doxorubicin-treated rats - influence of vitamins E and C", Curr. Sci., 58(19):1100-1102 (Oct. 5, 1989). Chem. Abstr. 112:69504 (1990).

Gershbein, L.L., et al., "Action of drugs and chemical agents on rat liver regeneration", *Drug and Chemical Toxicology,* 8(3) 125-143 (1985).

Guo, H.B, et al., "Clinical significance of serum S100 in metastatic malignant melanoma", *Eur. J. Cancer,* 31A(6):924-928 (1995).

Haas, A.L., et al., "Vitamin E inhibits proliferation of human Tenon's capsule fibroblasts in vitro", *Ophthalmic Res.,* 28(3):171-175 (1996). *Chem. Abstr.* 125:158572 (1996).

Hacker, M.P., et al., "Effect of disulfiram (tetraethylthiuram disulfide) and diethyldithiocarbanate on the bladder toxicity and antitumor activity of cyclophosphamide in mice", *Cancer Res.,* 42(11):4490-4494 (Nov. 1982).

Heeg, et al., "Plasma levels of Probucol in man after single and repeated oral doses", *La Nouvelle Presse Medicale,* 9(40):2990-2994 (Oct. 30, 1980). Abstract in English.

Hendricks-Taylor, L.R., et al., "The CCAAT/Enhancer Binding Protein (C/EBPα) gene (CEBPA) maps to human chromosome 19q13.1 and the related nuclear factor NF-IL6 (C/EBPβ) gene (CEBPB) maps to human chromosome 20q13.1", *Genomics,* 14(1):12-17 (Jan. 1992).

Iademarco, M.F., et al., "Characterization of the promoter for vascular cell adhesion molecule-1 (VCAM-1)", *J. Biol. Chem.* 267(23):16323-16329 (Aug. 15, 1992).

Kapiloff, M.S., et al., "Variable effects of phosphorylation of Pit-1 dictated by the DNA response elements", *Science,* 253:786-789 (Aug. 16, 1991).

Khine, M.B.B.S., et al., "High frequency of allelic deletion on chromosome 17p in advanced colorectal cancer", *Cancer* (Phila.), 73(1):28-35 (Jan. 1, 1994).

Koch, A.E., et al., "Immunolocalization of endothelial and leukocyte adhesion molecules in human rheumatoid and osteoarthritic synovial tissues", *Lab. Invest.,* 64(3):313-320 (1991).

Kovach, J.S., et al., "Mutation detection by highly sensitive methods indicates the p53 gene mutations in breat cancer can have important prognostic value", *Proc. Natl. Acad. Sci. U.S.A.,* 93:1093-1096 (Feb. 1996).

Kowens-Leutz, B., et al., "Novel mechanism of C/EPBbeta (NF-M) transcriptional control: activation through depression", *Genes and Development,* 8:2781-2791 (1984). XP002090664.

Kunsch, C., et al., "Oxidative stress as a regulator of gene expression in the vasculature", *Circ. Res.* 85:753-766 (1999).

Kuzuya, M., et al., "Probucol prevents oxidative injury to endothelial cells", *J. Lipid Res.,* 32:197-204 (1991).

Landschulz, et al., "Isolation of a recombinant copy of the gene encoding C/EBP gene", *Genes & Dev.,* 2:786-800 (1998).

Lankin, V.A., et al., "Antiradical and antioxidative properties of probucol and its structural analog during oxidation of unsaturated phospholipids in natural and artificial membranes", *Chemical Abstracts,* 127(6):75973u (1996). [Original: Dold. Adad. Nauk, 351(4):554-557 (1996) [in Russian]].

Li, L., et al., Inst. Medicinal Biological Techn. China, "New water soluble dan phenolic acid A for treating cancer", CN 1,110,139 A; Oct. 18, 1995; Abstract, WPI Derwent Publications Ltd., 97-373441 (1995). XP002080080.

Mahoney, C.W., et al., "Phosphorylation of CCAAT-enhancer binding protein by protein kinase C attenuates site-selective DNA binding", *J. Biol. Chem.*, 267(27):19396-19403 (Sept. 25, 1992).

Mao, et al., "Antioxidant activity of Probucol an its analogues in hypercholsterolemic Watanabe rabbits", *J. Med. Chem.*, 34(18) 298-302 (1991).

Mao, et al., "Attenuation of atherosclerosis in a modified strain of hypercholsterolemic Watanabe rabbits with use of a Probucol analogue (MDL#29,311) that does not lower serum cholesterol", *Arteriosclerosis and Thrombosis*, 11(5):1266-1275 (Sep./Oct. 1991).

Martin-Jimenez, M., et a., "Failure of high dose tocopherol to prevent alopecia induced by doxorubicin", *N. England J. Medicine* (USA), 315(14):894-895 (Oct. 02, 1986). Chem. Abstr. 86:3386.

Medvedev, A. I., et al., "Synthesis and properties of some new derivatives of 3,5-di-tert-butyl-4-hydroxythiophenol", *Chemical Abstracts*, 86:5066m (1977). [Original at *Tizisy Dokl. Nauchn. Sess. Khim. Tekhnol. Org. Soedin. Sery Semistykh Neftel*, 13th, 23-4 (1974) [in Russian]].

Meng et al., "Novel phenolic antioxidants as multifunctional inhibitors of inducible VCAM-1 expression for use in atherosclerosis," *Bioorg. & Med. Chem. Lett.* 12:2545-2548 (2002).

Miller, G.J., "High density lipoproteins and atherosclerosis", *Ann. Rev. Med.*, 31:97-108 (1980).

Morales-Ducret, J., et al., "α4/β1 Integrin (VLA-4) ligands in arthritis: vascular cell adhesion molecule-1 expression in synovium and on fibroblast-like synoviocytes", *J. Immunol.*, 149(4):1424-1431 (Aug. 15, 1992).

Neuworth, M.B., et al., "Synthesis and hypocholesterolemic activity of alkylidenedithio bishenols", *J. Med. Chem.*, 13(4):722-725 (1970). XP-002124423.

Oberley, L.W., et al., "Antitumor therapies based on inhibition of antioxidant enzymes", Oxy Radicals Their Scavenger Syst., Proc. Int. Conf. Superoxide Superoxide Dismutase, 3rd (1983), Meeting Date 1982, vol. 2:242-254. Editor(s): Cohen, G., and Greenwald, R.A. Publisher: Elsevier, New York, NY, Chem. Abstr. 100:326 (1984).

Offerman, M.K., et al., "Antioxidant sensitive regulation of inflammatory response genes in Kaposi's sarcoma cells", *J. of AIDS and Hum. Retro.*, 13(1):1-11 (1986). XP002089729.

Ohkawara, Y., et al., "*In situ* expression of the cell adhesion molecules in bronchial tissues from asthmatics with air flow limitation: *in vivo* evidence of VCAM-1/VLA-4 interaction in selective eosinophil infiltration", *Am. J. Respir. Cell. Mol. Biol.*, 12:4-12 (1995).

Orosz, C.G., et al., "Role of the endothelial adhesionmolecule VCAM in murine cardiac allograft rejection", *Immunol. Lett.*, 32:7-12 (1992).

Parthasarathy, S., et al., "Probucol inhibits oxidative modification of low density lipoprotein", *J. Clin. Invest.*, 77:641-644 (1986).

Patton, J.G., et al., "Monoclonal antibodies to human plasma low density lipoproteins. II. Evaluation for use in radioimmunoassay for apolipoprotein B in patients with coronary artery disease",*Clin. Chem.*, 29(11):1898-1903 (1983).

Pilewski, J.M., et al., "Cell adhesion molecules in asthma: homing, activation, and airway remodeling", *J. Respir. Cell. Mol. Biol.*, 12:1-3 (1995).

Poli, V., et al., "IL-6DBP, a nuclear protein involved in interleukin-6 signal transduction, defines a new family of leucine zipper proteins related to C/EBP", *Cell*, 63:643-653 (Nov. 2, 1990).

Prasad, K.N., et al., "Vitamin E increases the growth inhibitory and differentiating effects of tumor therapeutic agents on neuroblastoma and glioma cells in culture 40840", *Proceedings of the Society for Experimental Biology and Medicine*, 164(2):158-163 (1980); Biological Abstracts, 70:70052454. XP00208077.

Pritchard, D.M., et al., "Apoptosis and gastrointestinal pharmacology", *Pharmacol. Ther.*, 72(12):149-169 (1996).

Rabb, H.A., et al., "The role of the leukocyte adhesion molecules VLA-4, LFA-1 and Mac-1 in allergic airway responses in the rat", *Am. J. Respir. Crit. Care Med.*, 149:1186-1191 (1994).

Ramasamy, S., et al., "Modulation of expression of endothelial nitric oxide synthase by nordihydrogualaretic acid, a phenolic antioxidant in cultured endothelial cells", *Molecular Pharmacology*, 56:116-123 (1999); available online at http://ww.molpham.org.

Righetti, S.C., et al., "A comparative study of p53 gene mutations, protein accumulation, and response to cisplatin-based chemotherapy in advanced ovarian carcinoma", *Cancer Res.*, 56:689-693 (Feb. 15, 1996).

Rinninger, et al., "Probucol enhances selective uptake of HDL-associated cholesteryl esters in vitro by a scavenger receptor B-1-dependent mechanism", *Atherioschler. Throm. Vasc. Biol.*, 19:1325-1332 (1999). XP-008001008.

Riordan, H.D., et al., "Case study: high dose intravenous Vitamin C in the treatment of a patient with adenocarcinoma of the kidney", *J. Orthomolecular Med.*, 5(1) 5-7 (1990). XP002074538.

Ripoll, E.A.P., et al., "Vitamin E enhances the chemotherapeutic effects of Adriamycin on human prostatic carcinoma cells in vitro", *J. Urol.*, 136(2):529-531 (1986). Biological Abstracts, 82:82084938. XP002080075.

Roberts, C.P., et al., "Regulation of monocyte to macrophage differentiation by antiglucocorticoids and antioxidants", *Am. J. Obstet. Gynecol.*, 179(2):354-362 (1998).

Rösl, F., et al., "Differential regulation of the JE gene encoding the monocyte chemoattractant protein (MCP-1) in cervical carcinoma cells and derived hybrids", *J. Virology*, 68(4):2142-2150 (1994) *Biological Abstracts* 94:97193049. XP002089733.

Ryden, T.A., et al., "Avian retroviral long terminal repeats bind CCAAT/Enhancer-Binding Protein", *Mol. Cell. Biol.*, 9(3):1155-1164 (1989).

Sawayama, Y., et al., "Effects of Probucol and Pravastatin on common carotid atherosclerosis in patients with asymptomatic hypercholesterolemia", *Journal of the American College of Cardiology*, 39(4):610-616 (2002).

Scheffner, M., et al., "The state of the p53 and retinoblastoma genes in human cervical carcinoma cell lines", *Proc. Natl. Acad. Sci. U.S.A.*, 88:5523-5527 (1991).

Singh, S.V., et al., "Cytochrome P450 reductase, antioxidant enzymes and cellular resistance to doxorubicin", *Biochem. Pharmacol.*, 40(2):385-387 (1990). Chem. Abstr. 113:108901 (1990).

Steinberg, D., et al., "Modifications of low-density lipoprotein that increase its atherogenicity", *N. Eng. J. Med.*, 220(14):915-924 (1989).

Subramanian, S., et al., "Oxidant and antioxidant levels in the erythrocytes of breast cancer patients treated with CMF", Med. Sci. Res., 21(2):79-80 (1993). Chem. Abstr. 118:161022 (1993).

Szczepanska, I., et al., "Inhibition of leucocyte migration by cancer chemotherapeutic agents and its preventions by free radical scavengers and thiols", Eur. J. Haematology, 40(1):69-74 (1988); Biological Abstracts 85:85106445. XP002080076.

Tardif, J.C., et al., "Antioxidants and restenosis: human studies", in Tardif, J.C., et al., eds., Antioxidants and Cardiovascular Disease, Boston, Mass.: Kluwer Academic Publishers (2000):175-191.

Tardif, J.C., et al., "Effects of AGI-1067 and Probucol after percutaneous coronary Interventions", Circulation, 107(4):552-558 (2003).

Trautwein, C., et al., "Protein kinase A and C site-specific phosphorylations of LAP (nf-IL6) modulate its binding affinity to DNA recognition elements", J. of Clin. Investig., 93(6):2554-2561 (1994). XP002090666.

Tyagi, S.C., et al., "Reduction-oxidation (redox) state regulation of extracellular matrix metalloproteinases and tissue inhibitors in cardiac normal and transformed fibroblast cells", J. Cellular Biology, 61(1):139-151 (1996): abstract from Biological Abstracts, 96:98730849. XP002089732.

Weitzman, S.A. et al., "Prospective study of tocopherol prophylaxis for anthracycline cardiac toxicity", Curr. Ther. Res. CI, 28(5):682-686 (Nov. 1980). Chem. Abstr. 80:3993.

Whittaker, J.A., et al., "Effect of digoxin and vitamin E in preventing cardiac damage caused by doxorubicin in acute myeloid leukemia", British Medical Journal (England), 288:283-284 (Jan. 28, 1994). Chem. Abstr. 84:2926.

Williams, et al., "A family of C/EBP-related proteins capable of forming covalently linked leucine zipper dimers in vitro", Genes & Development, 5:1553-1567 (1991).

Yang, X.-D., et al., "Inhibition of insulitis and prevention of diabetes in nonobese diabetic mice by blocking L-selection and very late antigen 4 adhesion receptors", Proc. Natl. Acad. Sci. U.S.A., 90:10494-10498 (1993).

\* cited by examiner

Figure 1E

Sensitization of HCT 116 and HCT 15 colon cancer cells to chemotherapeutic agents by PDTC (70 µM) or vitamin E (3 mM)

| Cell line | Drug | IC$_{50}$ (µM)[a] | | |
|---|---|---|---|---|
| | | − Antioxidant | +PDTC | +vitamin E |
| HCT 116 | 5FU | 3.8 (±0.21) | 1.5 (±0.29) | 1.7 (±0.20) |
| | Doxorubicin | 0.32 (±0.07) | 0.09 (±0.08) | 0.13 (±0.05) |
| HCT 15 | 5FU | 11.4 (±0.11) | 1.01 (±0.09) | 1.4 (±0.10) |
| | Doxorubicin | 1.51 (±0.07) | 0.11 (±0.05) | 0.17 (±0.04) |

[a]The concentration of 5-FU or doxorubicin required to reduce soft agar colony formation by 50% (±s.e.m.). Underscored: significantly different from -antioxidant group ($P<0.01$), as determined by analysis of variance with multiple comparison adjustment.

Figure 3A Western blot
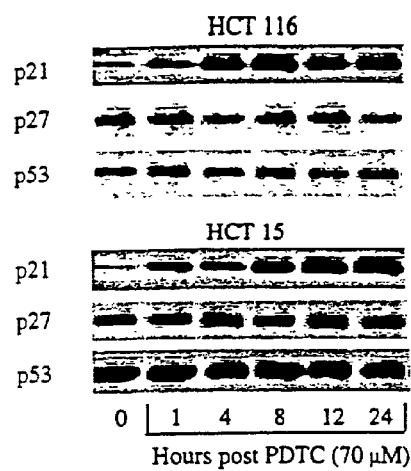
Figure 3B Northern blot
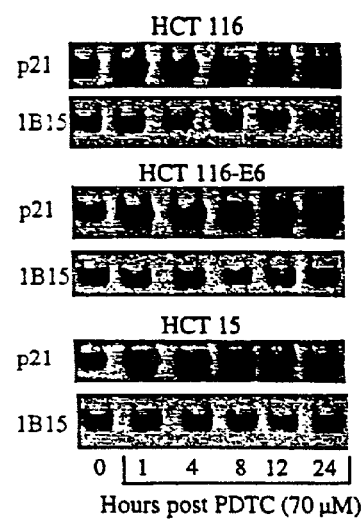
Figure 3C
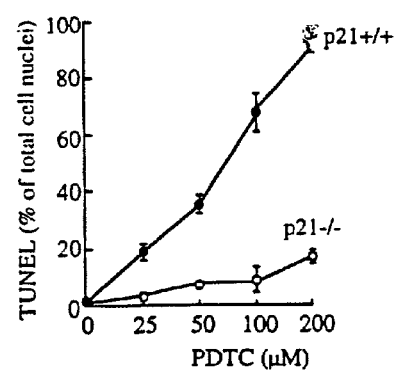
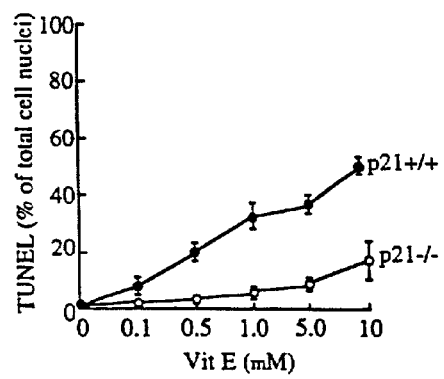

Figure 9B  Trypsin cleavage

| Control | PDTC | PDTC + mPKI |

Carboxylmethylation of PP2Ac is Inhibited by
Antioxidants

Antioxidants Inhibit Methyltransferase Activity Against PP2Ac

PDTC Inhibits PP2A, but not PP1, Activity ppt proteins with TCA

Count radioactivity left on C/EBPβ

- Control
- I2 (PP1)
- Okadaic acid (PP1 and PP2)
- PDTC
- I2+PDTC
- Okadaic acid+PDTC

SEQUENCE LISTING

```
<160> NUMBER OF SEQ ID NOS: 6

<210> SEQ ID NO 1
<211> LENGTH: 4
<212> TYPE: PRT
<213> ORGANISM: Homo sapiens
<220> FEATURE:
<221> NAME/KEY: UNSURE
<222> LOCATION: (1)..(4)
<223> OTHER INFORMATION: Xaa = any amino acid.
<221> NAME/KEY: UNSURE
<222> LOCATION: (1)..(4)
<223> OTHER INFORMATION: This sequence is the protein kinase A consensus
      phosphorylation site.

<400> SEQUENCE: 1

Arg Xaa Ser Xaa
  1

<210> SEQ ID NO 2
<211> LENGTH: 5
<212> TYPE: PRT
<213> ORGANISM: Homo sapiens
<220> FEATURE:
<221> NAME/KEY: UNSURE
<222> LOCATION: (1)..(5)
<223> OTHER INFORMATION: Xaa = any amino acid residue with flanking Xaa
      also corresponding to flanking peptide sequences
      with substantial homology to C/EBPbeta.

<400> SEQUENCE: 2

Xaa Arg Xaa Ser Xaa
  1               5

<210> SEQ ID NO 3
<211> LENGTH: 20
<212> TYPE: DNA
<213> ORGANISM: Homo sapiens

<400> SEQUENCE: 3
gtacttaaga aatattgaat                                              20

<210> SEQ ID NO 4
<211> LENGTH: 20
<212> TYPE: DNA
<213> ORGANISM: Homo sapiens

<400> SEQUENCE: 4
attcaatatt tcttaagtac                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: mutant
      sequence

<400> SEQUENCE: 5
gtacaaaaga aatattgaat                                              20
```

```
<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: mutant
      sequence

<400> SEQUENCE: 6
atcaatattt cttttgtac                                               19
```

ANTIOXIDANT ENHANCEMENT OF THERAPY FOR HYPERPROLIFERATIVE CONDITIONS

This application is a continuation application of U.S. Ser. No. 09/108,609 filed on Jul. 1, 1998 now abandoned, which is a continuation application of U.S. Ser. No. 08/967,492, entitled "Antioxidant Enhancement of Anti-Neoplastic Therapy for Hyperproliferative Conditions," filed on Nov. 11, 1997 now abandoned, by Rebecca Chinery, R. Daniel Beauchamp, Robert J. Coffey, Russell M. Medford and Brian Wadsinski, and converted to a provisional application by a petition filed on Jun. 30, 1998; which is a continuation-in-part application of U.S. Ser. No. 08/886,653, entitled "Antioxidant Enhancement of Anti-Neoplastic Therapy," filed on Jul. 1, 1997 now abandoned, by Rebecca Chinery, R. Daniel Beauchamp, and Robert J. Coffey, and converted to a provisional application by a petition filed on Jun. 20, 1998.

This invention was developed in part using funds from the federal government under National Institute of Health grant Nos. CA4613 and GM53319 and CA-69457. The United States government, therefore, has certain rights in this invention.

FIELD OF THE INVENTION

This invention is in the field of medicinal chemistry, and more specifically, the methods and compositions for antioxidant enhancement of therapy for hyperproliferative conditions.

BACKGROUND OF THE INVENTION

A wide range of disorders involves the hyperproliferation of cells, ranging from psoriasis to benign and malignant tumors. These disorders are generally caused by a loss of control over normal cell growth, differentiation, or the process of programmed cell death (apoptosis). Many of the abnormalities that underlie these disorders, particularly cancer, occur at the genetic level. Antineoplastic agents (also known as cytotoxic agents) are often used in the treatment of hyperproliferative conditions. Therapy with antineoplastic agents is successful in the treatment of a number of malignant conditions; however, in most it is used to palliate the symptoms and to prolong life in patients with advanced disease. Two groups of drugs used in the treatment of hyperproliferative conditions are antimetabolites and alkylating agents. Antimetabolites can be subdivided into folic acid, purine and pyrimidine derivatives. In addition, several natural products, or their derivatives, have been used as mitotic inhibitors. These include vinca alkaloids, and the derivatives of podophyllotoxin. There remains an effort in the research community to understand the genetic basis for abnormal cell hyperproliferation, which can vary among its various manifestations, and to develop therapeutic methods to successfully treat these serious conditions.

For about four decades, the antimetabolite 5-fluorouracil (5-FU), and nucleosides that include this base (e.g., 5-fluoro-2'-deoxyuridine or FdUrd), have remained among the few "standard" drugs effective against solid tumors in man. 5-Fluorouracil is used mainly for the treatment of colorectal, ovarian, renal, breast and head and neck cancers. 5-Fluoro-2'-deoxyuridine is used for the treatment of solid tumors, including hepatic metastases of advanced gastrointestinal adenocarcinomas, renal cell carcinomas, advanced ovarian cancer, and squamous cell carcinomas of the head and neck. The clinical utility of the fluoropyrimidines is limited by the host-toxicity induced by the administration of these compounds. Manifestations of the host-toxicity of the fluoropyrimidines include mainly gastrointestinal epithelial ulceration, myelosuppression and, to a lesser extent, cardiotoxicities, hepatotoxicities and neurotoxicities.

A population of cancer patients is intolerant to treatment with 5-fluorouracil and 5-fluoro-2'-deoxyuridine. The intolerance to 5-fluorouracil was initially attributed to a deficiency or low activity of dihydrouracil dehydrogenase (DHUDase, EC 1.3.1.2), the first enzyme in the catabolic pathway of 5-fluorouracil. However, it appeared that not all intolerant patients showed reduced dihydrouracil dehydrogenase activities. Moreover, it has also been shown that cancers, treated with fluoropyrimidines, become resistant, i.e., develop tolerance towards these drugs.

Colorectal cancer (CRC) is a multi-step process resulting from the accumulation of mutations in clonal populations of colonocytes. Mutations of the p53 tumor suppressor gene are a relatively late, yet common event in the pathogenesis of colorectal cancer, occurring in over 80% of late adenomas and carcinomas (Fearon, et al., FASEB J. 6, 2789 (1992); Srivastarva, et al., Contemp. Oncol. April 63 (192); Kline, et al., Cancer (Phila. 73, 28 (1994). Conventional therapy for advanced disease, such as cytotoxic chemotherapy and gamma-irradiation, induce DNA damage in proliferating cells. This damage, through undefined mechanism(s), signals the induction of p53, which, in turn, leads to inhibition of cellular proliferation by induction of $G_1$ cell cycle arrest and, in some instances, apoptosis. Thus, tumors lacking functional p53 are frequently refractory to such therapies (S. C. Righetti et al., Cancer Res. 56, 689 (1996); J. S. Kovack et al., Proc. Natl. Acad, Sci. U.S.A. 93, 1093 (1996)), emphasizing the importance of developing treatments for advanced colorectal cancer that do not rely on functional p53.

The most effective single chemotherapeutic agent for advanced colorectal cancer to date remains 5-FU. The active metabolite of 5-FU, 5-fluorodeoxyuridine-5'-monophosphate (FdUMP), forms a complex with thymidylate synthase (TS) in the presence of reduced folate, thereby inhibiting enzyme activity, and depleting precursors for DNA synthesis. 5-FU is also incorporated into RNA, altering its processing and function, although how this correlates with cytotoxicity is unknown. Previous data suggest that 5-FU can utilize both p53-dependent and independent pathways (Pritchard, et al., Pharmacol Ther. 72, 149 (1996)), although a loss of p53 function dramatically reduces 5-FU efficacy (B. Cohen et al., Cancer (Phila.) 67, 1859 (1991); Advanced Cancer Meta-Analysis Project, J. Clin. Oncol. 10, 896 (1992)).

In view of the lack of successful treatments for many hyperproliferative conditions, it would be of benefit both to identify important biological pathways that mediate the loss of normal cell function, including programmed cell death (i.e., apoptosis), and to identify compositions and methods for the treatment of these disorders.

U.S. Pat. Nos. 5,035,878 and 5,294,430 disclose that dithiocarbamates can reverse the damage to the blood-forming function of the bone marrow (myelosuppression) caused by treatment with antineoplastic agents.

It is therefore an object of the invention to provide a method and composition for the treatment of abnormal cell proliferative conditions, including benign and malignant tumors.

It is another object of the present invention to provide a method and composition for the treatment of colon cancer.

It is a further object of the present invention to provide a method and composition for the treatment of solid tumors.

It is yet another object of the present invention to provide a method and composition for the treatment of diffuse tumors.

SUMMARY OF THE INVENTION

It has been discovered that antioxidants, including those specifically disclosed herein, induce cell cycle arrest (G1, G2, S and M type), and thus are useful to enhance the efficacy of antineoplastic drugs for the treatment of abnormal cell proliferation. In one embodiment, therefore, the invention is a method to enhance the cytotoxic activity of an antineoplastic drug comprising administering an effective amount of the antineoplastic drug to a host exhibiting abnormal cell proliferation in combination with an effective cytotoxicity-increasing amount of an antioxidant.

It has further been discovered that antioxidants not only induce cell cycle arrest, but also can cause the cell to maintain the state of arrest, and perhaps, induce apoptosis, by inhibiting enzymes that would otherwise turn off the process of cell cycle arrest.

Importantly, it has also been discovered that not only do antioxidants increase the cytotoxicity of antineoplastic agents to abnormally proliferating cells, they also decrease the toxicity of antineoplastic agents to normal cells. Therefore, antioxidants both increase the effectiveness and decrease the toxicity of antineoplastic agents. The palliative effect on normal cells is pronounced in epithelial cells. It has, in particular, been discovered that antioxidants exhibit this effect on cells other than white blood cells, as previously reported by Borch in U.S. Pat. Nos. 5,035,878 and 5,294,430.

Therefore, the invention includes a method to decrease the toxicity of an antineoplastic agent administered for the treatment of a solid growth of abnormally proliferating cells, comprising administering an antioxidant prior to, with, or following the antineoplastic treatment, as well as a method to increase the therapeutic index of an antineoplastic agent administered for the treatment of a solid growth of abnormally proliferating cells, comprising administering an antioxidant prior to, with, or following the antineoplastic treatment.

At least in certain cell lines, it has been discovered that antioxidants increase the cytotoxicity of antineoplastic drugs by affecting a post translational modification of C/EBPβ (CCAAT/Enhancer Binding Protein (C/EBP) β), also known as NF_IL6, AGP/EBP, LAP, IL-6DBP, rNF_IL6, and CRP2 (5–11)), which is a member of a diverse group of nuclear transcription factors that contain a leucine zipper motif required for dimer formation and a basic DNA binding domain which facilitates the interactions between these factors and the regulatory domains of promoters and/or enhancers of target genes. C/EBPβ activates several acute-phase protein genes through the NF_IL6 responsive elements, implying that it has a nuclear target(s). C/EBPβ also has been shown to be responsible for the regulation of genes encoding albumin, c-fos and several adipocyte-specific proteins. Furthermore, C/EBPβ has been implicated in the activation of various genes involved in inflammatory and immune responses, including the interleukin-1 (IL-1) and interleukin-8 (IL-8), granulocyte macrophage/colony-stimulating factor, and immunoglobulin genes. Thus, C/EBPβ is a pleiotropic transactivator involved in a myriad of signal transduction and cell differentiation events.

In one pathway, which may not be exclusive, it has been discovered that antioxidants increase the cytotoxicity of antineoplastic drugs through a cascade of events that include: (I) increasing the level of cAMP, which causes the activation of protein kinase A, an enzyme that phosphorylates C/EBPβ, which on phosphorylation is then translocated from the cytosol to the nucleus of the cell wherein it mediates the induction of p21, which causes an arrest of cell growth; and (II) preventing the dephosphorylation of C/EBPβ in the nucleus (and thus deactivation and delocalization) through the inhibition of protein phosphatase 2A (PP2A). The inhibition of PP2A activity is caused by a decrease in methyltransferase activity, an enzyme which carboxymethylates the catalytic subunit of PP2A, which is involved in maintaining PP2A in an active form. Decreased methylcarboxylation results in decreased PP2A enzymatic dephosphorylation of C/EBPβ as a substrate. By simultaneously inducing the phosphorylation of C/EBPβ and inhibiting the dephosphorylation of C/EBPβ, antioxidants maintain C/EBPβ in an active state in the nucleus of the cell, which induces the continued expression of a cyclin-dependent kinase inhibitor, $p21^{WAF1/CIP1}$ and subsequent cell cycle arrest.

Therefore, more generally, the invention includes a method for increasing the localization of the C/EBPβ protein in the nucleus of a cell that includes the step of administering an antioxidant to the interior of the cell. It has been discovered that this method maintains the C/EBPβ protein in an active, phosphorylated state, which induces cell growth arrest and apoptosis.

As one nonlimiting example, the present invention demonstrates that compounds exhibiting antioxidant properties (for example, pyrrolidinedithiocarbamate, "PDTC," and the vitamin E analogue, Trolox®) decrease DNA replication in human colorectal cancer cells by the induction of $G_1$ cell cycle arrest and/or apoptosis. However, antioxidant compounds have no effect on normal human colonocytes, keratinocytes or mammary epithelial cells (see Table 1). Cell cycle perturbations were more pronounced in colorectal cancer cells expressing mutant p53 compared to wild type p53. Induction of cell cycle arrest and apoptosis correlated with sustained induction of the cyclin-dependent kinase inhibitor, $p21^{WAF1CIP1}$. Treatment with antioxidants in combination with 5-FU significantly reduced anchorage-independent colorectal cancer cell growth. Furthermore, antioxidants alone significantly reduced growth of established colorectal cancer tumors in athymic mice, and the combination of 5-FU and antioxidant either arrested tumor growth (Trolox®) or caused tumor regression (pyrrolidinedithiocarbamate).

DKO-I cells (a human colorectal cancer cell line) constitutively expressing an epitope-tagged C/EBPβ protein were used to further investigate whether a post-translational modification (phosphorylation) of C/EBPβ is responsible for the observed increase in C/EBPβ activity. In vivo labeling with [$^{32}$P]orthophosphate followed by immunoprecipitation revealed a four to six fold increase in the phosphorylation of epitope tagged C/EBPβ in response to PDTC or forskolin (3R,3α,4aβ,5β,6β,6aα,10α,10aβ,10bα)-5-(acetyloxy)-3-ethenyldodecahydro-6,10,10b-trihydroxy-3,4a,7,7,10a-pentamethyl-1H-naphtho[2,1-b]pyran-1-one) with no change in the amount of protein. As a means of mapping the in vitro phosphorylation site(s) within C/EBPβ, deletion analysis of C/EBPβ was performed. Truncated versions of C/EBPβ that contained only the 160 or 200 COOH-terminal amino acids were poor substrates for PDTC-induced phosphorylation, whereas mutant C/EBPβ that contained the 305 COOH-terminal amino acids was phosphorylated by PDTC as efficiently as the full-length C/EBPβ. Closer inspection of the primary amino acid sequence between 236 and 305 revealed that this region contained a consensus PKA phosphorylation site (Arg-X-Ser$^{299}$-X; Sequence ID No. 1).

It appears that phosphorylation of Ser$^{299}$ of C/EBPβ following activation of the cAMP-dependent protein kinase-mediated pathway, is critical for nuclear translocation of this protein and subsequent transactivation of genes in response to an altered intracellular redox status.

The deactivation of C/EBPβ in the nucleus occurs by dephosphorylation of this transcriptional factor by protein phosphatase 2A (PP2A). This enzyme is activated by carboxymethylation of the catalytic subunit of PP2A by methyltransferase. In further experiments, it was established that carboxymethylation of the catalytic subunit of protein phosphatase 2A is inhibited by PDTC as an exemplary antioxidant, and further that the loss of carboxymethylation is caused by an inhibition of activity of methyltransferase. These results support the fact that antioxidants prevent the dephosphorylation of C/EBPβ in the nucleus (and thus deactivation) by protein phosphatase 2A (pp2A) by inhibition of methyltransferase which is involved in maintaining protein phosphatase 2A in an active form. Decreased methylcarboxylation results in decreased PP2A enzymatic dephosphorylation of C/EBPβ as a substrate. It was further discovered that the evaluated antioxidants have little or no effect on protein phosphatase 1 (PP 1).

BRIEF DESCRIPTION OF THE FIGURES

The figures presented herein illustrate preferred embodiments of the invention and are not considered to limit the scope of the invention.

FIG. 1C illustrates the negative association between intracellular redox status and cell cycle perturbations. Changes in the intracellular redox status were determined by the measurement of endogenous $H_2O_2$ levels. Background fluorescence was subtracted from each reading. Values are expressed as corrected DHR mean per 10$^4$ cells±s.e.m. The percentage of $G_1$ (circle) or apoptotic (TUNEL-positive: square) cells by flow cytometric analysis.

FIG. 1E shows that pyrrolidinedithiocarbamate and vitamin E augment 5-FU or doxorubicin induced growth inhibition in vitro. HCT 116 and HCT 15 cells were seeded in soft agar as described above containing increasing concentrations of either 5-FU ($5 \times 10^{-8}$ to $5 \times 10^{-5}$ M) or doxorubicin ($1 \times 10^{-9}$ to $1 \times 10^{-6}$ M), in the presence or absence of pyrrolidinedithiocarbamate (70 μM) or vitamin E (3 mM). Colonies were scored after 10 days and IC$_{50}$ values were calculated as the concentration of 5-FU or doxorubicin required to reduce basal colony formation by 50% (±s.e.m.). Values are representative of three experiments carried out in quadruplicate.

FIGS. 3A–3C show that pyrrolidinedithiocarbamate bypasses p53 to induce p21$^{WAF1/CIP1}$ expression.

FIG. 3A shows that p21$^{WAF1/CIP1}$ protein levels were increased in human CRC cells expressing functional (HCT 116) and mutant (HCT 15) p53 following pyrrolidinedithiocarbamate treatment. CRC cells were treated as indicted with pyrrolidinedithiocarbamate (70 μM) and subjected to Western blot analysis.

FIG. 3B shows p53-independent induction of p21$^{WAF1/CIP1}$ mRNA by pyrrolidinedithiocarbamate in human CRC cells. Exponentially growing, asynchronous human CRC cells were incubated in serum-containing medium with 70 μM pyrrolidinedithiocarbamate. In addition, HCT 116 cells containing HPV16 E6 to target degradation of p53 were analyzed. Cells were collected at indicated time points and prepared for poly(A)$^+$ mRNA isolation. Samples (3 μg) were electrophoresed through a 1% (w/v) formaldehyde/agarose gel and transferred onto nitrocellulose membranes. Northern blotting hybridization was performed at 43° C. with a

[32P]-labeled p21$^{WAF1/CIP1}$ probe. IB15 is shown as a control for equivalent loading and transfer.

FIG. 3C shows that antioxidant-induced apoptosis requires p21$^{WAF1/CIP1}$ expression. HCT 116 cells, containing either functional p21+/+ or deleted p21$^{WAF1/CIP1}$, were treated with the indicated concentrations of pyrrolidinedithiocarbamate or vitamin E for 24 hours and apoptosis was determined by TUNEL analysis. Values are expressed as percent TUNEL positive cells and represent mean±s.e.m. of triplicate measurements.

Figure 4A:
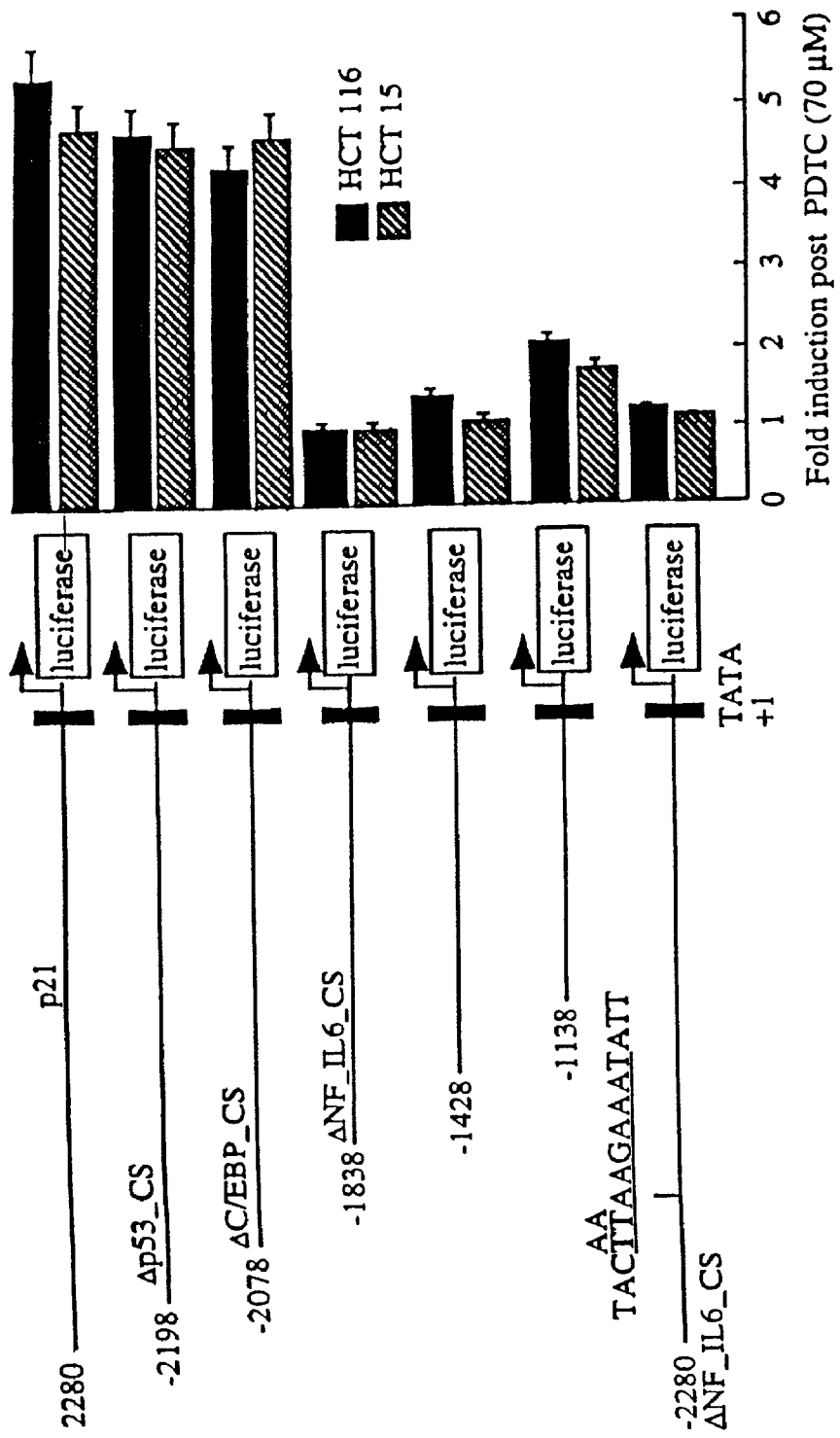

FIG. 4A shows that pyrrolidinedithiocarbamate induces p21$^{WAF1/CIP1}$ transcriptional activity via the NF_IL6 consensus sequence. A 2.4 kilobase pair p21$^{WAF1/CIP1}$ promoter sequence and mutants were fused to a luciferase reporter gene. TATA represents the p21$^{WAF1/CIP1}$ TATA box located 45 bp from the transcription start site (defined as +1). −2280, −2198, −2078, −1838, −1428 and 1138 define 5' end points for terminal deletion constructs. The −2280 ΔNF_IL6 construct contains the intact promoter with a two base pair mutation at the NF_IL6 site. All reporter constructs were transfected into HCT 116 or HCT 15 cells, and antioxidant-induced luciferase activity was measured in relative light units (RLU) after 24 hours. Luciferase activity was normalized to CAT activity, and results were reported as fold activation above basal levels.

Figure 4B:
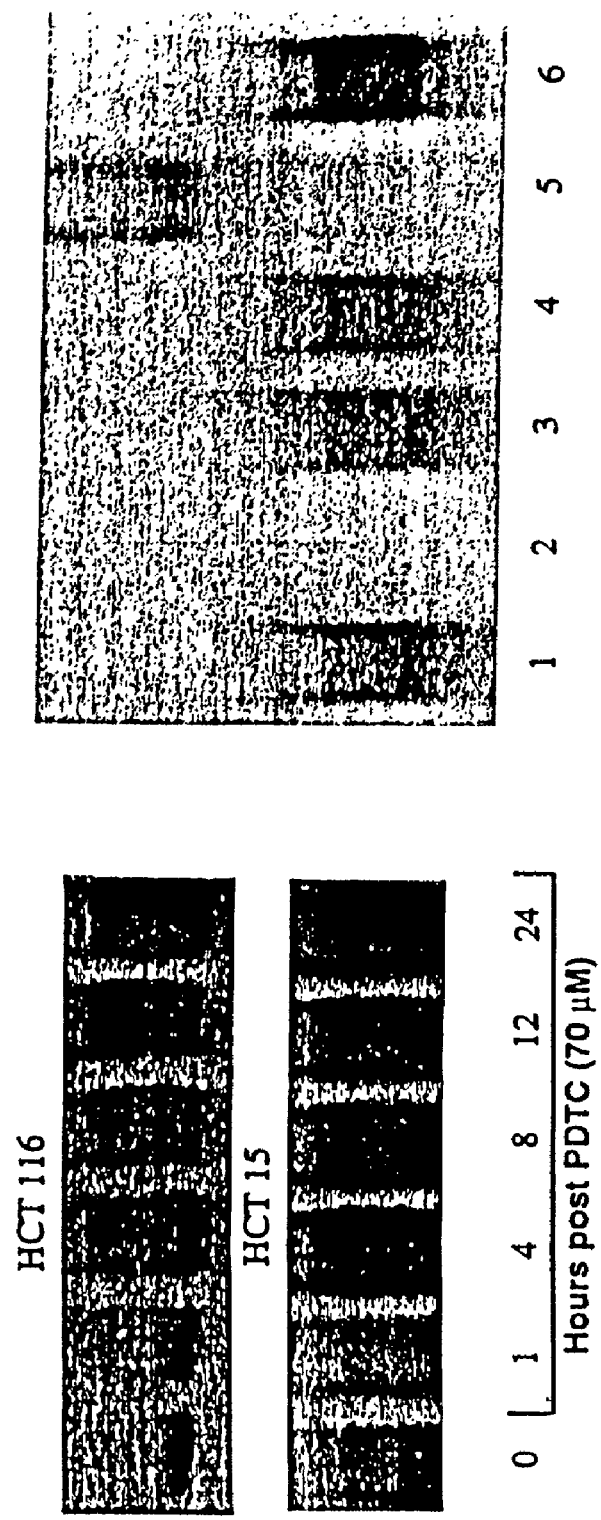

FIG. 4B shows that pyrrolidinedithiocarbamate treatment induces C/EBPβ DNA binding activity. Left panel: HCT 116 and HCT 15 cells were treated with 70 μM pyrrolidinedithiocarbamate for the indicated times, nuclear extracts were incubated with a γ-$^{32}$P-labeled p21-NF_IL6 oligonucleotide. Right panel: Lanes 1–3, competition controls were performed on a nuclear extract derived from HCT 116 cells treated with pyrrolidinedithiocarbamate for 12 hours (lane 1), with excess unlabeled wild-type (lane 2) and mutant (lane 3) oligonucleotide. Lanes 4–6, supershift analysis were performed with C/EBPα (lane 4), β (lane 5), or δ (lane 6) polyclonal antibodies.

Figure 4C:
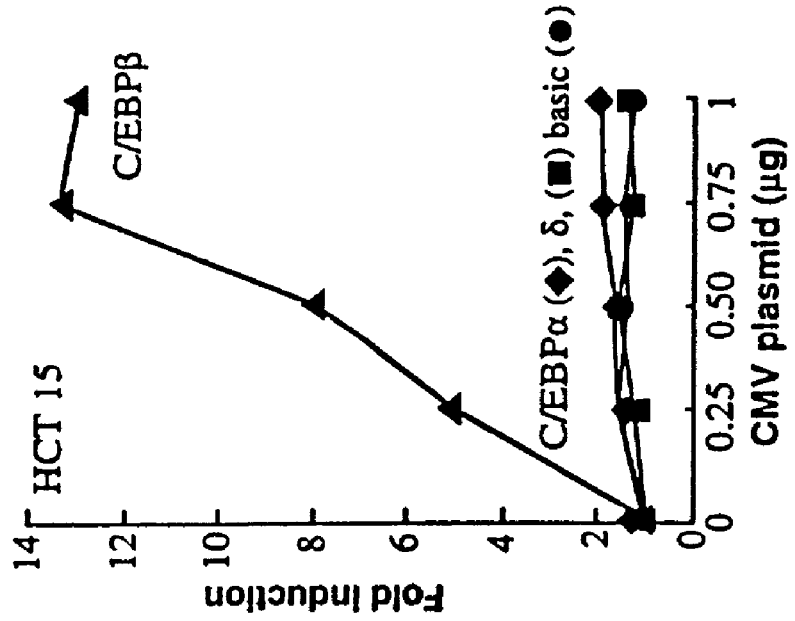

FIGS. 4C and D shows that C/EBPβ can stimulate p21$^{WAF1/CIP1}$ promoter activity. HCT 116 (FIG. 4C) or HCT 15 (FIG. 4D) cells were transfected with the indicated amounts of cytomegalovirus (CMV) expression plasmids, containing C/EBPα, β or δ cDNAs, and 3 μg of p21$^{WAF1/CIP1}$-luciferase. A control plasmid was included in FIG. 4A.

Figure 4D:
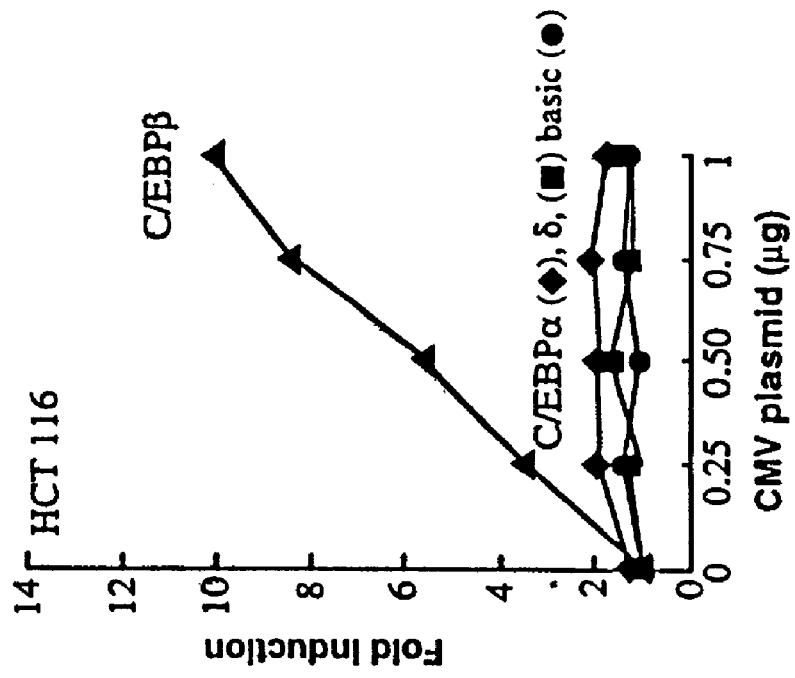
Figure 4E:
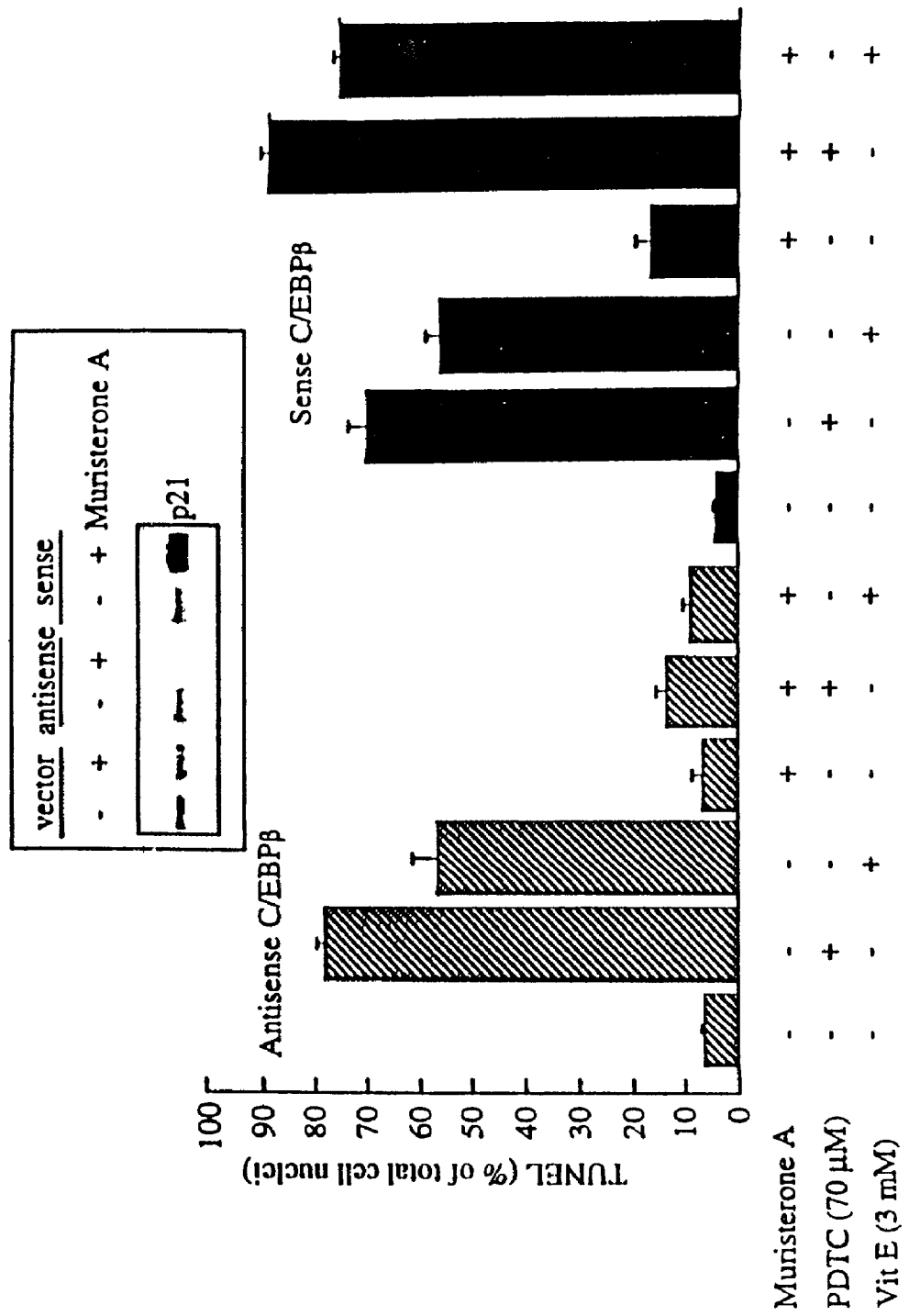

FIG. 4E shows that C/EBPβ regulates cellular sensitivity to antioxidant-induced apoptosis. Control HCT 15 cells and sense or antisense C/EBPβ cell lines were grown in the presence or absence of 10 μM muristerone A and/or pyrrolidinedithiocarbamate (70 μM) or vitamin E (3 mM) for 24 hours. The apoptotic indices were estimated by the percentage of TUNEL-positive cells scored under a light microscope at 200-fold magnification and values are expressed as mean±s.e.m. for triplicate samples. The inset shows a representative Western blot for p21$^{WAF1/CIP1}$ protein levels in both transfected cell lines, grown in the presence or absence of 10 μM muristerone A.

Figure 4F:
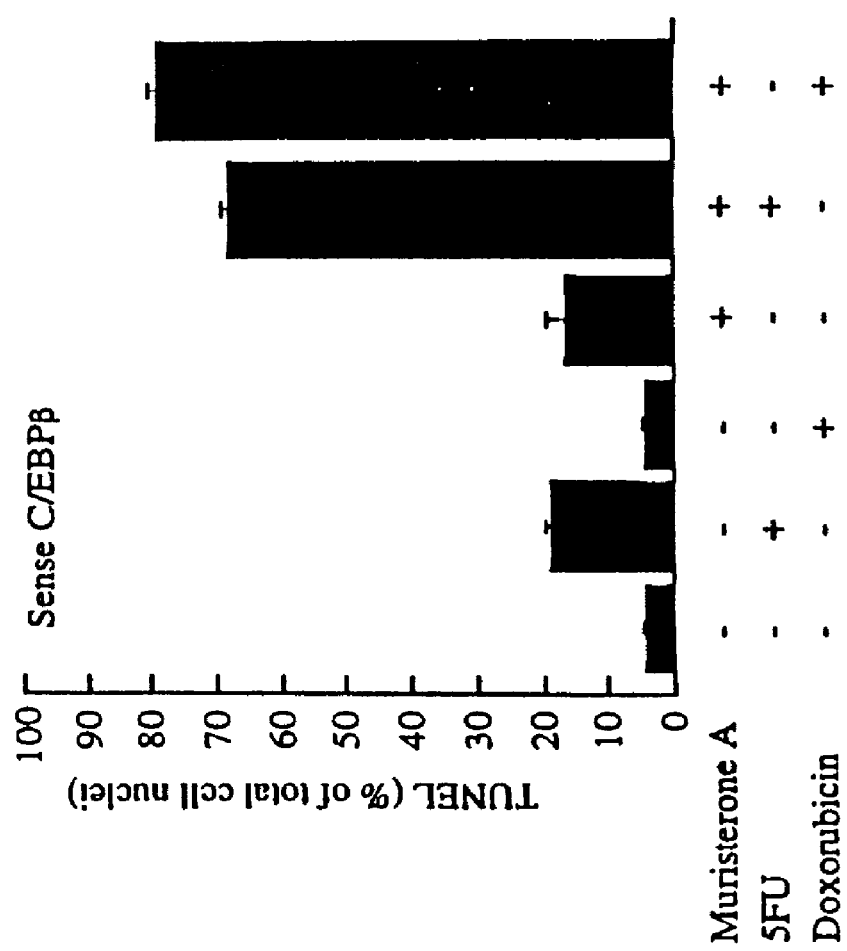

FIG. 4F shows that elevated C/EBPβ protein levels enhance chemotherapeutic agent cytotoxicity in vitro. Control HCT 15 cells and the sense C/EBPβ cell line were induced with 10 μM muristerone A and exposed to either 5-FU (1.5 μM) or doxorubicin (0.1 μM) for 24 hours. The apoptotic index was calculated as described in FIG. 4C.

Figure 5A:
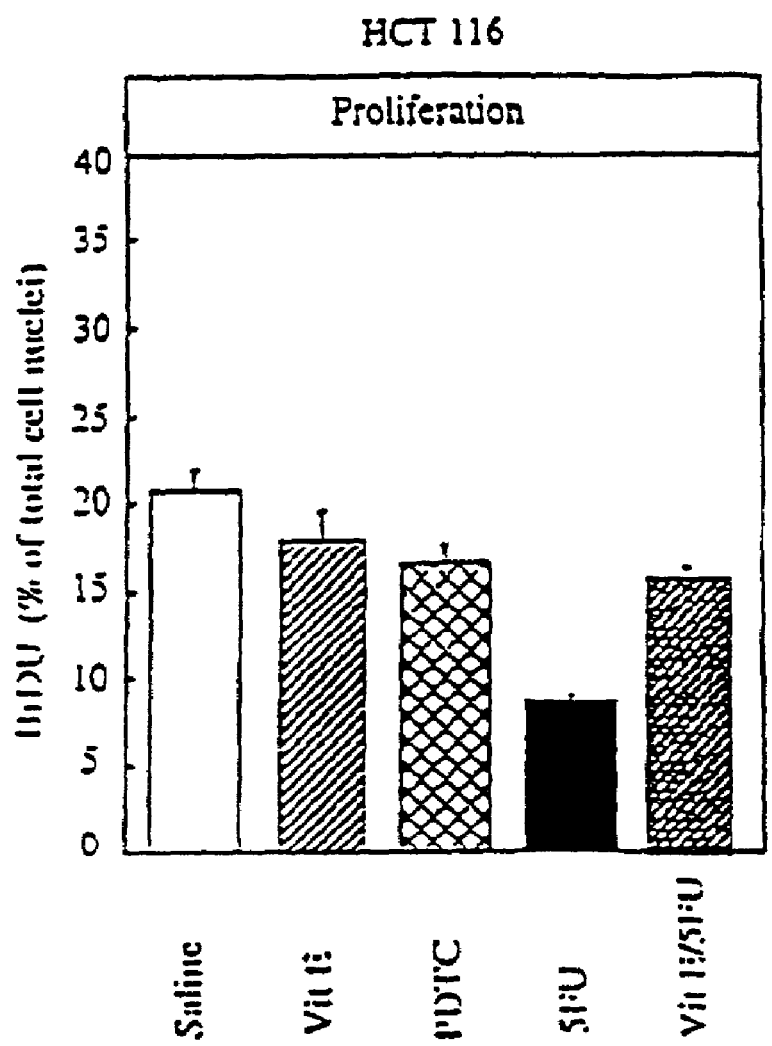
Figure 5B:
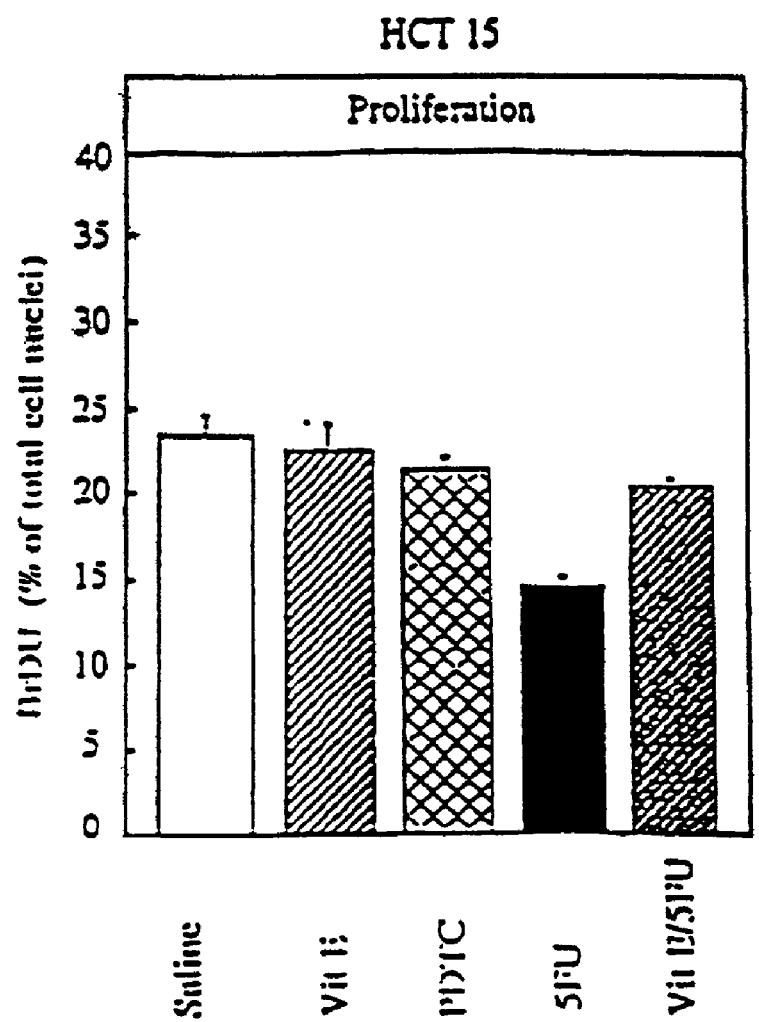

FIGS. 5a and 5b are bar graphs of the growth of BrDU-labelled cells (percent of total cell nuclei; BrDU refers to bromodeoxyuridine) from colorectal cell xenografts derived from athymic mice treated with saline, vitamin E, PDTC, 5-FU, and the combination of vitamin E and 5-FU, as a measure of the effect of the test compound on proliferation of HCT 116 and HCT 15 cells.

Figure 6A:
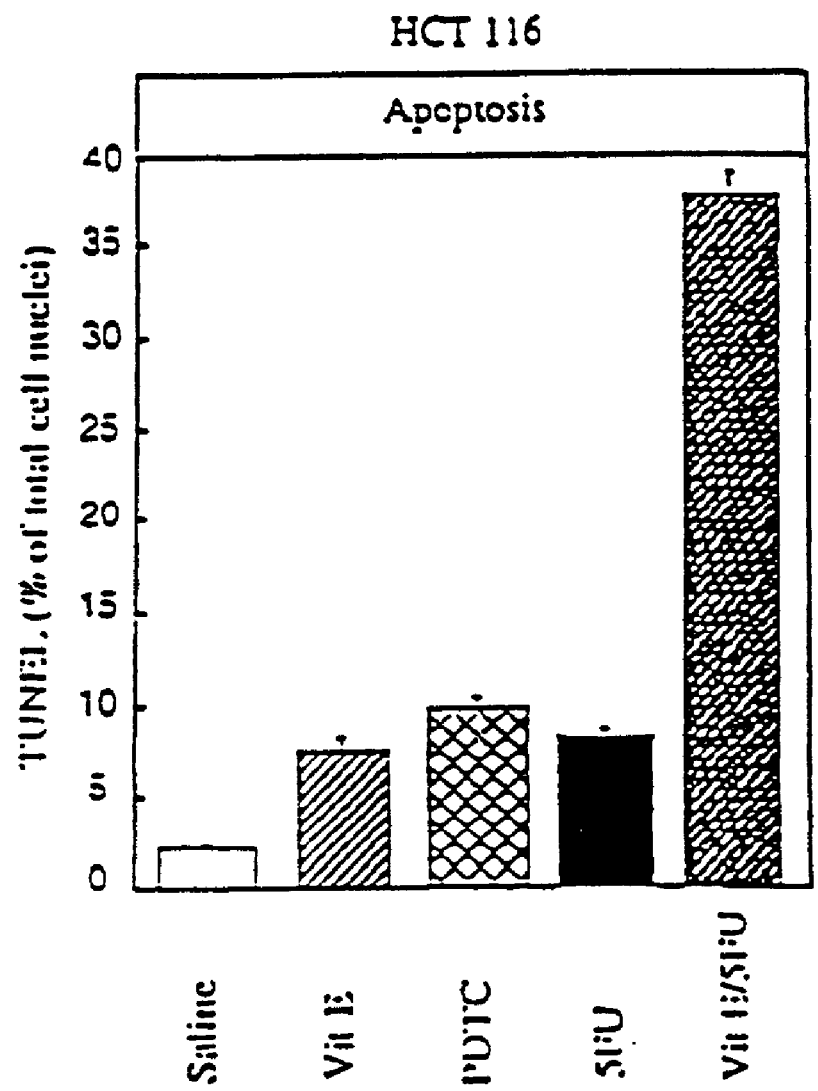
Figure 6B:
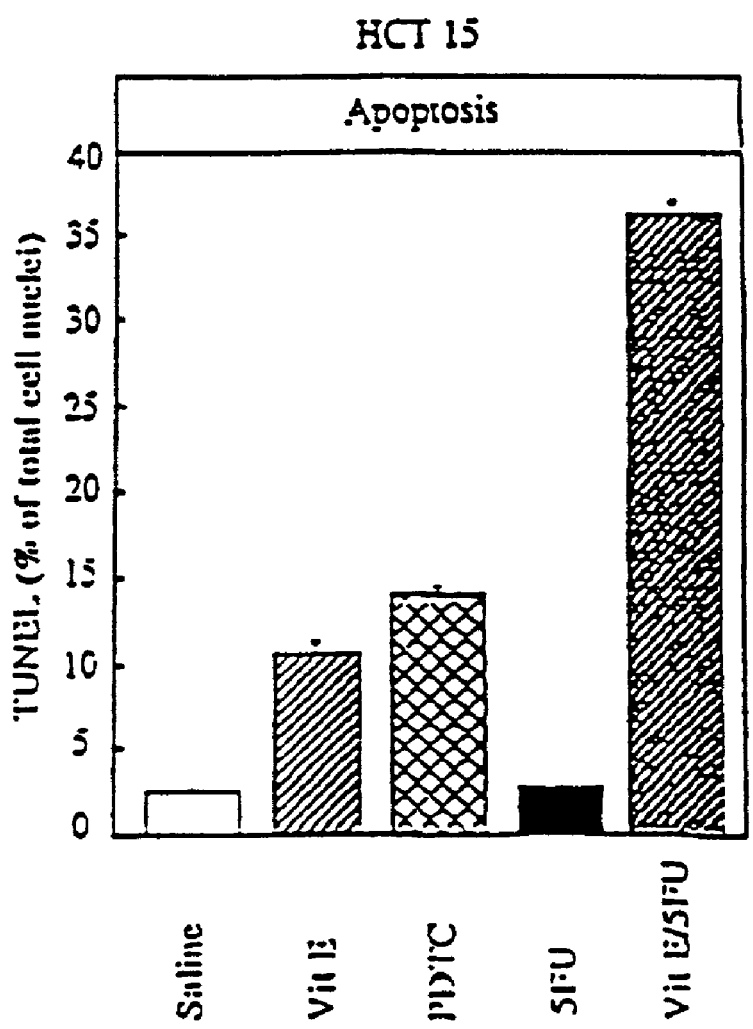
Figure 7A:
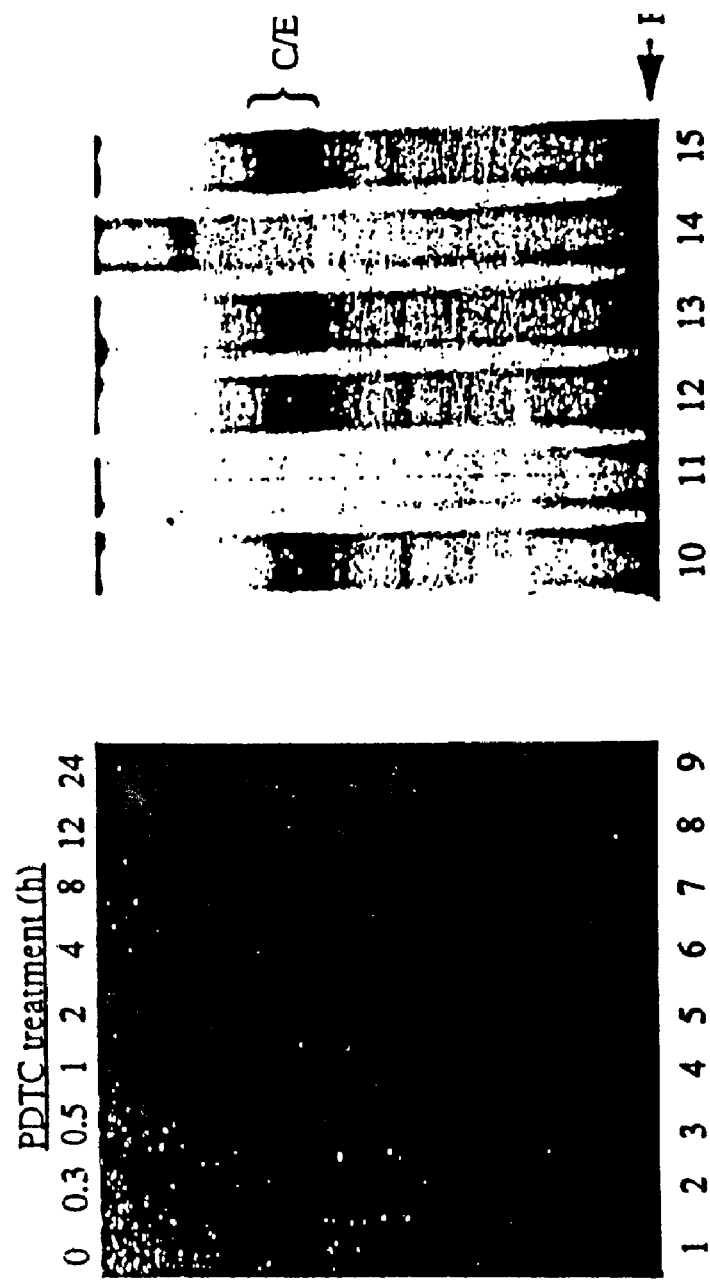
Figure 7B:
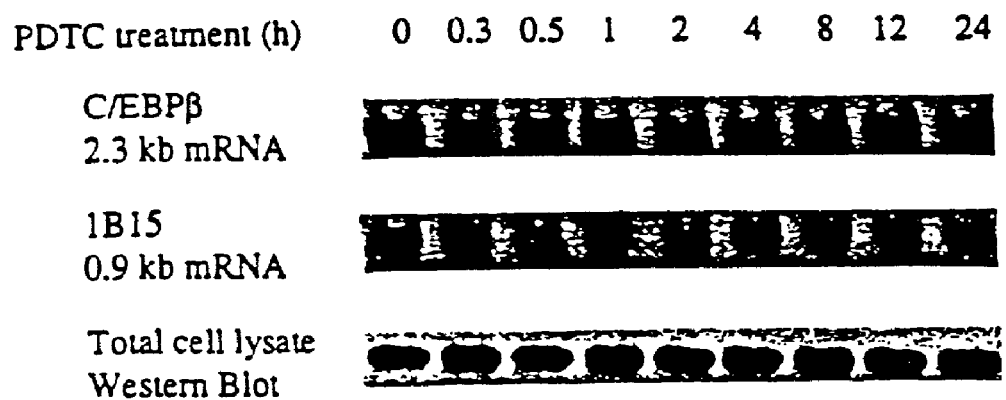
Figure 7C:
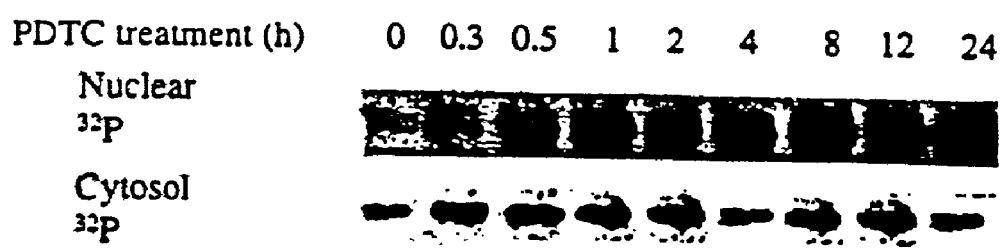
Figure 7D:
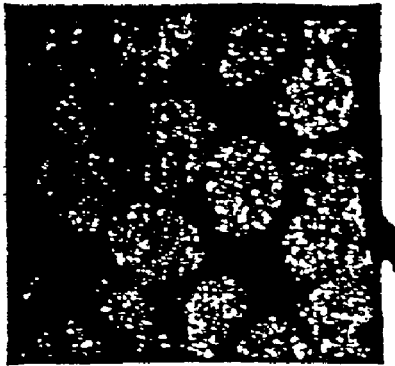
Figure 7D:
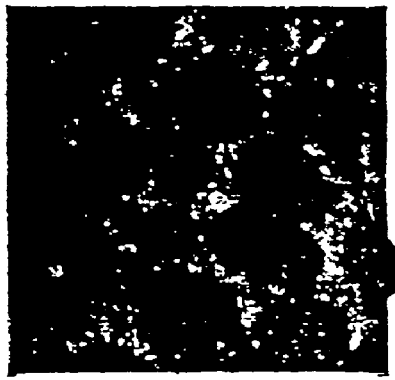
Figure 7D:
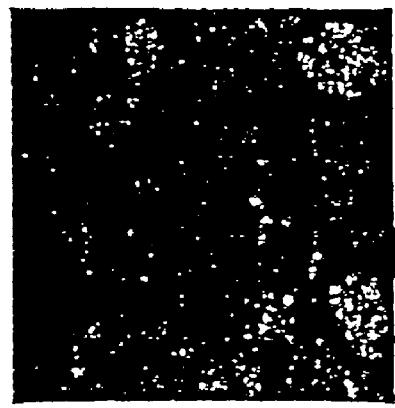

FIGS. 6a and 6b are bar chart graphs of TUNEL-positive cells from colorectal cell xenografts derived from athymic mice (percent of total cell nuclei; TUNEL REFERS TO TdT-mediated dUTP-nick-end-labeling) treated with saline, vitamin E, PDTC, 5-FU, and the combination of vitamin E and 5-FU, as a measure of the effect of the test compound on apoptosis. Tumor tissues were fixed overnight in 4% (v/v) paraformaldehyde and embedded in paraffin according to standard histological procedures. Sections were pretreated with 10 mM citrate buffer (pH 6.0) and incubated with PC10 monoclonal antibody against BrDU (Boehringer Mannheim). TdT labeling of fragmented DNA (TUNEL) was performed according to manufacturer's instructions. The proliferative index (percent of total BrDU cell nuclei) and the apoptotic index (TUNEL) were estimated by the percentage of cells scored under a microscope at 200-fold magnification.

FIGS. 7A–7D illustrate that PDTC treatment induces C/EBPβ DNA binding activity via a post-translational modification. (A) DKO-1 cell were treated with 70 μM PDTC for the indicated times, nuclear extracts were prepared with a [γ-$^{32}$P]-labeled p21-NF_IL6 oligonucleotide (Lanes 1–9). Specificity assays: Lanes 10–12, competition controls were performed on a nuclear extract derived from DKO-1 cells treated with PDTC for 3 hours (lane 5), with excess unlabeled wild-type (lane 11) and mutant (lane 12) oligonucleotide. Lanes 13–15, supershift analyses were performed with C/EBPβ (lane 13), β (lane 14), or δ (lane 15) polyclonal antibodies. (B) Parallel DKO-1 cell cultures were treated with PDTC (70 μM) for the indicated times. Poly(A) was isolated and treatment-related variations in C/EBPβ mRNA levels were evaluated by Northern blot analysis. IB15 is shown as a control for equivalent loading and transfer. (C) Parallel DKO-1 cultures were treated with PDTC (70 μM) in the presence of [$^{32}$P]orthophosphate. C/EBPβ from cytosolic and nuclear fractions were purified by immunoprecipitation from cells before (time 0) or at the indicated times after PDTC treatment. Treatment-related variations in the localization of C/EBPβ were analysed by SDS-PAGE followed by autoradiography or Western blot analysis (100 μg of total cellular protein/lane). (D) DKO-1 cells were cultured in the presence of PDTC (70 μM) for 1 hour and then processed for immunocytochemistry to detect treatment-related differences in the compartmentalization of C/EBPβ protein. In all experiments, parallel cultures treated with preimmune sera or primary anti-C/EBPβ antisera that had been preincubated with in vitro translated C/EBPβ protein demonstrated no fluorescent signal after treatment with the secondary Cy3-conjugated antibody. Representative photomicrographs show anti-C/EBPβ stained cells before and after PDTC treatment.

Figure 8A:
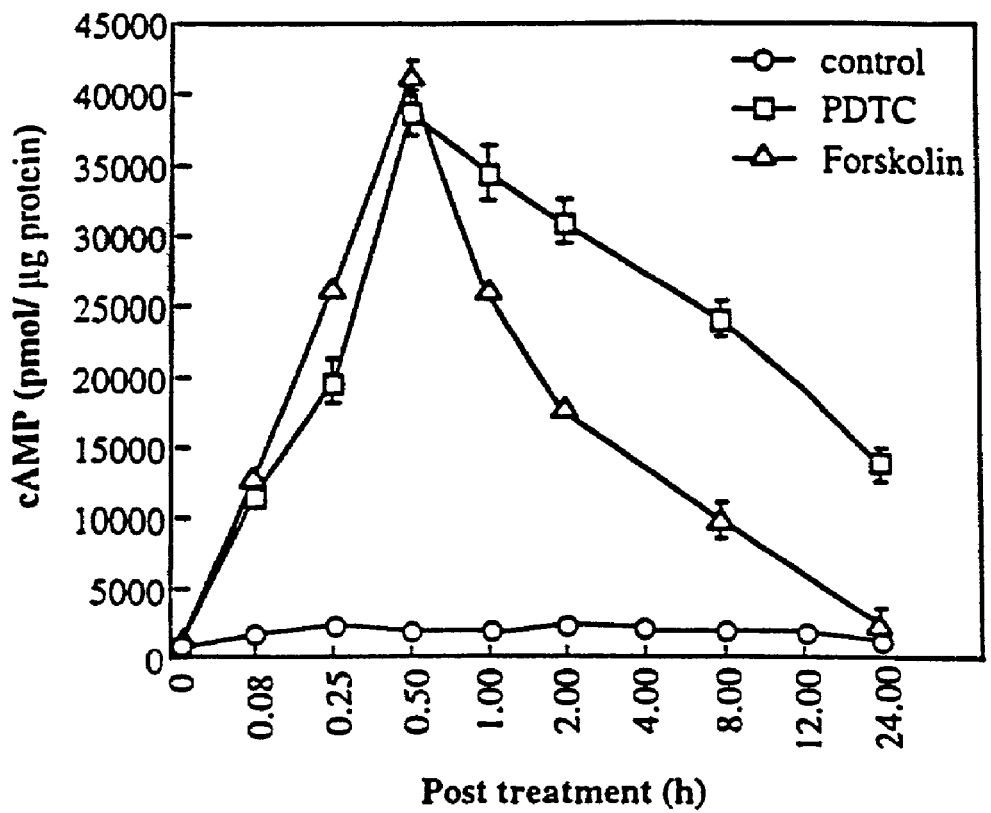
Figure 8B:
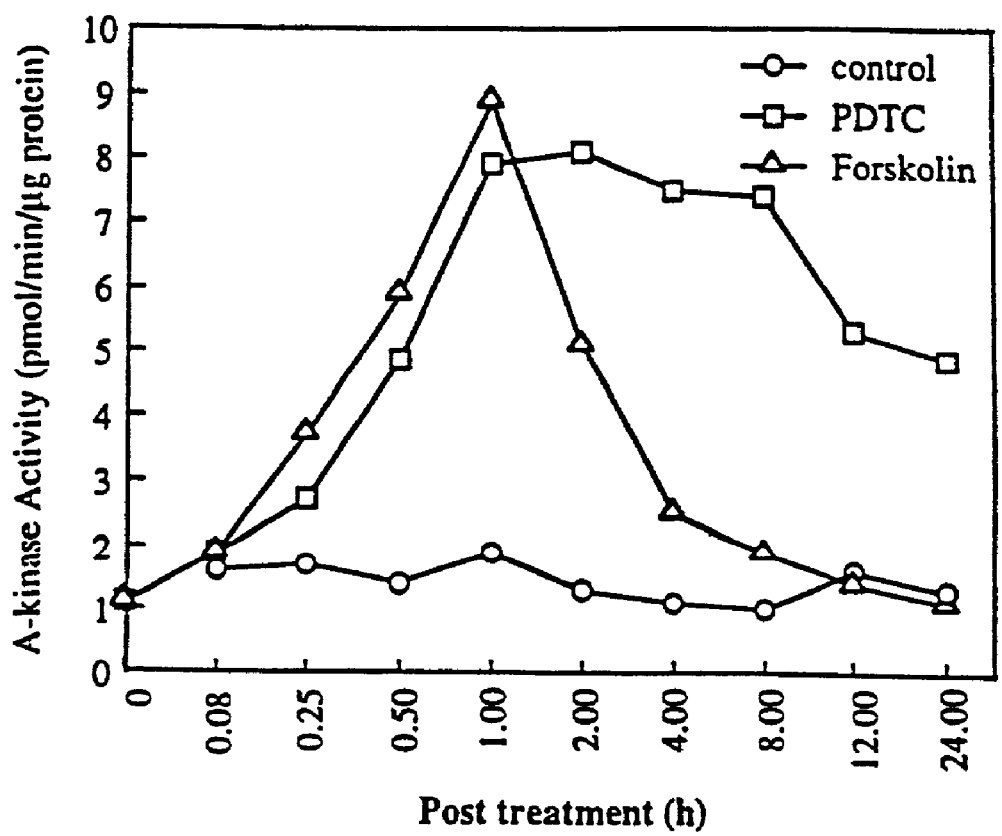

FIGS. 8A–8B illustrate the effect of PDTC on endogenous cAMP levels and PKA activity. DKO-1 cells were treated with 70 μM PDTC for the indicated times. Cell lysates were prepared and assayed for (A) endogenous cAMP levels or (B) PKA activity. The values are expressed as pmol mean per μg protein±s.e.m. and are representative of three experiments carried out in quadruplicate.

Figure 9A:
Figure 9A:
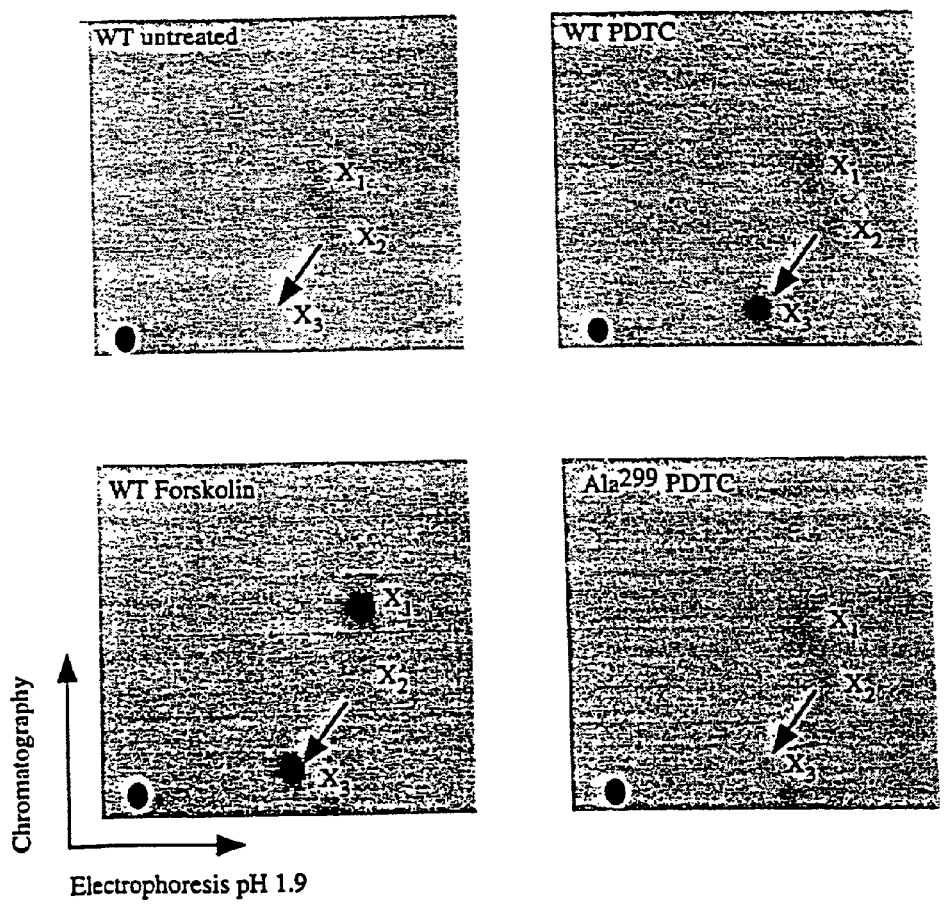
Figure 9C:
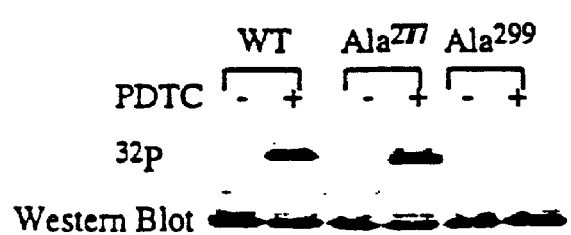

FIGS. 9A–9C illustrate that PDTC phosphorylates C/EBPβ at Ser$^{299}$. (A) Endogenous C/EBPβ from [$^{32}$P] orthophosphate-labeled DKO-1 cells (2 mCi/ml. 3 h) that were treated with either 0 μM (lane 1), 70 μM PDTC (lane 2) or 50 μM forskolin were immunoprecipitated with anti C/EBPβ antibodies. Labeled proteins were visualized by SDS-PAGE followed by autoradiography. (B) Tryptic phosphopeptide maps of in vivo labeled epitope-tagged C/EBPβ. Wild type (WT) and mutant (Ala$^{299}$) C/EBPβ, immunoprecipitated from PDTC treated or untreated DKO-1 cells with the antibody to the FLAG-epitope, were digested with trypsin and the phosphopeptides separated by electrophoresis and thin-layer chromatography and visualized by autoradiography, $X_{1,2}$ were constitutively phosphorylated. The level of phosphopeptide $X_3$ was increased after PDTC treatment in cells transfected with the wild type, but not mutant, protein. The circle indicates the origin. (C) Comparison of the in vivo phosphorylation of wild type and Ala substitution mutants of C/EBPβ from untreated cells and cells treated with PDTC. Autoradiography (top) and C/EBPβ immunoblot (bottom) are shown.

Figure 10A:
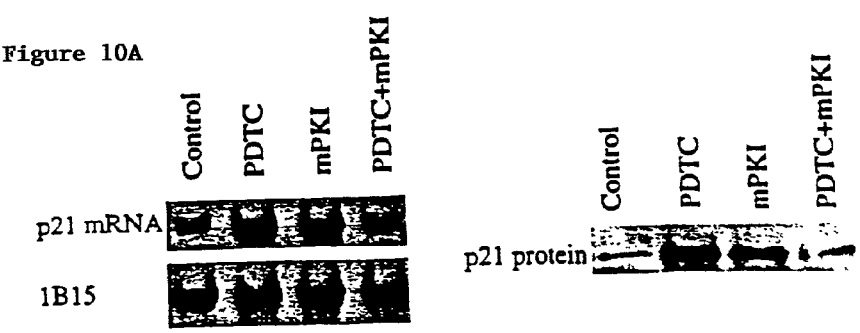
Figure 10B:
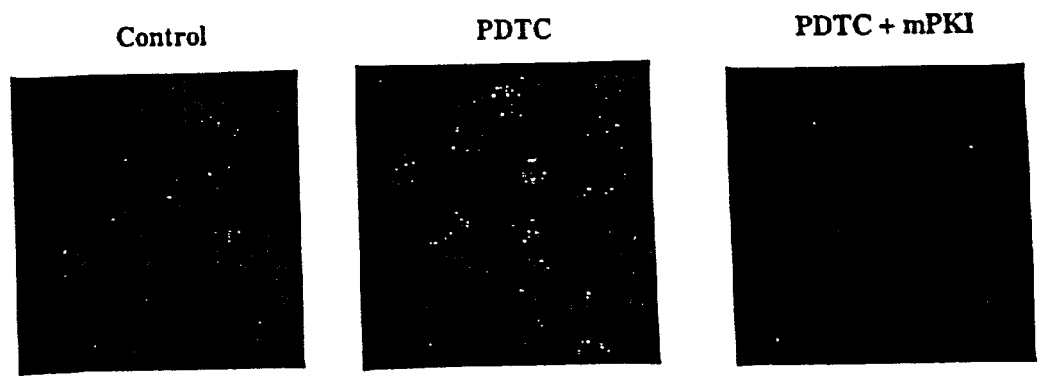

FIGS. 10A–10B illustrate that PKA phosphorylation of C/EBPβ is required for nuclear translocation. (A) Parallel DKO-1 cell cultures were treated with PDTC (0 or 70 μM) for 3 hours. Poly(A)$^+$ mRNA and protein were isolated from each group and treatment-related variations in C/EBPβ mRNA and protein levels were evaluated by Northern or Western blot analysis. IB15 is shown as a control for equivalent loading and transfer. (B) DKO-1 cells were treated with PDTC (0 or 70 μM) or PDTC and mPKI (myristylated protein kinase A inhibitor; 1 μM) for 3 hours. Cells were fixed with paraformaldehyde and C/EBPβ protein visualized by immunofluorescence staining. Treatment of cells with mPKI alone failed to induce nuclear translocation of C/EBPβ (data not shown).

Figure 11:
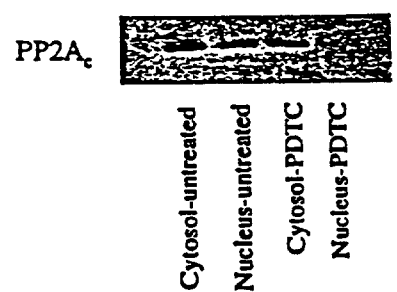

FIG. 11 illustrates that carboxymethylation of the catalytic subunit of protein phosphatase 2A is inhibited by PDTC. DKO-1 cells were incubated in serum-containing media containing [methyl-$^3$H]S-adenosyl methionine and/or 70 μM PDTC for three hours. Cytosolic or nuclear fractions were prepared and C/EBPβ immunoprecipitated using standard methods. Antibody/antigen complexes were resolved by SDS-PAGE and the presence of PP2Ac was detected by fluorography. PDTC inhibited carboxymethylation of PP2A subunit in nuclear fractions and to a lesser extent, in cytosolic fractions.

Figure 12:
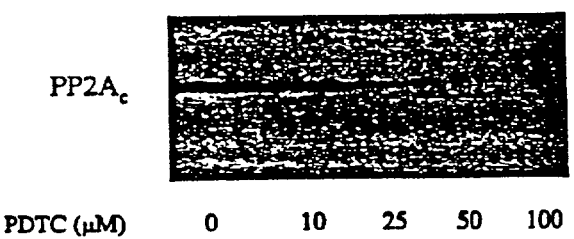

FIG. 12 illustrates that PDTC inhibits methyltransferase activation of PP2Ac. PP2A (a and c dimer) was incubated in the presence of [methyl-$^3$H]S-adenosyl methionine, increasing concentrations of PDTC and partially purified rat methyltransferase for thirty minutes at 37 degrees C. The reaction was terminated by the addition of SDS-sample buffer. Samples were resolved by SDS-PAGE and the presence of methylated PP2A catalytic subunit visualized by fluorography. As indicated, PDTC selectively inhibits the ability of methyltransferase to carboxymethylate the catalytic subunit of PP2A in a dose dependent manner.

Figure 13:
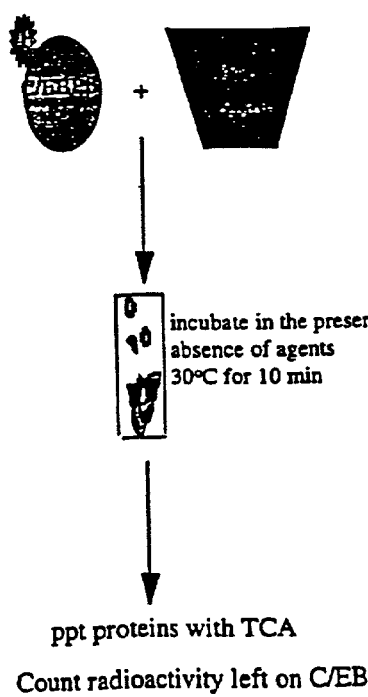
Figure 13:
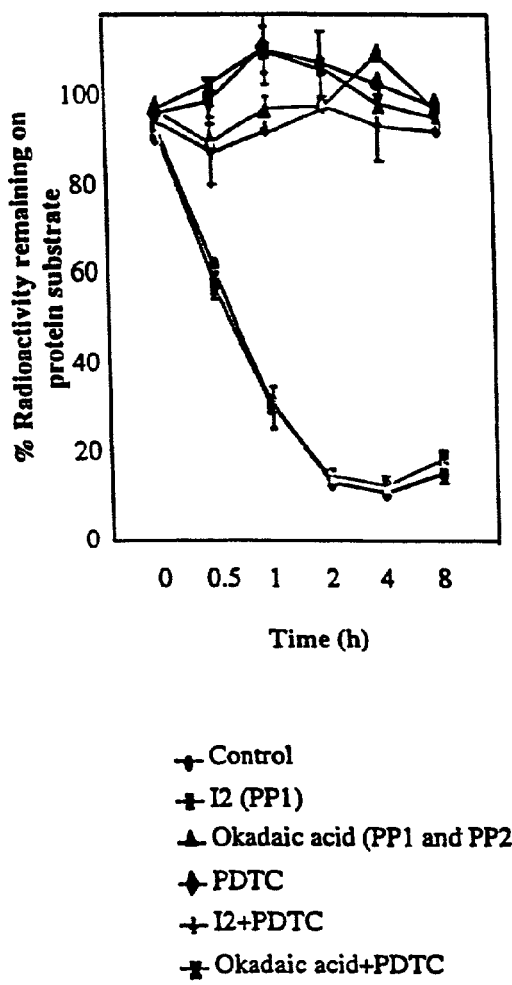

FIG. 13 is a graph of time in hours versus percent radioactivity remaining on the protein substrate. The figure indicates that PDTC inhibits PP2A, but not PP1, activity. The activity of PDTC is compared to I2 (a selective PP1 inhibitor), okadaic acid (an inhibitor of both PP2A and PP1), I2 and PDTC, and okadaic acid and PDTC. DKO-1 cells were grown in the presence of PDTC (test) or not (control). The cells were lysed, and then radioactive phosphorylated C/EBPβ was added. The test compounds were then added, and incubated with the lysate. The protein was collected and the amount of radioactive phosphate remaining in the protein measured.

Figure 14:
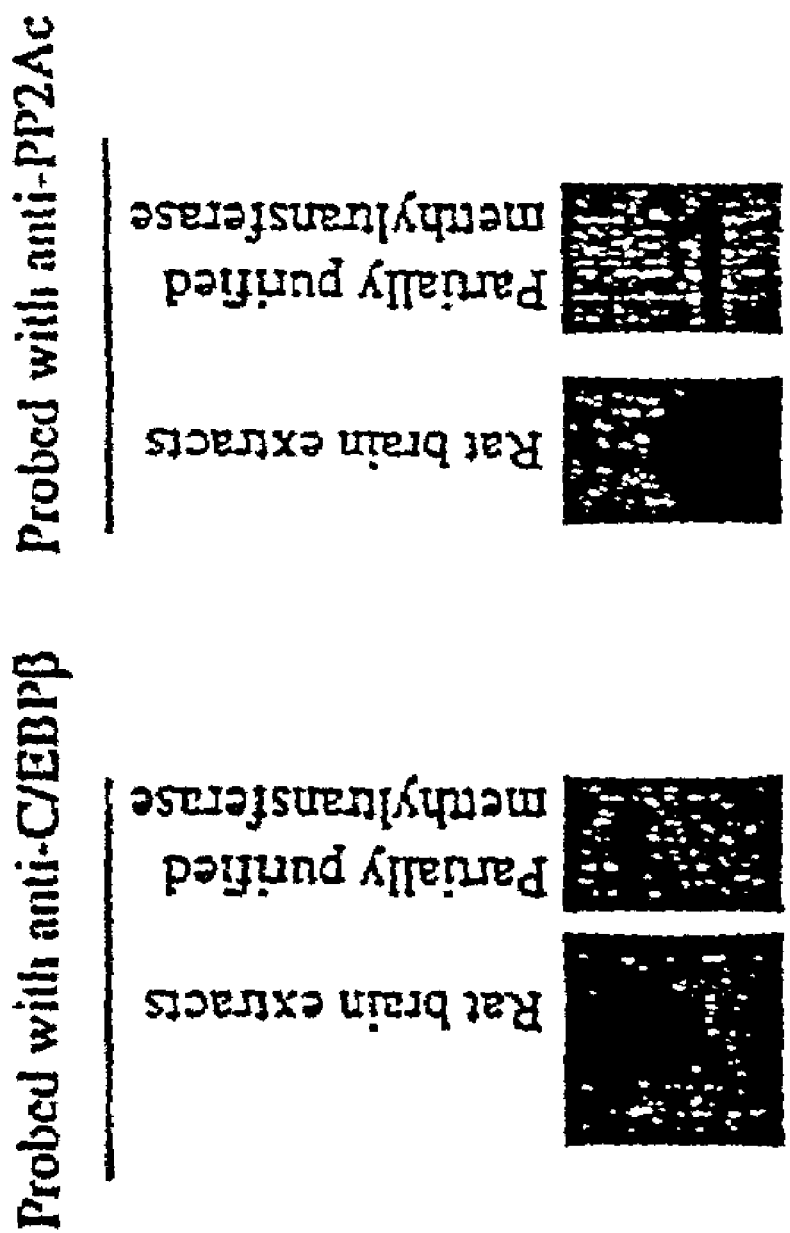

FIG. 14 illustrates that the transcription factor C/EBPβ is complexed with the PP2Ac protein phosphatase. Rat brain soluble extracts were fractionated by phenyl-Sepharose and analyzed for methyltransferase activity using exogenous PP2A heterodimer (a-c complex). The peak of methyltransferase activity was further fractionated by Source Q, a strong anion exchange and gel filtration chromatography. The partially purified methyltransferase illustrated in FIG. 14 represents the peak methyltransferase activity from the gel filtration column. This peak fraction of methyltransferase activity is taken further to DEAE, a weak anion exchange, and MonoQ, a different strong anion exchange resin, columns. Both C/EBPβ and PP2A are detectable following these additional steps. Rat brain extracts are shown as a positive control (C/EBPβ and PP2Ac migrate at approximately 45 and 36 kDa on SDS-PAGE).

DETAILED DESCRIPTION OF THE INVENTION

It has been discovered that antioxidants induce cell cycle arrest and apoptosis in abnormally proliferating cells through a mechanism mediated by the activation of the transcription factor C/EBPβ that binds to a specific site in the p21 promoter to induce p21 expression independent of p53. It has also been discovered that a site-selective phosphorylation at Ser$^{299}$ of C/EBPβ by protein kinase A following antioxidant treatment is essential for the observed nuclear translocation of this protein.

It has also been discovered that antioxidants prevent the dephosphorylation of C/EBPβ in the nucleus (and thus deactivation and delocalization) through the inhibition of PP2A. The inhibition of PP2A activity is caused by a decrease in methyltransferase activity, an enzyme which carboxymethylates the catalytic subunit of PP2A, which is involved in maintaining PP2A in an active form. Decreased methylcarboxylation results in decreased PP2A enzymatic dephosphorylation of C/EBPβ as a substrate. By simultaneously inducing the phosphorylation of C/EBPβ and inhibiting the dephosphorylation of C/EBPβ, antioxidants maintain C/EBPβ in an active state in the nucleus of the cell, which induces the continued expression of p21$^{WAF1/CIP1}$ and subsequent cell cycle arrest.

The methyltransferase responsible for PP2A subunit carboxymethylation in vivo and in vitro represents a unique type of carboxyl methyltransferase. The mammalian type II and type III carboxyl methyltransferases appear to have substantially different properties from the enzyme that carboxymethylates the PP2Ac subunit. Protein carboxyl methyltransferase type II modifies D-aspartyl and L-isoaspartyl residues that accumulate in proteins with aging, and, therefore methylates a different protein containing these amino acids. Carboxyl methyltransferase type III modifies proteins at cysteine, proceeding to the carboxyl terminus of proteins (G-proteins), and requires isoprenylation of cysteine and proteolytic cleavage of the last three carboxyl-terminal residues. Activity of this carboxyl methyltransferase is not altered by antioxidant treatment of colorectal cancer cell line DKO-1 in vitro. Therefore, in vitro data suggests that antioxidants selectively inhibit the methyltransferase responsible for PP2Ac, but not G-protein, methylation.

A novel higher order protein complex has also been identified that consists of C/EBPβ, PP2A and methyltransferase. Thus, another embodiment of this invention is this novel complex in isolated form, for example in at least 70%, and preferably 80 or 90% purity. A method for isolating this enzyme is provided in Example 27.

I. Embodiments of the Invention

Based on the fundamental discoveries described herein, a method for increasing the localization of the C/EBPβ protein in the nucleus of a cell is presented that includes the step of administering an antioxidant to the interior of the cell. It has been discovered that this method maintains the C/EBPβ protein in an active, phosphorylated state, which induces cell growth arrest and apoptosis.

In one embodiment, the invention is a method to enhance the cytotoxic activity of an antineoplastic drug comprising administering an effective amount of the antineoplastic drug to a host in need of treatment in combination with an effective cytotoxicity-increasing amount of an antioxidant. It has been discovered that antioxidants, including those specifically disclosed herein, induce cell cycle arrest (G1, G2, S and M type), and thus are useful to enhance the efficacy of antineoplastic drugs for the treatment of disorders associated with abnormal cell proliferation. It has been discovered that this method maintains the C/EBPβ protein in an active, phosphorylated state, which induces cell growth arrest and apoptosis. In an alternative embodiment, a method is presented to increase the cytotoxicity of an antineoplastic or chemotherapeutic agent against a disorder of abnormal cell hyperproliferation, that includes increasing the phosphorylation state of C/EBPβ protein in a host, for example, an individual or animal in need of such treatment, comprising the step of administering to said individual or animal a cytotoxicity-increasing dose of an antioxidant in combination or alternation with a pharmacologically effective dose of a chemotherapeutic agent.

In another embodiment, the invention is directed to a method of treating a host having a neoplastic condition, comprising the step of administering to the host a therapeutically effective dose of a cytotoxic chemotherapeutic therapy and an antioxidant, wherein the cytotoxic chemotherapeutic therapy is selected from the group consisting of cancer chemotherapeutic agents and radiation therapy. Representative cancer chemotherapeutic agents and antioxidants are listed below. Any radiation therapy that ameliorates a condition of abnormal cellular proliferation is appropriate for use in this method, including ionizing radiation that is particulate or electromagnetic. Suitable and effective dosages of radiation therapy for a wide variety of neoplastic conditions are well known. In one nonlimiting embodiment, radiation therapy is gamma irradiation given at a dose of from about 3,000 centigrey to about 5,000 centigrey over an appropriate time frame, for example, up to six weeks.

The present invention is also directed to a method of increasing expression of the p21 protein as a means to arrest cell growth and induce apoptosis in an individual in need of such treatment, comprising the step of administering to said individual a pharmacologically effective dose of an antioxidant, or a combination of an antioxidant and an antineoplastic agent.

The present invention is further directed to a method of regulating cell cycle arrest ($G_1$, $G_2$, S or M) and apoptosis in an individual in need of such treatment, comprising the step of administering to said individual a pharmacologically effective dose of an antioxidant or a combination of an antioxidant and a antineoplastic agent.

In another embodiment, therapeutic efficacy may be achieved by administration of an effective amount of C/EBPβ, or a protein with substantial homology to C/EBPβ, to achieve the effects described in detail herein. The protein or protein analog can be administered alone or as an adjunct to antineoplastic therapy. A protein with substantial homology to C/EBPβ is defined herein as consisting of or containing a peptide sequence of the form -X1-Arg-X2-Ser-X3 (Sequence ID No. 2) wherein X2 is the C/EBPβ amino acid at position 298, and X1 and X3 represent flanking peptide sequences with substantial homology to those of C/EBPβ.

The term substantial homology refers to a protein or peptide sequence that performs substantially the same function as the parent sequence and has at least 60%, or more preferably, 75%, and most preferably, 90% or 95% or greater, sequence identity. Methods for the effective delivery of proteins are known and can be employed in conjunction with this embodiment to enhance the efficacy of this therapy.

In another embodiment, a synthetic Ser299 phosphorylated C/EBPβ analog can be administered that has a stabilized phosphate bond that is resistant to dephosphorylation. Such stabilized phosphates include, but are not limited to, phosphoroamidates and phosphonate analogs.

The invention also provides a method of inhibiting protein phosphatase 2A (PP2A) in a cell that includes administering to the interior of the cell a protein phosphatase-inhibiting amount of an antioxidant. In an alternative embodiment of this aspect of the invention, a method of decreasing the carboxymethylation status of the catalytic subunit of PP2A is provided that includes contacting a cell with a methyltransferase- or methylesterase-inhibiting amount of an antioxidant.

In one pathway that may not be exclusive, it has been discovered that antioxidants increase the cytotoxicity of antineoplastic drugs through a cascade of events that include: (i) increasing the level of cAMP, which causes the activation of protein kinase A, an enzyme which phosphorylates C/EBPβ, which on phosphorylation is then translocated from the cytosol to the nucleus of the cell wherein it mediates the induction of p21, which causes an arrest of cell growth; and (ii) preventing the dephosphorylation of C/EBPβ in the nucleus (and thus deactivation and delocalization) through the inhibition of PP2A. The inhibition of PP2A activity is caused by a decrease in methyltransferase activity, an enzyme which carboxymethylates the catalytic subunit of PP2A, which is involved in maintaining PP2A in an active form. Decreased methylcarboxylation results in decreased PP2A enzymatic dephosphorylation of C/EBPβ as a substrate. By simultaneously inducing the phosphorylation of C/EBPβ and inhibiting the dephosphorylation of C/EBPβ, antioxidants maintain C/EBPβ in an active state in the nucleus of the cell, which induces the continued expression of $p21^{WAF1/CIP1}$ and subsequent cell cycle arrest.

Based on this discovery, a method for the identification of therapeutically effective compounds for the treatment of abnormal cell proliferation is presented that includes assessing the compound's ability to increase the localization of the C/EBPβ protein in the nucleus of a cell. In an alternative embodiment, a method for the identification of therapeutically effective compounds for the treatment of abnormal cell proliferation is presented that includes assessing the compound's ability to increase the phosphorylation at $Ser^{299}$ of C/EBPβ. This method includes incubating a selected cell line with a test compound for a predetermined time (for example three hours) at 37 degrees C. followed by immunoprecipitation of C/EBPβ from the nuclear fraction. Tryptic digestion and thin layer chromatography is then carried out to confirm phosphorylation of C/EBPβ.

Based on the discoveries described in detail herein, one of ordinary skill will understand that the invention further includes, but is not limited to the following aspects.

(i) A method for the identification of therapeutically effective compounds by assessing the ability of the compound to alter the phosphorylation status of C/EBPβ at $Ser^{299}$. In this method, the test compound is included in a solution that contains at least phosphorylated C/EBPβ, a dimeric form of protein phosphatase 2A containing a and c subunits, methyltransferase and [methyl-$^3$H]S-adenosyl methionine.

(ii) A method for the identification of therapeutically effective compounds by assessing the ability of the compound to inhibit protein phosphatase 2a activity, using the method described in (1) or another protocol known or obvious to those skilled in the art.

(iii) A method for the identification of therapeutically effective compounds by assessing the ability of the compound to alter the carboxymethylation status of protein phosphatase 2a.

(iv) A method for the identification of therapeutically effective compounds by assessing the ability of the compound to alter the activity of methyltransferase.

(v) A peptide sequence of the form -X1-Arg-X2-Ser-X3 (Sequence ID No. 2) wherein X2 is the C/EBP-β amino acid at position 298, and X1 and X3 represent flanking peptide sequences with substantial homology to C/EBPβ.

(vi) A method for the enhancement the phosphorylation status and functionality of C/EBPβ induced by mediators including, but not limited to, cAMP dependent protein kinases, protein kinase C, ras-dependent MAP kinase and calcium-calmodulin dependent kinase, in an individual or animal in need of such treatment comprising the step of administering to said individual or animal a pharmacologically effective dose of an antioxidant that increases the nuclear residence time and functionality of C/EBPβ.

(vii) A method for the enhancement of the phosphorylation status and functionality of C/EBPβ induced by, but not limited to, cAMP dependent protein kinases, protein kinase C, ras-dependent MAP kinase and calcium-calmodulin dependent kinase, in an individual or animal in need of such treatment comprising the step of administering to said individual or animal a pharmacologically effective dose of an antioxidant.

(viii) A method for the treatment of a host, for example, an individual or animal, at risk for developing or exhibiting a neoplastic condition comprising the step of administering to said individual or animal a pharmacologically effective dose of an antioxidant.

(ix) A method for the treatment of individuals or animals at risk for developing a neoplastic condition that includes increasing the nuclear localization of C/EBPβ expression and function.

(x) A method for the treatment of individuals with a disorder of abnormal cell proliferation, including but not limited to benign and malignant tumors, that includes the step of administering to said individual or animal a pharmacologically effective dose of a therapeutic that increases the nuclear residence time of C/EPBβ, and wherein the therapeutic is either an antioxidant alone or a combination of an antioxidant and antineoplastic agent.

(xi) A method for the diagnosis and assessment of response to treatment of individuals with neoplastic and cell proliferative diseases through the measurement either alone or in combination, of C/EBPβ activation, phosphorylation and nuclear residence time of C/EBPβ, PP2A inhibition of carboxymethylation of the catalytic subunit of PP2A, and inhibition of methyltransferase or methylesterase activity.

II. Antioxidants

As used herein, the term antioxidant refers to a substance that prevents the oxidation of an oxidizable compound under physiological conditions. In one embodiment, a compound is considered an antioxidant for purposes of this disclosure if it reduces endogenous oxygen radicals in vitro. The antioxidant can be added to a cell extract under oxygenated conditions and the effect on an oxidizable compound evaluated. As nonlimiting examples, antioxidants scavenge oxygen, superoxide anions, hydrogen peroxide, superoxide radicals, lipooxide radicals, hydroxyl radicals, or bind to reactive metals to prevent oxidation damage to lipids, proteins, nucleic acids, etc. The term antioxidant includes, but is not limited to, the following classes of compounds.

A. Dithiocarbamates

Dithiocarbamates have been extensively described in patents and in scientific literature. Dithiocarbamates and related compounds have been reviewed extensively for example, by G. D. Thorn et al entitled "The Dithiocarbamates and Related Compounds," Elsevier, New York, 1962. U.S. Pat. Nos. 5,035,878 and 5,294,430 disclose that dithiocarbamates can reverse the damage to the blood-forming function of the bone marrow (myelosuppression) caused by treatment with antineoplastic agents. All of the pharmaceutically acceptable dithiocarbamates disclosed in these two patents that increase the nuclear localization of C/EBPβ are suitable for use in this invention, and are incorporated herein by reference.

Active Compounds

Dithiocarbamates are transition metal chelators clinically used for heavy metal intoxication. Baselt, R. C., F. W. J. Sunderman, et al. (1977), "Comparisons of antidotal efficacy of sodium diethyldithiocarbamate, D-penicillamine and triethylenetetramine upon acute toxicity of nickel carbonyl in rats." Res Commun Chem Pathol Pharmacol 18(4): 677–88; Menne, T. and K. Kaaber (1978), "Treatment of pompholyx due to nickel allergy with chelating agents." Contact Dermatitis 4(5): 289–90; Sunderman, F. W. (1978), "Clinical response to therapeutic agents in poisoning from mercury vapor" Ann Clin Lab Sci 8(4): 259–69; Sunderman, F. W. (1979), "Efficacy of sodium diethyldithiocarbamate (dithiocarb) in acute nickel carbonyl poisoning." Ann Clin Lab Sci 9(1): 1–10; Gale, G. R., A. B. Smith, et al. (1981), "Diethyldithiocarbamate in treatment of acute cadmium poisoning." Ann Clin Lab Sci 11(6): 476–83; Jones, M. M. and M. G. Cherian (1990), "The search for chelate antagonists for chronic cadmium intoxication." Toxicology 62(1): 1–25; Jones, S. G., M. A. Basinger, et al. (1982), "A comparison of diethyldithiocarbamate and EDTA as antidotes for acute cadmium intoxication." Res Commun Chem Pathol Pharmacol 38(2): 271–8; Pages, A., J. S. Casas, et al. (1985), "Dithiocarbamates in heavy metal poisoning: complexes of N,N-di(1-hydroxyethyl)dithiocarbamate with Zn(II), Cd(II), Hg(II), CH3Hg(II), and C6H5Hg(II).": J. Inorg Biochem 25(1): 35–42; Tandon, S. K., N. S. Hashmi, et al. (1990), "The lead-chelating effects of substituted dithiocarbamates." Biomed Environ Sci 3(3): 299–305.

Dithiocarbamates have also been used adjunctively in cis-platinum chemotherapy to prevent renal toxicity. Hacker, M. P., W. B. Ershler, et al. (1982). "Effect of disulfiram (tetraethylthiuram disulfide) and diethyldithiocarbamate on the bladder toxicity and antitumor activity of cyclophosphamide in mice" Cancer Res 42(11): 4490–4. Bodenner, 1986 #733; Saran, M. and Bors, W. (1990). "Radical reactions in vivo-an overview" Radiat. Environ. Biophys. 29(4):249–62.

A dithiocarbamate currently used in the treatment of alcohol abuse is disulfiram, a dimer of diethyldithiocarbamate. Disulfuram inhibits hepatic aldehyde dehydrogenase. Inoue, K., and Fukunaga, et al., (1982). "Effect of disulfiram and its reduced metabolite, diethyldithiocarbamate on aldehyde dehydrogenase of human erythrocytes" Life Sci 30(5): 419–24.

It has been reported that dithiocarbamates inhibit HIV virus replication, and also enhance the maturation of specific T cell subpopulations. This has led to clinical trials of diethyldithiocarbamate in AIDS patient populations. Reisinger, E., et al., (1990). "Inhibition of HIV progression by dithiocarb." *Lancet* 335: 679.

Dithiocarboxylates are compounds of the structure A—SC(S)—B, which are members of the general class of compounds known as thiol antioxidants, and are alternatively referred to as carbodithiols or carbodithiolates. It appears that the —SC(S)— moiety is essential for therapeutic activity, and that A and B can be any group that does not adversely affect the efficacy or toxicity of the compound.

In an alternative embodiment, one or both of the sulfur atoms in the dithiocarbamate is replaced with a selenium atom. The substitution of sulfur for selenium may decrease the toxicity of the molecule in certain cases, and may thus be better tolerated by the patient.

A and B can be selected by one of ordinary skill in the art to impart desired characteristics to the compound, including size, charge, toxicity, and degree of stability, (including stability in an acidic environment such as the stomach, or basic environment such as the intestinal tract). The selection of A and B will also have an important effect on the tissue-distribution and pharmacokinetics of the compound. The compounds are preferably eliminated by renal excretion.

An advantage in administering a dithiocarboxylate pharmaceutically is that it does not appear to be cleaved enzymatically in vivo by thioesterases, and thus may exhibit a prolonged half-life in vivo.

In a preferred embodiment, A is hydrogen or a pharmaceutically acceptable cation, including but not limited to sodium, potassium, calcium, magnesium, aluminum, zinc, bismuth, barium, copper, cobalt, nickel, or cadmium; a salt-forming organic acid, typically a carboxylic acid, including but not limited to acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, or polygalacturonic acid; or a cation formed from ammonia or other nitrogenous base, including but not limited to a nitrogenous heterocycle, or a moiety of the formula $NR^4R^5R^6R^7$, wherein $R^4$, $R^5$, $R^6$, and $R^7$ are independently hydrogen, $C_{1-6}$ linear, branched, or (in the case of $C_{4-6}$) cyclic alkyl, hydroxy-$(C_{1-6})$-alkyl (wherein one or more hydroxyl groups are located on any of the carbon atoms), or aryl, N,N-dibenzylethylene-diamine, D-glucosamine, choline, tetraethylammonium, or ethylenediamine.

In another embodiment, A can be a physiologically cleavable leaving group that can be cleaved in vivo from the molecule to which it is attached, and includes but is not limited to acyl (including acetyl, propionyl, and butyryl), alkyl, phosphate, sulfate or sulfonate.

In one embodiment, B is alkyl, alkenyl, alkynyl, alkaryl, aralkyl, haloalkyl, haloalkenyl, haloalkynyl, aryl, alkaryl, hydrogen, $C_{1-6}$ alkoxy-$C_{1-10}$ alkyl, $C_{1-6}$ alkylthio-$C_{1-10}$ alkyl, $NR^2R^3$, —$(CHOH)_nCH_2OH$, wherein n is 0, 1, 2, 3, 4, 5 or 6, —$(CH_2)_nCO_2R^1$, including alkylacetyl, alkylpropionyl, and alkylbutyryl, or hydroxy$(C_{1-6})$alkyl- (wherein one or more hydroxyl groups are located on any of the carbon atoms).

In another embodiment, B is $NR^2R^3$, wherein $R^2$ and $R^3$ are independently alkyl; —$(CHOH)_n(CH_2)_nOH$, wherein n is 0, 1, 2, 3, 4, 5 or 6; —$(CH_2)_nCO_2R^1$, —$(CH_2)_nCO_2R^4$; hydroxy$(C_{1-6})$alkyl-; alkenyl (including but not limited to vinyl, allyl, and $CH_3CH=CH-CH_2CH_2$); alkyl$(CO_2H)$, alkenyl$(CO_2H)$, alkynyl$(CO_2H)$, or aryl, wherein the aryl group can be substituted as described above, notably, for example, with a $NO_2$, $CH_3$, t-butyl, $CO_2H$, halo, or p-OH group; or $R^2$ and $R^3$ can together constitute a bridge such as —$(CH_2)_m$—, wherein m is 3, 4, 5, 6, 7, 8, 9 or 10, and wherein $R^4$ is alkyl, aryl, alkaryl, or aralkyl, including acetyl, propionyl, and butyryl.

In yet another embodiment, B can be a heterocyclic or alkylheterocyclic group. The heterocycle can be optionally partially or totally hydrogenated. Nonlimiting examples are those listed above, including phenazine, phenothiazine, pyridine and dihydropyridine.

In still another embodiment, B is the residue of a pharmaceutically-active compound or drug. The term drug, as used herein, refers to any substance used internally or externally as a medicine for the treatment, cure or prevention of a disease or disorder. The —C(S)SA group can be directly attached to the drug, or attached through any suitable linking moiety.

In another embodiment, the dithiocarbamate is an amino acid derivative of the structure $AO_2C-R^9-NR^{10}-C(S)SA$, wherein $R_9$ is a divalent B moiety, a linking moiety, or the internal residue of any of the naturally occurring amino acids (for example, $CH_3CH$ for alanine, $CH_2$ for glycine, $CH(CH_2)_4NH_2$ for lysine, etc.), and $R^{10}$ is hydrogen or lower alkyl.

B can also be a polymer to which one or more dithiocarbamate groups are attached, either directly, or through any suitable linking moiety. The dithiocarbamate is preferably released from the polymer under in vivo conditions over a suitable time period to provide a therapeutic benefit. In a preferred embodiment, the polymer itself is also degradable in vivo. The term biodegradable or bioerodible, as used herein, refers to a polymer that dissolves or degrades within a period that is acceptable in the desired application (usually in vivo therapy), usually less than five years, and preferably less than one year, on exposure to a physiological solution of pH 6–8 having a temperature of between 25 and 37° C. In a preferred embodiment, the polymer degrades in a period of between 1 hour and several weeks, according to the application.

A number of degradable polymers are known. Nonlimiting examples are peptides, proteins, nucleoproteins, lipoproteins, glycoproteins, synthetic and natural polypeptides and polyamino acids, including but not limited to polymers and copolymers of lysine, arginine, asparagine, aspartic acid, cysteine, cystine, glutamic acid, glutamine, hydroxylysine, serine, threonine, and tyrosine; polyorthoesters, including poly(a-hydroxy acids), for example, polylactic acid, polyglycolic acid, poly(lactide-co-glycolide), polyanhydrides, albumin or collagen, a polysaccharide containing sugar units such as lactose, and polycaprolactone. The polymer can be a random or block copolymer.

B can also be a group that enhances the water solubility of the dithiocarbamate, for example, -lower alkyl-O—$R^8$, wherein $R^8$ is —$PO_2(OH)^-M^+$ or $PO_3(M^+)_2$ wherein $M^+$ is a pharmaceutically acceptable cation; —$C(O)(CH_2)_2CO_2^- M^+$, or —$SO_3^{-M+}$; -lower alkylcarbonyl-lower alkyl; -carboxy lower alkyl; -lower alkylamino-lower alkyl; N,N-disubstituted amino lower alkyl-, wherein the substituents each independently represent lower alkyl; pyridyl-lower alkyl-; imidazolyl-lower alkyl-; imidazolyl-Y-lower alkyl wherein Y is thio or amino; morpholinyl-lower alkyl; pyrrolidinyl-lower alkyl; thiazolinyl-lower alkyl-; piperidinyl-lower alkyl; morpholinyl-lower hydroxyalkyl; N-pyrryl; piperazinyl-lower alkyl; N-substituted piperazinyl-lower alkyl, wherein the substituent is lower alkyl; triazolyl-lower alkyl; tetrazolyl-lower alkyl; tetrazolylamino-lower alkyl; or thiazolyl-lower alkyl.

In an alternative embodiment, a dimer such as B—C(S)S—SC(S)—B can be administered.

The term "alkyl," as used herein, unless otherwise specified, refers to a saturated straight, branched, or cyclic (in the case of $C_5$ or greater) hydrocarbon of $C_1$ to $C_{10}$ (or lower alkyl, i.e., $C_1$ to $C_5$), which specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted on any of the carbons with one or more moieties selected from the group consisting of hydroxyl, amino, or mono- or disubstituted amino, wherein the substituent group is independently alkyl, aryl, alkaryl or aralkyl; aryl, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term "alkenyl," as referred to herein, and unless otherwise specified, refers to a straight, branched, or cyclic hydrocarbon of $C_2$ to $C_{10}$ with at least one double bond.

The term "alkynyl," as referred to herein, and unless otherwise specified, refers to a $C_2$ to $C_{10}$ straight or branched hydrocarbon with at least one triple bond.

The term "aralkyl" refers to an aryl group with at least one alkyl substituent.

The term "alkaryl" refers to an alkyl group that has at least one aryl substituent.

The term "halo (alkyl, alkenyl, or alkynyl)" refers to an alkyl, alkenyl, or alkynyl group in which at least one of the hydrogens in the group has been replaced with a halogen atom.

The term "aryl," as used herein, and unless otherwise specified, refers to phenyl, biphenyl or napthyl, and preferably phenyl. The aryl group can be optionally substituted with one or more moieties selected from the group consisting of alkyl, hydroxyl, amino, alkylamino, arylamino, alkoxy, aryloxy, nitro, cyano, sulfonic acid, sulfate, phosphonic acid, phosphate, or phosphonate, $CO_2H$, or its pharmaceutically acceptable salt, $CO_2$(alkyl, aryl, alkaryl or aralkyl), or glucamine, either unprotected, or protected as necessary, as known to those skilled in the art, for example, as taught in Greene, et al., "Protective Groups in Organic Synthesis," John Wiley and Sons, Second Edition, 1991.

The term "alkoxy," as used herein, and unless otherwise specified, refers to a moiety of the structure —O-alkyl.

The term "acyl" as used herein, refers to a group of the formula C(O)R', wherein R' is an alkyl, aryl, alkaryl or aralkyl group.

The term "heterocyclic" as used herein, refers to an aromatic moiety that includes at least one sulfur, oxygen or nitrogen in the aromatic ring. Nonlimiting examples are phenazine, phenothiazine, furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, morpholinyl, carbozolyl, oxazolyl, thiazolyl, isothiazolyl, 1,2,4-thiadiazolyl, isooxazolyl, pyrrolyl, pyrazolyl, quinazolinyl, pyridazinyl, pyrazinyl, cinnolinyl, phthalazinyl, quinoxalinyl, xanthinyl, hypoxanthinyl, pteridinyl, 5-aza-cytidinyl, 5-azauracilyl, triazolopyridinyl, imidazolopyridinyl, pyrrolopyrimidinyl, pyrazolo-pyrimidinyl, adenine, $N^6$-alkylpurines, $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heterocyclic group can be optionally substituted as described above for aryl. The heterocyclic group can be partially or totally hydrogenated as desired. As a nonlimiting example, dihydropyridine can be used in place of pyridine. Functional oxygen and nitrogen groups on the heterocyclic base can be protected as necessary or desired during the reaction sequence. Suitable protecting groups are well known to those skilled in the art, and include trimethylsilyl, dimethylhexylsilyl, t-butyldimethylsilyl, and t-butyldiphenylsilyl, tritylmethyl, alkyl groups, acyl groups such as acetyl and propionyl, methylsulfonyl, and p-toluylsulfonyl.

The term "hydroxyalkyl," as used herein, refers to a $C_1$ to $C_6$ alkyl group in which at least one of the hydrogens attached to any of the carbon atoms is replaced with a hydroxy group.

The term "pharmaceutically acceptable derivative" refers to a derivative of the active compound that upon administration to the recipient, is capable of providing directly or indirectly, the parent compound, or that exhibits activity itself.

The term "pharmaceutically acceptable cation" refers to an organic or inorganic moiety that carries a positive charge and that can be administered in association with a pharmaceutical agent, for example, as a countercation in a salt. Pharmaceutically acceptable cations are known to those of skill in the art, and include but are not limited to sodium, potassium and quaternary amine.

The term "physiologically cleavable leaving group" refers to a moiety that can be cleaved in vivo from the molecule to which it is attached, and includes but is not limited to an organic or inorganic anion, a pharmaceutically acceptable cation, acyl (including but not limited to (alkyl)C(O), including acetyl, propionyl, and butyryl), alkyl, phosphate, sulfate and sulfonate.

The term "enantiomerically enriched composition or compound" refers to a composition or compound that includes at least 95%, and preferably at least 97, 98, 99, or 100% by weight of a single enantiomer of the compound.

The term "amino acid" includes synthetic and naturally occurring amino acids, including but not limited to, for example, alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl.

A "linking moiety" as used herein, is any divalent group that links two chemical residues, including but not limited to alkyl, alkenyl, alkynyl, aryl, polyalkyleneoxy (for example, —[(CH$_2$)$_n$O—]$_n$—), —C$_{1-6}$alkoxy-C$_{1-10}$alkyl-, —C$_{1-6}$alkylthio-C$_{1-10}$alkyl-, —NR$^3$—, and —(CHOH)$_n$CH$_2$OH, wherein n is independently 0, 1, 2, 3, 4, 5 or 6.

As explained in Chapter 2 of Thorn et al, the preparation of dithiocarbamates is very simple. The compounds of the formula RIR$_2$NCSSH or RIR$_2$NSSNa can be formed by reaction of carbon disulfide with a secondary amine, typically in alcoholic or aqueous solution. The usual practice is to carry out this reaction in the presence of NaOH, so that the sodium dithiocarbamate salt is formed. Thus, for example, sodium dimethyl dithiocarbamate is formed from CS$_2$NaOH and dimethylamine. See Thorn et al, page 14, and the references cited therein. Other typical dithiocarbamic compounds disclosed and characterized in Thorn et al include: N-methyl, N-ethyldithiocarbamates, hexamethyl-enedithiocarbamic acid, sodium di(beta-hydroxy-ethyl) dithiocarbamate, sodium N-methyl, N-cyclobutylmethyl dithiocarbamate, sodium N-allyl-N-cyclopropylmethyl-dithiocarbamate, cyclohexylamyldithiocarbamates, dibenzyl-dithiocarbamates, sodium dimethylene-dithiocarbamate, various pentamethylene dithiocarbamate salts, sodium pyrrolidine-N-carbodithioate, sodium piperidine-N-carbodithioate, sodium morpholine-N-carbo-dithioate, alpha-furfuryl dithiocarbamates and imidazoline dithiocarbamates.

B. Probucol and its Derivatives

Probucol is chemically related to the widely used food additives 2,[3]-tert-butyl-4-hydroxyanisole (BHA) and 2,6-di-tert-butyl-4-methyl phenol (BHT). Its full chemical name is 4,4'-(isopropylidenedithio)bis(2,6-di-tert-butylphenol). U.S. Pat. No. 5,262,439 to Parthasarathy, incorporated herein by reference, discloses soluble analogs of probucol in which one or both of the hydroxyl groups are replaced with ester groups that impart water solubility to the compound. In one embodiment, the soluble derivative is selected from the group consisting of a mono- or di- succinic acid ester, glutaric acid ester, adipic acid ester, suberic acid ester, sebacic acid ester, azelaic acid or maleic acid ester of probucol. In another embodiment, the probucol derivative is a mono- or di- ester in which the ester contains an alkyl or alkenyl group that contains functionality selected from the group consisting of a carboxylic acid group. Any of the compounds described in the '439 patent can be used in this invention.

U.S. Pat. No. 5,155,250, also incorporated herein by reference, discloses that 2,6-dialkyl-4-silylphenols are anti-atherosclerotic agents. The same compounds are disclosed as serum cholesterol lowering agents in PCT Publication No. WO 95/15760, published on Jun. 15, 1995. U.S. Pat. No. 5,608,095, incorporated by reference, discloses that alkylated-4-silyl-phenols inhibit the peroxidation of LDL, lower plasma cholesterol, and inhibit the expression of VCAM-1, and thus are useful in the treatment of atherosclerosis. Any of these compounds can also be used in this invention.

C. N-Acetyl Cysteine and its Derivatives

Cysteine is an amino acid with one chiral carbon atom. It exists as an L-enantiomer, a D-enantiomer or a racemic mixture of the L- and D-enantiomers. The L-enantiomer is the naturally occurring configuration.

N-acetylcysteine (acetamido-mercaptopropionic acid, NAC) is the N-acetylated derivative of cysteine. It also exists as an L-enantiomer, a D-enantiomer, an enantiomerically enriched composition of one of the enantiomers, or a racemic mixture of the L and D enantiomers. The term "enantiomerically enriched composition or compound" refers to a composition or compound that includes at least 95%, and preferably, at least 97% by weight of a single enantiomer of the compound. Any of these forms of NAC can be delivered as an antioxidant in the present invention. In one embodiment, a single isomer of a thioester or thioether of NAC or its salt, and most preferably, the naturally occurring L-enantiomer, is used in the treatment process.

N-acetylcysteine exhibits antioxidant activity (Smilkstein, Knapp, Kulig and Rumack, *N. Engl. J Med*. 1988, Vol. 319, pp. 1557–62; Knight, K. R., MacPhadyen, K., Lepore, D. A., Kuwata, N., Eadie, P. A., O'Brien, B. *Clinical Sci*., 1991, Vol. 81, pp. 31–36; Ellis, E. F., Dodson, L. Y., Police, R. J., *J Neurosurg*., 1991, Vol. 75, pp. 774–779). The sulfhydryl functional group is a well characterized, highly reactive free radical scavenger. N-acetylcysteine is known to promote the formation of glutathione (a tri-peptide, also known as g-glutamylcysteinylglycine), which is important in maintaining cellular constituents in the reduced state (Berggren, M., Dawson, J., Moldeus, P. *FEBS Lett*., 1984, Vol. 176, pp. 189–192). The formation of glutathione may enhance the activity of glutathione peroxidase, an enzyme which inactivates hydrogen peroxide, a known precursor to hydroxyl radicals (Lalitha, T., Kerem, D., Yanni, S., *Pharmacology and Toxicology*, 1990, Vol.66, pp. 56–61)

N-acetylcysteine exhibits low toxicity in vivo, and is significantly less toxic than deprenyl (for example, the $LD_{50}$ in rats has been measured at 1140 and 81 mg/kg intravenously, for N-acetylcysteine and deprenyl, respectively).

N-acetyl cysteine and derivatives thereof are described, for example, in WO/95/26719. Any of the derivatives described in this publication can be used in accordance with this invention.

D. Scavengers of Peroxides

Scavengers of peroxides include but are not limited to catalase and pyruvate.

E. Thiols

Thiols include but are not limited to dithiothreitol and 2-mercaptoethanol.

F. Antioxidants which are Inhibitors of Lipid Peroxidation

Antioxidants which are inhibitors of lipid peroxidation, include but are not limited to Trolox™, BHA, BHT, aminosteroid antioxidants, tocopherol and its analogs, and lazaroids.

G. Dietary Antioxidants

Dietary antioxidants, include but are not limited to antioxidant vitamins (vitamin C or E or synthetic or natural prodrugs or analogs thereof), either alone or in combination with each other, flavanoids, phenolic compounds, caratenoids, and alpha lipoic acid.

H. Inhibitors of Lipoxygenases and Cyclooxygenases

Inhibitors of lipoxygenases and cyclooxygenases, include but are not limited to nonsteriodal antinflammatory drugs, COX-2 inhibitors, aspirin-based compounds, and quercetin.

I. Antioxidants Manufactured by the Body

Antioxidants manufactured by the body, include but are not limited to ubiquinols and thiol antioxidants, such as, and including glutathione, Se, and lipoic acid J. Synthetic Phenolic Antioxidants Synthetic phenolic antioxidants include but are not limited to inducers of Phase I and II drug-metabolizing enzymes.

III. Antineoplastic Agents

The term "antineoplastic agents," as used herein, refers to any substance that decreases abnormal cell proliferation. Antineoplastic agents have been described extensively in a number of texts, including Martindale, The *Extra Pharmacopoeia*, 31$^{st}$ Edition, Royal Pharmaceutical Society (1996).

Antineoplastic agents include:

(i) antifolates;

(ii) antimetabolites (including purine antimetabolites, cytarabine, fudarabine, floxuridine, 6-mercaptopurine, methotrexate, 5-fluoropyrimidine, including 5-fluorouracil, cytidine analogues such as β-L-1,3-dioxolanyl cytidine and 6-thioguanine);

(iii) hydroxyurea;
(iv) mitotic inhibitors (including CPT-11, Etoposide (VP-21)), taxol and vincristine;
(v) alkylating agents (including but not limited to busulfan, chlorambucil, cyclophosphamide, ifofamide, mechlorethamine, melphalan and thiotepa);
(vi) nonclassical alkylating agents, platinum containing compounds, bleomycin, anti-tumor antibiotics, anthracycline, anthracenedione, topoisomerase 11 inhibitors, hormonal agents (including but not limited to corticosteroids (dexamethasone, prednisone and methylprednisone); and
(v) androgens such as fluoxymesterone and methyltestosterone, estrogens such as diethylstilbesterol, antiestrogens such as tamoxifen, LHRH analogues such as leuprolide, antiandrogens such as flutamide, aminoglutethimide, megestrol acetate, and medroxyprogesterone), asparaginase, carmustine, lomustine, hexamethyl-melamine, dacarbazine, mitotane, streptozocin, cisplatin, carboplatin, levamasole, and leucovorin.

A more comprehensive list of antineoplastic agents includes Aceglatone; Aclarubicin; Altretamine; Aminoglutethimide; 5-Aminogleavulinic Acid; Amsacrine; Anastrozole; Ancitabine Hydrochloride; 17-1A Antibody; Antilymphocyte Immunoglobulins; Antineoplaston A10; Asparaginase; Pegaspargase; Azacitidine; Azathioprine; Batimastat; Benzoporphyrin Derivative; Bicalutamide; Bisantrene Hydrochloride; Bleomycin Sulphate; Brequinar Sodium; Broxuridine; Busulphan; Campath-IH; Caracemide; Carbetimer; Carboplatin; Carboquone; Carmofur; Carmustine; Chlorambucil; Chlorozotocin; Chromomycin; Cisplatin; Cladribine; Corynebacterium parvum; Cyclophosphamide; Cyclosporin; Cytarabine; Dacarbazine; Dactinomycin; Daunorubicin Hydrochloride; Decitabine; Diaziquone; Dichlorodiethylsulphide; Didemnin B.; Docetaxel; Doxifluridine; Doxorubicin Hychloride; Droloxifene; Echinomycin; Edatrexate; Elliptinium; Elmustine; Enloplatin; Enocitabine; Epirubicin Hydrochloride; Estramustine Sodium Phosphate; Etanidazole; Ethoglucid; Etoposide; Fadrozole Hydrochloride; Fazarabine; Fenretinide; Floxuridine; Fludarabine Phosphate; Fluorouracil; Flutamide; Formestane; Fotemustine; Gallium Nitrate; Gencitabine; Gusperimus; Homoharringtonine; Hydroxyurea; Idarubicin Hydrochloride; Ifosfamide; Ilmofosine; Improsulfan Tosylate; Inolimomab; Interleukin-2; Irinotecan; JM-216; Letrozole; Lithium Gamolenate; Lobaplatin; Lomustine; Lonidamine; Mafosfamide; Melphalan; Menogaril; Mercaptopurine; Methotrexate; Methotrexate Sodium; Miboplatin; Miltefosine; Misonidazole; Mitobronitol; Mitoguazone Dihydrochloride; Mitolactol; Mitomycin; Mitotane; Mitozanetrone Hydrochloride; Mizoribine; Mopidamol; Multialchilpeptide; Muromonab-CD3; Mustine Hydrochloride; Mycophenolic Acid; Mycophenolate Mofetil; Nedaplatin; Nilutamide; Nimustine Hydrochloride; Oxaliplatin; Paclitaxel; PCNU; Penostatin; Peplomycin Sulphate; Pipobroman; Pirarubicin; Piritrexim Isethionate; Piroxantrone Hydrochloride; Plicamycin; porfimer Sodium; Prednimustine; Procarbazine Hydrochloride; Raltitrexed; Ranimustine; Razoxane; Rogletimide; Roquinimex; Sebriplatin; Semustine; Sirolimus; Sizofiran; Sobuzoxane; Sodium Bromebrate; Sparfosic Acid; Sparfosate Sodium; Sreptozocin; Sulofenur; Tacrolimus; Tamoxifen; Tegafur; Teloxantrone Hydrochloride; Temozolomide; Teniposide; Testolactone; Tetrasodium Meso-tetraphenylporphinesulphonate; Thioguanine; Thioinosine; Thiotepa; Topotecan; Toremifene; Treosulfan; Trimetrexate; Trofosfamide; Tumor Necrosis Factor; Ubenimex; Uramustine; Vinblastine Sulphate; Vincristine Sulphate; Vindesine Sulphate; Vinorelbine Tartrate; Vorozole; Zinostatin; Zolimomab Aritox; and Zorubicin Hydrochloride.

IV. Abnormal Cell Hyperproliferative Conditions

Antioxidants can be used to increase the cytotoxicity of antineoplastic agents to disorders of abnormal cellular proliferation, including, but not limited to:
(i) benign tumors, including, but not limited to papilloma, adenoma, firoma, chondroma, osteoma, lipoma, hemangioma, lymphangioma, leiomyoma, rhabdomyoma, meningioma, neuroma, ganglioneuroma, nevus, pheochromocytoma, neurilemona, fibroadenoma, teratoma, hydatidiform mole, granuosa-theca, Brenner tumor, arrhenoblastoma, hilar cell tumor, sex cord mesenchyme, interstitial cell tumor and thyoma;
(ii) malignant tumors (cancer), including but not limited to carcinoma, including renal cell carcinoma, prostatic adenocarcinoma, bladder carcinoma,and adenocarcinoma, fibrosarcoma, chondrosarcoma, osteosarcoma, liposarcoma, hemangiosarcoma, lymphangiosarcoma, leiomyosarcoma, rhabdomyosarcoma, myelocytic leukemia, erythroleukemia, multiple myeloma, glioma, meningeal sarcoma, thyoma, cystosarcoma phyllodes, nephroblastoma, teratoma choriocarcinoma, cutaneous T-cell lymphoma (CTCL), cutaneous tumors primary to the skin (for example, basal cell carcinoma, squamous cell carcinoma, melanoma, and Bowen's disease), breast and other tumors infiltrating the skin, Kaposi's sarcoma, and premalignant and malignant diseases of mucosal tissues, including oral, bladder, and rectal diseases, central nervous system tumors (glioblastomas), meningiomas, and astrocytomas; and
(iii) hyperproliferative and preneoplastic lesions, including mycosis fungoides, psoriasis, dermatomyositis, rheumatoid arthritis, viruses (for example, warts, herpes simplex, and condyloma acuminata), molluscum contagiosum, remalignant and malignant diseases of the female genital tract (cervix, vagina, and vulva).

Of these, particular conditions that can be treated using this method include colorectal cancer, ovarian cancer, bone cancer, renal cancer, breast cancer, gastric cancer, pancreatic cancer, melanoma, hematopoietic tumors such as lymphoma, leukemia, plasma cell dyscrasias, and multiple meyloma and amylodosis.

Antioxidants can also be used in combination with antineoplastic agents to treat cardiovascular proliferative disease such as post-angioplasty restenosis and atherosclerosis.

V. Pharmaceutical Compositions

A host, including mammals, and specifically humans, suffering from any of the above-described conditions can be treated by the topical or systemic administration to the patient of an effective amount of an antioxidant, optionally in combination with an antineoplastic agent, in the presence of a pharmaceutically acceptable carrier or diluent. The antioxidant can be administered prior to, in combination with, or following treatment with an antineoplastic agent when used to increase the cytotoxic effect of the antineoplstic agent. Methods and dosages for the administration of antineoplastic agents are known to those skilled in the art, and are described in a number of texts, including the *The Physician's Desk Reference*, Martindale's *The Extra Pharmacopeia*, and Goodman & Gilman's *The Pharmacological Basis of Therapeutics*, or can be easily determined using standard methods.

The antioxidant can be administered subcutaneously, intravenously, intraperitoneally, intramuscularly, parenterally, orally, submucosally, by inhalation, transdermally via a slow release patch, or topically, in an effective dosage range to treat the target condition. Typical systemic dosages for all of the herein described conditions are those ranging from 0.01 mg/kg to 500 mg/kg of body weight per day as a single daily dose or divided daily doses. Typical dosages for topical application are those ranging from 0.001 to 100% by weight of the active compound.

The compound is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compound in vivo in the absence of serious toxic effects.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound for systemic delivery is oral. Oral compositions will generally include an inert diluent or an edible carrier. They may be enclosed in gelatin capsules or compressed into tablets. For the purpose of oral therapeutic administration, the active compound, can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound or its salts can be administered as a component of an elixir, suspension, syrup, wafer, lozenge, chewing gum or the like. A syrup may contain, in addition to the active compounds, sucrose as a sweetening agent and certain preservatives, dyes and colorings and flavors.

The compound can also be mixed with other active materials that do not impair the desired action, or with materials that supplement the desired action, such as antibiotics, antifungals, antiinflammatories, antivirals, or other immunosuppressive agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

If administered intravenously, preferred carriers are physiological saline,bacteriostatic water, Cremophor EL™ (BASF, Parsippany, N.J.) or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene. A number of solutions and ointments are commercially available, especially for ophthalmic applications.

ILLUSTRATIVE EXAMPLES

The following examples are provided for the purpose of illustrating various embodiments of the invention and are not intended to limit the scope of the present invention.

Example 1

HCT 116 and HCT 15 human CRC cells were obtained from the American type Culture Collection. $p21^{WAF1/}$ $CIP1$-/- cancer cells generated from HCT 116 cells by T. Waldman were provided by J. Pietenpol (Vanderbilt University, Tenn.) and HPV E6-transfected HCT 116 by W. S. El-Deiry (University of Pennsylvania, Pa.) [W. S. El-Deiry et al., Cell 75, 817 (1993)]. All cancer cell lines used in these studies were grown in Dulbecco's modified Eagle's medium (DMEM) (GIBCO BRL) with high glucose and supplemented with 10% heat-activated fetal bovine serum (FBS), non-essential amino acids, L-glutamine, and penicillin G Sodium (100 U/ml) and streptomycin sulfate (100 mg/ml) at 37° C. in 5% $CO_2$ in air.

To determine the effect of pyrrolidinedithiocarbamate (Sigma Chemical Co., Ma.), a vitamin E analogue (6-hydroxy-2.5,7,8-tetramethylchroman-2-carboxylic acid: vit (E) (Aldrich), 5-FU (Hoffmann-LaRoche Inc. Nutley, N.J.) or doxorubicin (Sigma) on anchorage-independent growth, HCT 15 and HCT 116 cells were plated at $10 \times 10^3$ cells/35 mm plate in DMEM supplemented with 1% FBS and 0.4% agar along with the factor to be tested. The number of colonies was quantified under 10 days using the Omnicon image analyzer. Colonies greater than 50 microns in diameter (approximately 50 cells) were scored as positive after 10 days. Preliminary studies indicated that pyrrolidinedithiocarbamate and vitamin E had no significant effect on CRC cell plating efficiency, at concentrations between 25–200 µM and 0.1–10 mM, respectively. Higher concentrations resulted in non-specific cytotoxicity.

Example 2

DNA Content of nuclei was determined as described [I. G. Nicoletti et al., J Immunol. Methods. 139, 271 (1991)] by lysing plasma membranes, staining nuclear DNA with propidium iodide (50 mg/ml), and quantitating the relative DNA content of nuclei using the Becton Dickinson FACSORT fluorescence-activated cell sorter. The proportion of nuclei in each phase of the cell cycle was determined using MODFIT-DNA analysis software. Detection of apoptotic cells either by fluorescence microscopy or by flow cytometry was performed using the ApopTag Plus In Situ Apoptosis Detection Kit (Oncor, Gaithersburg, Md.) as described in the manufacturer's protocol. Briefly, gigoxygenin-labeled nucleotides were added to free 3'OH groups of DNA produced by DNA fragmentation during apoptosis by terminal deoxynucleotidyl transferase (TdT). Digoxygenin was detected by a FTC-conjugated anti-digoxygenin antibody. Analysis was carried out using the fluorescence-activated cell sorter and FITC staining visualized using a fluorescence microscope (Zeiss).

Example 3

Intracellular $H_2O_2$ levels were analyzed by flow cytometry using dihydrorhodamine 1234 (DHR) as a specific fluorescent dye probe [G. Rothe, A. Emmendorffer, A. Oser, J. Roesler, G. Valet, J Immun. Methods 138, 133 (1991); J. A. Royall, H. Ischiropoulos, Arch. Biochem. Biophysics 302, 348 (1993)]. CRC cells were grown in DMEM containing 1 mM DHR and pyrrolidinedithiocarbamate (70 µM) or vit E (3 mM) for up to 24 hours. Following trypinization, trypsin activity was quenched with 2% FBS in phosphate buffered saline and cells fixed in 1% paraformaldehyde (Sigma). Cellular rhodamine 123 fluorescence intensity of $1 \times 10^4$ cells was measured for each sample using a Becton-Dickinson FACS Vantage flow cytometer with the excitation source at 488 nm and emission wave length of 580 nm. Histograms were analyzed with the software program PC-Lysis (Becton Dickenson). Background fluorescence from blank wells was subtracted from each reading.

Example 4

Male athymic Balb/c nu/nu mice were obtained from the Harlan Sprague-Dawley Company at 4–6 weeks of age and were quarantined for at least 2 weeks before the study. Animal experiments were carried out in accordance with both institutional and federal animal care regulations. HCT 116 and HCT 15 CRC cell lines were grown in DMEM supplemented with 10% FBS as described above. Cells were harvested through two consecutive trypsinizations, centrifuged at 300 g for 5 minutes, washed twice, and resuspended in sterile phosphate buffered saline. One $\times 10^6$ cells in 0.2 ml were injected subcutaneously between the scapula of 7- to 10-week-old male nude mice.

Example 5

Tumor volumes were estimated weekly by measuring the maximal length, width, and height. Once tumors reached a mean size of 120 to 150 mm$^3$, animals received either weekly i.p. injections of pyrrolidinedithiocarbamate (70 µM) or vitamin E (3 mM), 5-FU (40 mg/kg) or saline, or a combination of pyrrolidinedithiocarbamate or vitamin E and 5-FU or 6 weeks. In cross-over experiments, animals received the above treatments for three weeks (with the exception of vitamin E), and then were crossed-over to either the combination treatment of pyrrolidinedithiocarbamate and 5-FU (saline, pyrrolidinedithiocarbamate or 5-FU alone) or discontinued treatment pyrrolidinedithiocarbamate and 5-FU) for the remaining three weeks of the experiment. In preliminary experiments, a series of single doses of pyrrolidinedithio-carbamate, vitamin E or 5-FU was administered over a 30 day period to establish $LD_{50}$ and effective route of administration (data not shown). Tumor volumes were recorded weekly until termination of the study.

Example 6

Tumor tissues were fixed overnight in 4% (v/v) paraformaldehyde and embedded in paraffin according to standard histological procedures. BrDU staining was performed as described [Holmgren, et al., Nature Med. 1, 149 (1955)]. TdT labeling of fragmented DNA (TUNEL) was performed as described. The proliferative index (BrDU) and the apoptotic index (TUNEL) were estimated by the percentage of cells scored under a microscope at 200-fold magnification. The proliferative indices for HCT 116 and HCT 15-derived tumors (irrespective of treatments) were 53.1±5.2 and 63.1±7.2, respectively.

Example 7

For Western blot analysis, cells were lysed in 50 mM Tris-Cl. pH7.4, 300 mM NaCl, 2 mM EDTA, 0.5% Nonidet-40, 05 mM phenylmethysulfonyl fluoride aprotinin (1 µg/ml), pepstatin (µg/ml), and leupeptin (2 µg/ml). One hundred mg of extract (as determined by Bradford analysis) was applied to 12% SDS-PAGE gels and transferred to 0.2 µM pore nitrocellulose membranes (Schleicher and Schuell). Blots were probed with antibodies raised against p21 WAF1/CIPI, p53, p27 or C/EBPβ (Santa Cruz) at a final concentration of 0.1 µg/ml. After washing, blots were incubated with donkey-anti-rabbit or goat-anti-mouse IgG-horseradish peroxidase conjugates, and developed using Enhanced Chemiluminescence (Amersham, Arlington Heights, Ill.).

Example 8

RNA was extracted as described [M. Schwab, K. Alitalo, H. E. Varmus, J. M. Bishop, *Nature (Lond.)* 303, 497 (1983)]. Poly (A)+ mRNA was separated by electrophoresis through 1% (w/v) agaroseformaldehyde gels, and northern blotting was performed as previously described (Coffey, et al., *Cancer Res.* 47, 4590 (1987)]. A human p21$^{WAF1/CIP1}$ cDNA probe was provided by B. Vogelstein (John Hopkins Oncology Center, Baltimore, Md.) and labeled with [$^{32}$P] dCTP by the random primer extension method. Hybridization and post-hybridization washes were carried out at 43° C. IB15 was used as a control for equivalent loading and transfer [P. E. Danielson, et al., *DNA* 7, 261 (1988)].

Example 9

The human p21$^{WAF1/CIP1}$ promoter construct (WWP-luc) was provided by B. Vogelstein [W. El-Deiry, et al., *Cell* 75, 817 (1993)]. CRC cell lines were grown to 50% confluence prior to transfection with CELLFECTIN per manufacturer's instructions (GIBCO BRL). For all luciferase assays, total DNA transfected was kept constant with addition of pBSKII+ or pCMV-basic. All pCMV-C/EBP expression vectors were provided by L. Sealy (Vanderbilt University, TN). pCMV-CAT was transfected as an internal control for gene expression. At 12 hours post-transfection, selected cells were treated with 70 µM pyrrolidinedithiocarbamate. After 24 hours of treatment, cell lysates were prepared and luciferase activity was assayed as described [A. Misra-Press, C. S. Rim, H. Yao, M. S. Roberson, P. J. S. Stork, *J Biol. Chem.* 270, 14587 (1995)]. Luciferase activity was normalized to CAT activity, and results were reported as fold activation above basal levels.

Example 10

The 2,4 kilobase pair genomic fragment containing the p21$^{WAF1/CIP1}$ cDNA start site at its 3' end was subcloned into the Hind III site of the luciferase reporter vector, pGL2-basic (Promega). p21$^{WAF1/CIP1}$ deletion mutants (D2198 to D1138) were generated by PCR using internal p21$^{WAF1/CIP1}$ primers designed against the published p21$^{WAF1/CIP1}$ promoter sequence (GenBank). In each case, PCR products were subcloned into pGL2-basic and the sequences verified by double-stranded DNA sequencing. Mutagenesis of the NF_IL6 recognition site was performed using the Muta-Gene M13 In vitro mutagenesis kit (Bio-Rad, Hercules, Calif.).

The presence of the desired TT to AA base pair change was verified by DNA sequencing.

Example 11

Complementary oligonucleotides corresponding to bases −1884 through −1904 in the wild type and the NF_IL6 mutant p21$^{WAF1/CIP1}$ promoter sequence were synthesized {wild type: GTACTTAAGAAATATTGAAT (Sequence ID No. 3) and ATTCAATATTTCTTAAGTAC (Sequence ID No. 4); mutant: GTACAAAAGAAATATTGAAT (Sequence ID No. 3) and ATCAATATTTCTTTTGTAC (Sequence ID No. 3)}. Two hundred ng of each oligo was end-labeled with 200 µCi γ-$^{32}$P-labeled ATP and T4 polynucleotide kinase. The resulting end-labeled oligos were then annealed and gel purified. Preparation of nuclear extract from CRC cells treated with antioxidants and the conditions for electrophoretic shift mobility assays (EMSA) were as described [Kailoff, et al., *Science* 253, 786 (1991)]. When antisera were added, nuclear extracts and 2 µL of C/EBP α, β, or δ polyclonal antibody (Santa Cruz) were incubated for 10 minutes at room temperature before the addition of the radiolabeled probe.

Example 12

Figure 1A:
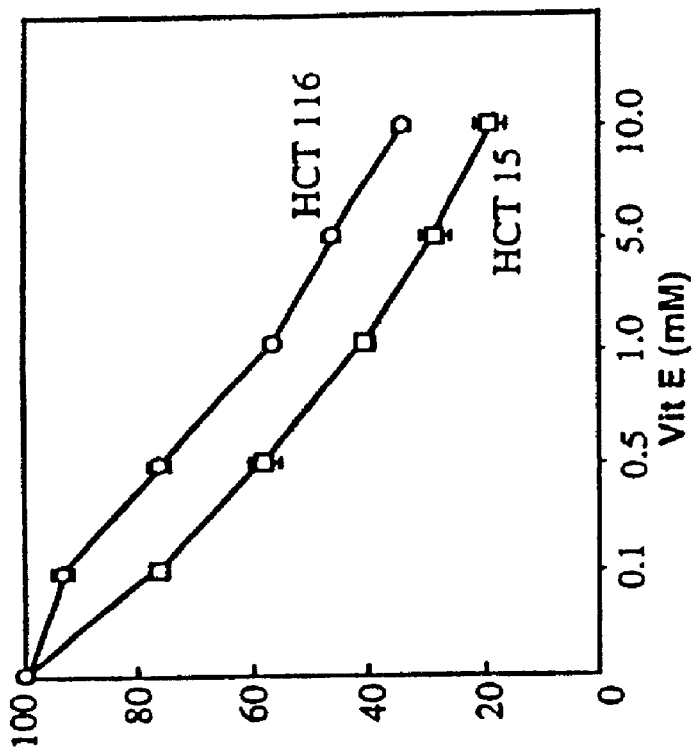
FIG. 1A is a graph of the concentration of PDTC versus soft-agar forming units×10$^6$ HCT 15 and HCT 116 cells (as a percent of control). The graph shows that pyrrolidinedithiocarbamate (PDTC) and vitamin E inhibit anchorage-independent growth in vitro. Soft-agar colony formation was measured by seeding HCT 116 or HCT 15 cells in soft agar supplemented with either medium alone (control), or increasing concentrations of pyrrolidinedithiocarbamate (25–200 μM) or vitamin E (0.1–10 mM). Colonies were scored at the end of 10 days incubation at 37° C. Values are representative of three experiments carried out in quadruplicate.
Figure 1A:
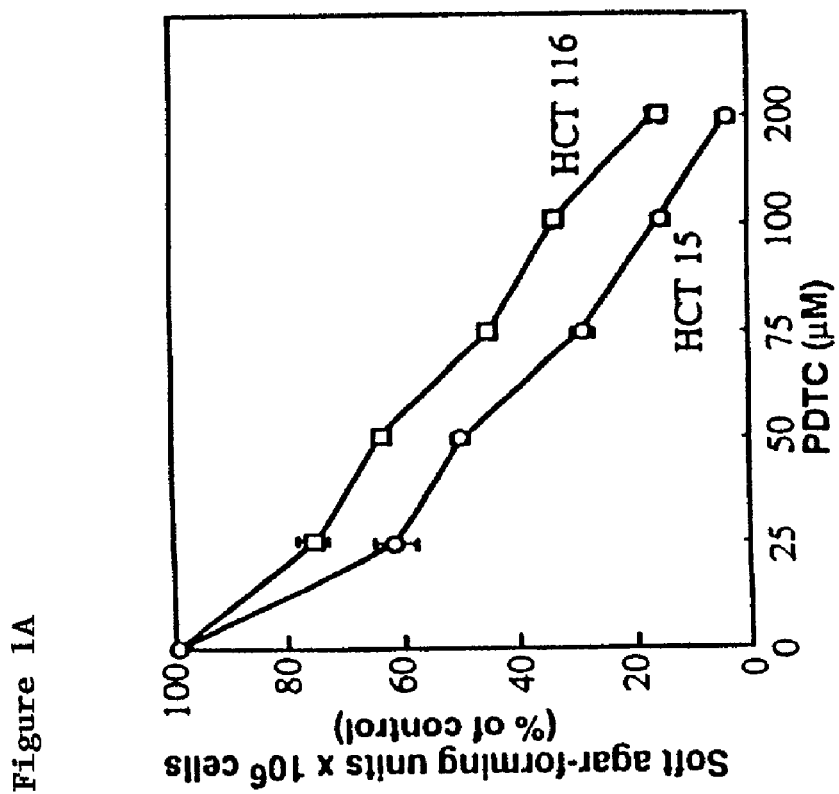

Two human colorectal cancer cell lines, HCT 116 (wild type p53) and HCT 15 (mutant p53), were treated with increasing amounts of either pyrrolidinedithiocarbamate or vitamin E in a soft agar ex vivo model of tumorigenicity. Both pyrrolidinedithiocarbamate and vitamin E caused a dose-dependent reduction in anchorage-independent growth of HCT 116 and HCT 15 cells (FIG. 1A). This analysis was extended to a variety of tumor cell lines derived from the colon (HCA-7, Difi, RKO, SW620), breast (MCF-7, MDA-MB231), and stomach (Hs 746T). At these concentrations, both antioxidants were effective in inhibiting anchorage-independent growth of all tumor cell lines tested, independent of their p53 status (Difi, RKO, data not shown).

Figure 1B:
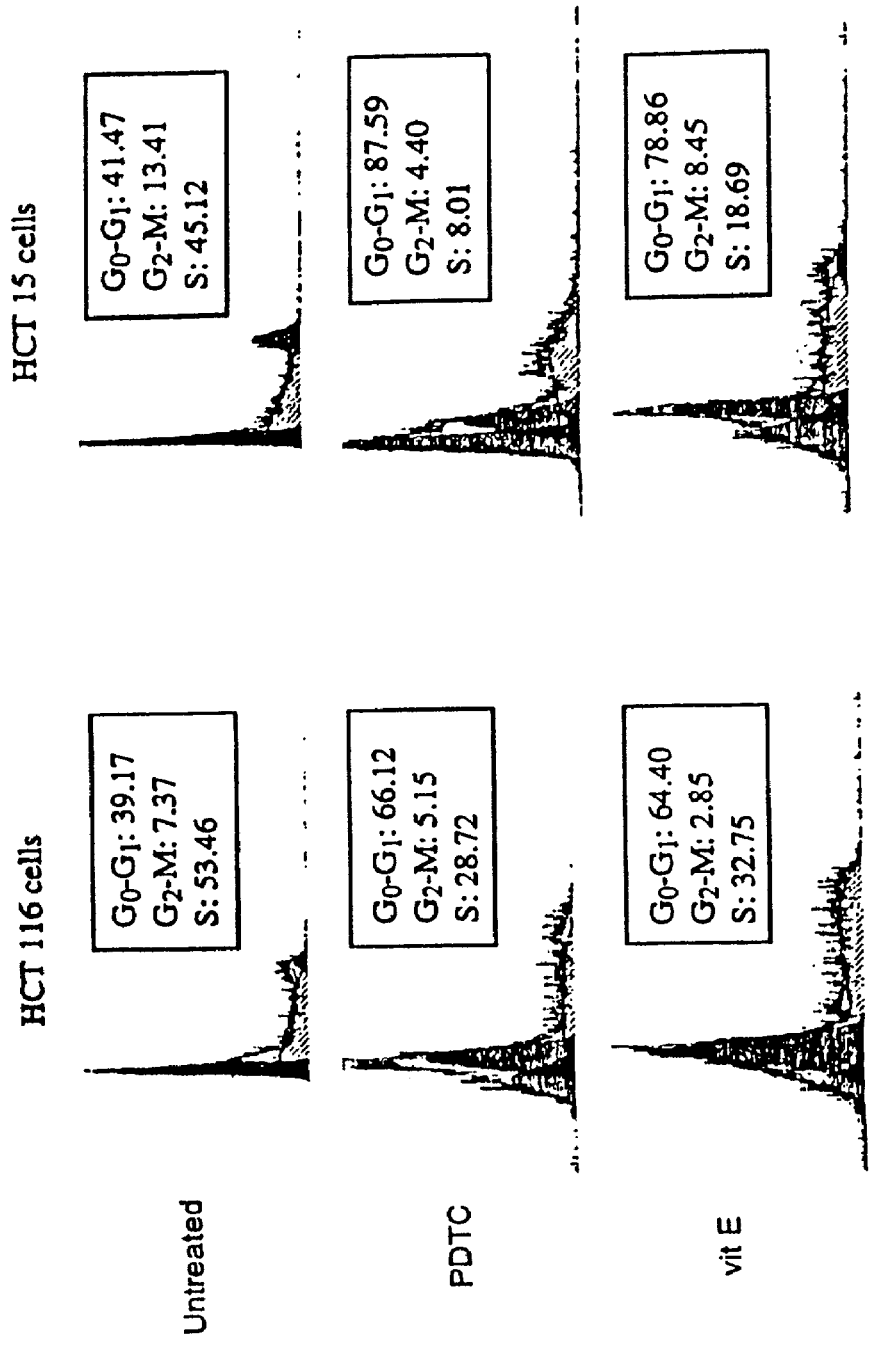
FIG. 1B is a series of flow cytometric analyses that indicate that antioxidants induce $G_1$ cell cycle arrest and apoptosis in CRC cells. Unsynchronized HCT 116 or HCT 15 cells are grown either in the presence or absence of pyrrolidinedithiocarbamate (70 μM) or vitamin E (3 mM). Twenty-four hours following antioxidant exposure, cells were harvested and flow cytometric analysis performed.

Treatment of HCT 116 or HCT 15 CRC cells with either pyrrolidinedithiocarbamate (70 µM) or vitamin E (3 mM) for 24 hours, followed by propidium iodide staining of cells and subsequent flow cytometric analysis, revealed that both compounds induced a significant accumulation of cells in the $G_1$ peak, suggesting that the observed growth inhibitory effects of pyrrolidinedithiocarbamate or vitamin E in soft agar were due to cell cycle arrest and/or apoptosis (FIG. 1B). To determine whether these cell cycle perturbations could be correlated with the antioxidant properties of these compounds, both the intracellular redox status (by endogenous $H_2O_2$ levels) and the percentage of cells undergoing $G_1$ cell cycle arrest or apoptosis (by flow 25cytrometric analysis) were quantified over a 24 hour period in antioxidant-treated cells.

Figure 1C:
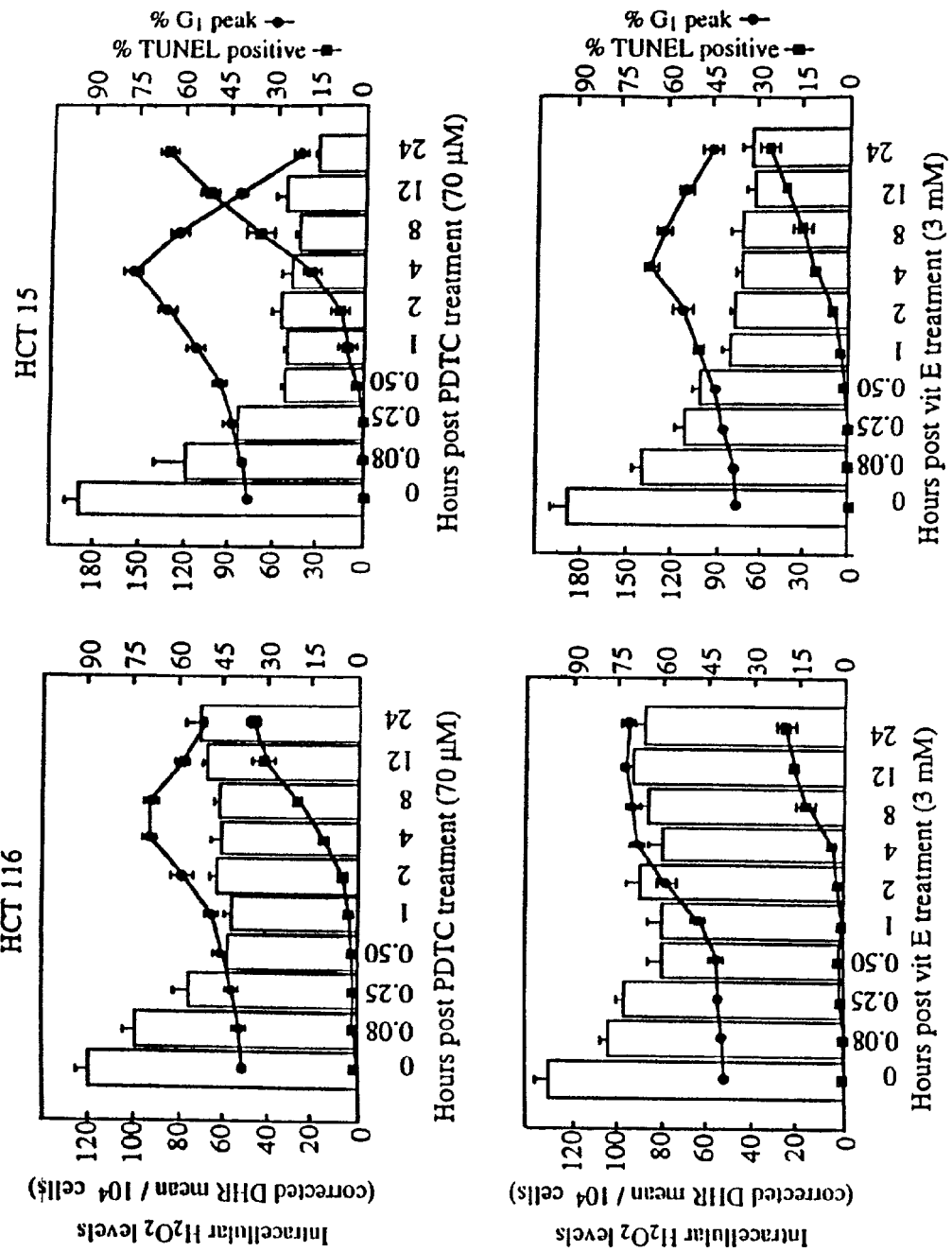
FIG. 1C is a bar graph of the hours after test compound treatment versus intracellular $H_2O_2$ levels.
Figure 1D:
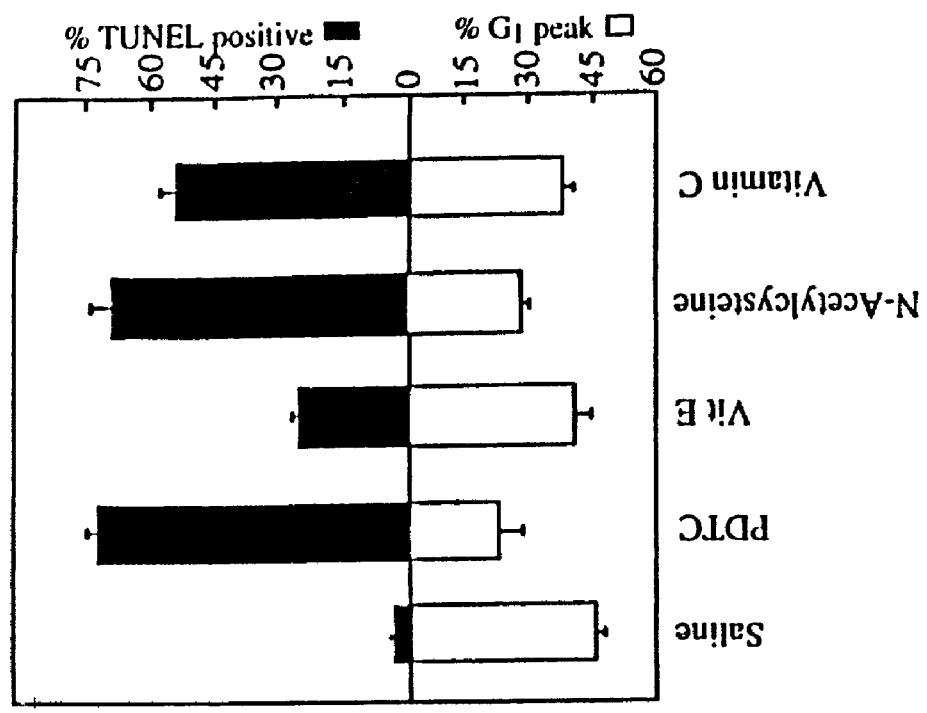
FIG. 1D shows the effect of N-acetylcysteine, vitamin C and catalase on endogenous $H_2O_2$ levels and cell cycle progression. HCT 15 cells were incubated with pyrrolidinedithiocarbamate (70 μM), vitamin E (3 mM), N-acetylcysteine (50 μM) or vitamin C (200 μM) for 24 hours. Endogenous $H_2O_2$ levels and cell cycle changes were measured as described in FIG. 1C. In addition, cells were transiently transfected with an empty plasmid or an expression plasmid for human catalase and assayed 24 hours later as above. Values from cells transfected with the empty plasmid were subtracted from those obtained from the catalase-containing cells and were expressed as mean±s.e.m. from duplicate dishes.
Figure 1D:
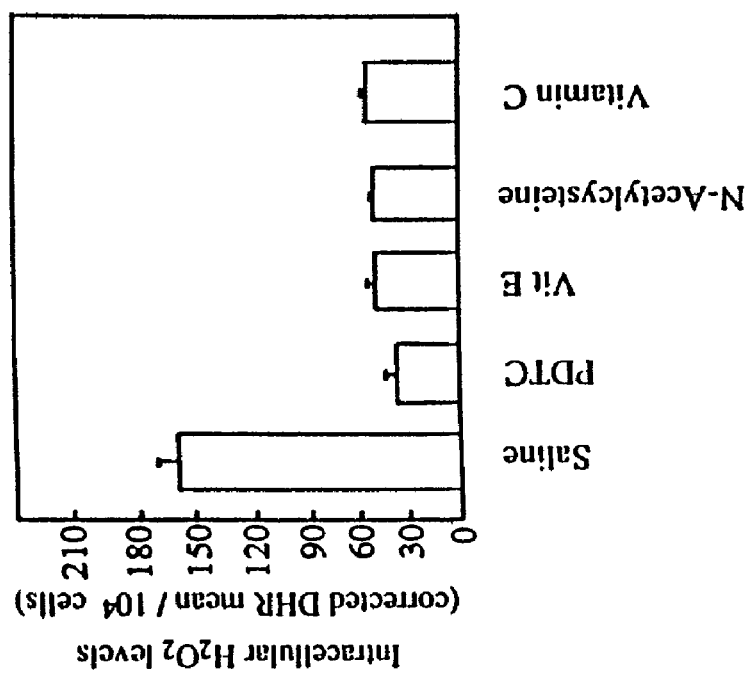

As shown in FIG. 1C, both pyrrolidinedithiocarbamate and vitamin E significantly reduced endogenous $H_2O_2$ levels in both cell lines, with pyrrolidinedithiocarbamate being the more effective reducing agent. Furthermore, this decrease in $H_2O_2$ levels correlated with the induction of $G_1$ cell cycle arrest and the appearance of TUNEL-positive nuclei in these cells. Treatment of HCT 15 cells with the membrane-permeant antioxidant N-acetyl-L-cysteine (NAC) and the dietary antioxidant, vitamin C, showed a similar reduction in $H_2O_2$ levels and the induction of apoptosis (FIG. 1D), supporting a role for reactive oxygen species in cell cycle progression. Since antioxidants may alter the intracellular redox milieu through reactive oxygen species other than $H_2O_2$, HCT 15 cells were transiently transfected with an expression plasmid encoding human catalase. Overexpression of catalase markedly reduced $H_2O_2$ levels and induced cell cycle arrest and apoptosis in these cells, thus directly implicating $H_2O_2$ as an important mediator of the observed cell cycle effects in these antioxidant-treated cells.

To demonstrate further that antioxidants enhance the cytotoxic efficacy of 5-FU and doxorubicin, the $IC_{50}$ value of each drug was determined for HCT 116 and HCT 15 cells grown in soft agar in the presence or absence of 70 µM pyrrolidinedithiocarbamate or 3 mM vitamin E (the approximate $IC_{50}$ values for these compounds in both cell lines). Pyrrolidinedithiocarbamate or vitamin E decreased the $IC_{50}$ for both 5-FU and doxorubicin compared to cells treated with either of the individual drugs alone (FIG. 1E). These effects were more pronounced with pyrrolidinedithiocarbamate, perhaps reflecting its more potent reducing ability. Mechanisms of cellular uptake and metabolism of 5-FU and doxorubicin differ significantly. Thus, it is unlikely that pyrrolidinedithiocarbamate or vitamin E modulate the cytotoxicity of 5-FU or doxorubicin via alterations in these pathways.

Example 13

Figure 2A:
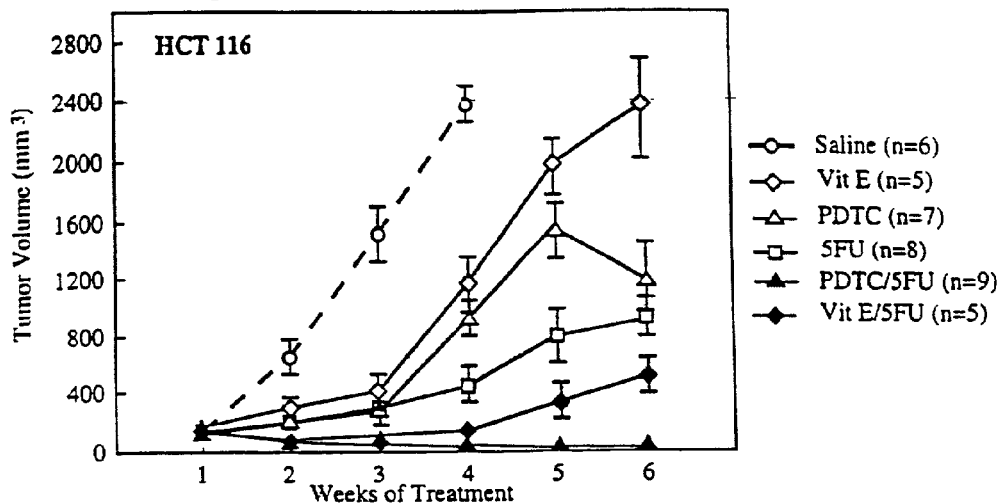
FIG. 2A is a graph and associated photographs of tumor-bearing mice which indicate that pyrrolidinedithiocarbamate and vitamin E enhance 5-FU efficacy in wild type p53 human CRC tumor xenografts. HCT 116 CRC cells were injected subcutaneously between the scapula of nu/nu mice. Once tumors reached approximately 150 mm$^3$, the animals either received weekly i.p. injections of pyrrolidinedithiocarbamate (70 μM) or vitamin E (3 MM), 5-FU (40 mg/kg) or saline, or both an antioxidant and 5-FU. Tumor volume was calculated weekly. The photograph shows the effect of indicated treatments on gross tumor size after 4 weeks of treatment.

The therapeutic efficacy of pyrrolidinedithiocarbamate or vitamin E was next examined in vivo by growing HCT 116 or HCT 15 cells as tumor zenografts in athymic mice. After establishment of palable tumors (mean tumor volume 150 mm3), animals either received weekly i.p. injections of pyrrolidinedithiocarbamate, vitamin E, and/or 5-FU or saline as a negative control. The results with HCT 116 cells are shown in FIG. 2A. After 4 weeks, tumor volumes in control mice necessitated sacrifice in accordance with institutional protocol. Individually, pyrrolidinedithiocarbamate, vitamin E and 5-FU significantly reduced tumor volume over the 6-weeks compared to saline-treated controls. Addition of pyrrolidinedithiocarbamate or vitamin E significantly enhanced the effect of 5-FU. In all nine animals with complete abolishment of tumors, no sign of tumor 25regrowth has been observed following discontinuation of combined treatment for 2 months. Similar results were seen in HCT 15-derived xenografts with the exception that the combination regimens were more effective in these mutant p53 CRC cells.

Figure 2B:
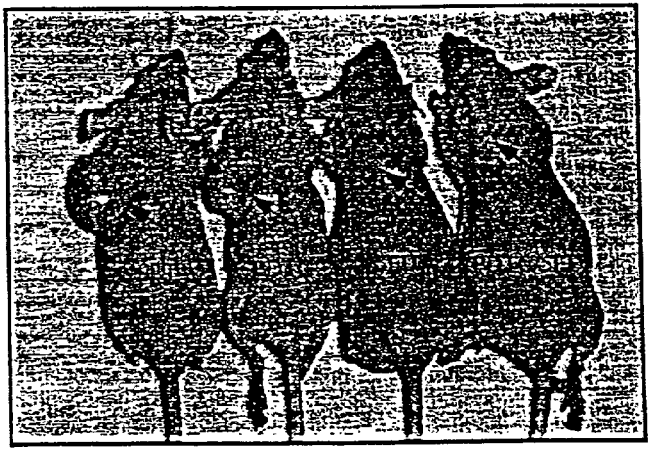
FIG. 2B is a graph of the weeks of treatment with various test materials versus tumor volume (mm$^3$) shows that the enhanced efficacy of pyrrolidinedithiocarbamate and 5-FU as primary treatment and as a salvage regimen for mutant p53 tumors. HCT 15-derived tumors were generated as described above. Animals were then treated with pyrrolidinedithiocarbamate, in the presence or absence of 5-FU, for 3 weeks. At this point, treatments were discontinued in animals receiving the combined treatment of pyrrolidinedithiocarbamate and 5-FU for 2 months. All other treatment groups received both 5-FU and pyrrolidinedithiocarbamate for the remaining 3 weeks.
Figure 2B:
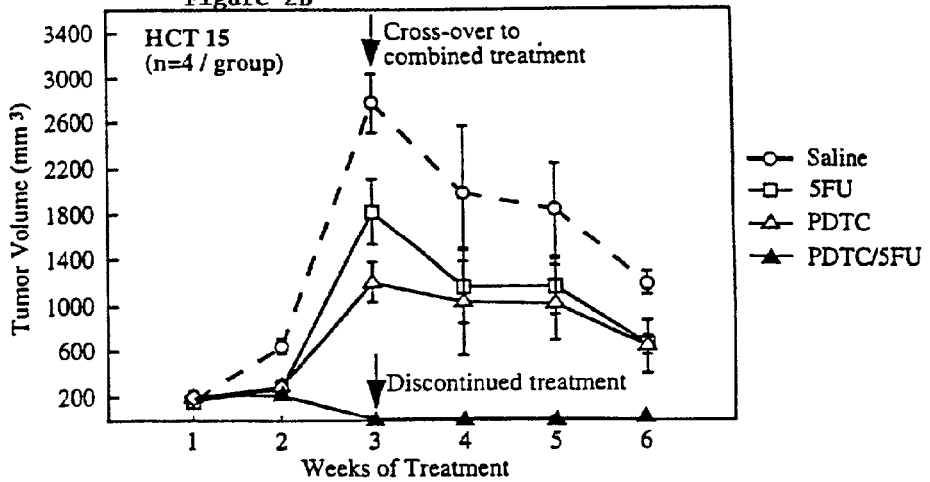

To further explore the in vivo efficacy of pyrrolidinedithiocarbamate and 5-FU in established HCT 15-derived tumors, mice were crossed over to combined treatment once significant differences in single agent therapies were established (FIG. 2B). Mice that initially received no treatment developed large tumors (2780+257 mm$^3$) by 3 weeks. Treatment of these mice with 5-FU and pyrrolidinedithiocarbamate at this time reduced the size of even these advanced lesions (week 6: 1184+96 mm$^3$). Cross-over to combined treatment (5-FU and pyrrolidinedithiocarbamate) also reduced tumor size in mice initially treated with a single agent. Tumors decreased in size from 1864+190 mm$^3$ to 660+82 mm$^3$ and 1325+210 mm$^3$ to 637+231 mm$^3$, for animals treated initially with 5-FU and pyrrolidinedithiocarbamate alone, respectively. These results complement the in vitro findings, and indicate that antioxidants can significantly enhance the efficacy of 5-FU in CRC cells.

No signs of agent-induced toxicity were observed in the mice, as judged by changes in body weight or gross anatomical and microscopic examination of major organs. At necropsy, all tumors exhibit central necrosis grossly, irrespective of tumor size or treatment regimen. Since tumors from mice treated with pyrrolidinedithiocarbamate and 5-FU were no longer present, this treatment group was omitted from these analyses. Immunohistochemical analysis of residual tumors demonstrated a high proliferative index, irrespective of the treatment regimen. However, the apoptotic index increased approximately 5-fold following vitamin E, in both xenograft models (FIG. 2C). In contrast, the apoptotic index of 5-FU-treated tumors was markedly higher in cells expressing wild type p53 (HCT 116) compared to mutant p53 (HCT 15), supporting a role for p53-mediated apoptosis in 5-FU cytotoxicity. Combined vitamin E and 5-FU treatment was able to further increase the apoptotic index in these tumors, even in a mutant p53 genetic background. The apparent synergy between vitamin E and 5-FU-induced apoptosis in mutant p53 HCT 15 cells suggests that antioxidants may re-establish the apoptotic signaling pathway.

Example 14

Regulation of $G_1$ cell cycle arrest and subsequent apoptosis has been attributed to a number of cellular proteins, including p53 and the cyclin-dependent kinase inhibitors, such as $p21^{WAF1/CIP1}$ and p27. Pyrrolidinedithiocarbamate had no effect on p53 or p27 protein levels in either HCT 116 or HCT 15 cells over a 24 hour period, as determined by Western blot analysis (FIG. 3A). In contrast, $p21^{WAF1/CIP1}$ protein and mRNA levels increased within one hour after pyrrolidinedithiocarbamate treatment and persisted for 24 hours (FIG. 1B).

Induction of $p21^{WAF1/CIP1}$ mRNA by pyrrolidinedithiocarbamate appeared to be p53 independent, as the antioxidant effect was not attenuated in HCT 116 cells expressing human papillomavirus (HPV) E6, which inactivates p53 through ubiquitin-mediated protein degradation (FIG. 3B) (Scheffner, et al, *Proc. Natl. Acad. Sci. U.S.A.* 88, 5523 (1991); Crook, et al, *Oncogene* 6, 873 (1991)). Similar increases in p21 WAFI/CIPI expression were observed in HCT 116 and HCT 15 cells treated with vitamin E.

To confirm that the induction of $p21^{WAF1/CIP1}$ by antioxidants was required for these cell cycle disruptions, parental HCT 116 cells or cells were treated with a targeted disruption of $p21^{WAF1/CIP1}$ by pyrrolidinedithiocarbamate or vitamin E for 24 hours (FIG. 3C). In both cells types, there was a significant attenuation of antioxidant-mediated apoptosis, suggesting that $p21^{WAF1/CIP1}$ plays a pivotal role in antioxidant-mediated cell death.

Example 15

To confirm that induction of $p21^{WAF1/CIP1}$ was dependent on the transcriptional activity of antioxidants, HCT 116 and HCT 15 cells were transfected with a 2.4 kilobase pair fragment of the $p21^{WAF1/CIP1}$ promoter linked to a luciferase reporter gene. Treatment of transfected cells with pyrrolidinedithiocarbamate led to an approximate five-fold induction of the $p21^{WAF1/CIP1}$ promoter activity in both HCT 116 and HCT 15 cells, again consistent with a p53-independent induction of $p21^{WAF1/CIP1}$ mRNA and protein (FIG. 4A). Serial deletions of this promoter demonstrated that the pyrrolidinedithiocarbamate responsive element(s) of the $p21^{WAF1/CIP1}$ promoter was located between nucleotide-2078 and -1874. Disruption of this site by site-directed mutagenesis abolished pyrrolidinedithiocarbamate induction of luciferase activity, demonstrating that the NF_IL6 site is required for pyrrolidinedithiocarbamate-induced $p21^{WAF1/CIP1}$ transcription.

The NF_IL6 consensus sequence is recognized by members of the CCAAT/enhancer binding protein (C/EBP) family of transcription factors (S. Akira and T. Kishimoto, *Immunol Rev.* 127, 25 (1992); Landschulz et al., *Genes Dev.* 2 786 (1988); Cao, et al., ibid. 5, 1538 (1991); Chang, et al., *Mol. Cell. Biol.* 10, 6642 (1990); Williams et al., ibid. 5, 1553 (1991); Akira et al., EMBO. J.9, 1897 (1990); Poli, et al., *Cell* 63, 25 643 (1990)). These factors contain a basic DNA-binding region adjacent to a leucine zipper (bZIP) dimerization domain facilitating the formation of homodimers or heterodimers with other bZIP proteins. Interestingly, C/EBPα has been shown to transcriptionally upregulate $p21^{WAF1/CIP1}$ and inhibit cellular proliferation in mouse preadipocytes, although no correlation was shown with apoptosis.

DNA binding activity to the p21$^{WAF1/CIP1}$ NF_IL6 site was increased following pyrrolidinedithiocarbamate treatment, as determined by electrophoretic mobility shift assays (EMSA) performed with a $^{32}$P-labeled oligonucleotide containing the p21$^{WAF1/CIP1}$ NF_IL6 cis element and nuclear extracts from HCT 116 and HCT 15 cells treated over a 24 hour period (FIG. 4B: left panel). Shifted complexes were competed by 50-fold molar excess of an unlabeled oligonucleotide containing a consensus NF$_{-I\,IL}$6 sequence (right panel: lane 2), but not by an oligonucleotide containing a mutated NF_IL6 consensus sequence (lane 3), indicating that the induced complex was specific for the NF_IL6 cis element. Supershift analysis of the induced complex suggested that shifted complexes were due to the interaction of C/EPBβ (lane 5) with the NF_IL6 cis element and not C/EBP≠ (lane 4) or C/EBPδ (lane 6).

To confirm that C/EBPβ could influence p21$^{WAF1/CIP1}$ transcriptional activity, a eukaryotic expression plasmid encoding C/EBPα,β or δ was contransfected into either HCT 116 or HCT 15 cells with the full length p21$^{WAF1/CIP1}$ luciferase promoter construct (FIGS. 4C and 4D). Transfection of C/EBPβ strongly activated p21$^{WAF1/CIP1}$ promoter activity in a dose-dependent manner, and mutation of the NF_IL6 site abolished this stimulation. In contrast, C/EBPα or C/EBPδ failed to stimulate p21 promoter activity.

Finally, the functional role of C/EBPβ was examined in the apoptotic signaling pathway by generating lines of HCT 15 cells that were stably transfected with the human C/EBPβ cDNA, in both the sense and antisense orientation, under the control of an ecdysone inducible promoter. To avoid the possibility that constitutively expressed C/EBPβ might induce cell death, and ecdysone (muristerone A)-inducible expression system (Invitrogen, Carlsbad, Calif.) was used. Human C/EBPβ cDNA was subcloned into pIND at convenient enzyme cleavage ites. Constructs, containing sense and antisense C/EBPβ sequences were verified by double-stranded DNA sequencing. Before transfection, pIND-C/EBPβ constructs were linearized with Pme I and purified. HCT 15 cells were transfected with 5 μg of pVgRXR (Invitrogen) and 10 μg of pIND-C/EBPβ using CELLFECTIN according to manufacture's instructions. After 24 hours, cells were shifted to medium supplemented with 1 mg/ml Geneticin and 10 mg/ml puromycin (GIBCO BRL) to select for transfectant clones. After 2 weeks, antibiotic-resistant cells were subcloned by limiting dilution. The expression of C/EBPβ protein and the subsequent induction of p21$^{WAF1/CIP1}$ was determined following induction with 10 μM muristerone A for 24 hours and Western blot analysis. Three independent positive clones were used for all assays with essentially the same results.

Representative data from clones derived from each of these cell lines is shown in FIGS. 4E and 4F. C/EBPβ overexpression elevated p21$^{WAF1/CIP1}$ protein levels compared to unstimulated basal levels (FIG. 4E: inset). Induction of C/EBPβ also led to an increase in the apoptotic index of these cells in both the presence and absence of antioxidant. In addition, repression of C/EBPβ expression by antisense MRNA induction nearly abolished antioxidant-induced apoptosis in these cells (FIG. 4E). Further evidence that induction of C/EBPβ mediates the effects of antioxidants on colorectal cancer cells was demonstrated by the increased apoptotic index in response to either 5-FU or doxorubicin in the presence of over-expressed C/EBPβ (FIG. 4F). In the absence of C/EBPβ overexpression, 5-FU increased the apoptotic index to 20% whereas doxorubicin did not induce apoptosis. When these cells were induced to overexpress C/EBPβ in the presence of either 5-FU or doxorubicin, apoptosis was increased to 70% and 80%, respectively. Taken together, these data demonstrate that the induction of apoptosis by antioxidants is, at least in part, mediated by a p53-independent induction of p21$^{WAF1/CIP1}$ via activation of the transcription factor C/EBPβ.

Another transcription factor, NF-kB, has been shown to confer resistance to TNFα-mediated apoptosis, although a recent report has shown that induction of NF-kB DNA binding activity in kidney epithelial cells precedes apoptosis following serum-withdrawal. NF-kB activity can be downregulated by pyrrolidinedithiocarbamate through inhibition of the phosphorylation and subsequent proteasome-mediated proteolysis of its inhibitors (IkBs). No reduction in NF-kB DNA binding activity was detected in these CRC cells at the doses of pyrrolidinedithiocarbamate used in these studies. In addition, it has recently been demonstrated that induction of p21$^{WAF1/CIP1}$ can increase NF-kB transcriptional activity, therefore it is unlikely that the antioxidant effect in these cells is mediated by a reduction in NF-kB activity. These studies demonstrate that induction of a transcription factor, C/EBPβ, sensitizes CRC cells to chemotherapeutic agent-mediated apoptosis.

Activation of C/EBPβ, either directly or indirectly, induced p21$^{WAF1/CIP1}$ gene expression, leading to G$_1$ cell cycle arrest and apoptosis in two colorectal cancer cell lines. The ability of the antioxidants pyrrolidinedithiocarbamate and vitamin E to induce this transcription factor, independent of functional p53, has important biological consequences on the efficiency of DNA damaging agents. Both 5-FU and doxorubicin exert their cytotoxic effects mainly through the induction of DNA damage. This damage, through undefined mechanism(s), signals the induction of p53, which, in turn, leads to inhibition of cellular proliferation and apoptosis. Since mutations of p53 occur in over 80% of advanced CRC tumors, these mutations may be responsible for the relatively low response rate of advanced colorectal cancer tumors to DNA-damaging agents, such as 5-FU. Although 5-FU is particularly successful in the treatment of local, wild type p53, colorectal cancer tumors, the success rate falls to 15–20% in patients with advanced, frequently mutant p53-containing colorectal cancer tumors. Thus, the ability of antioxidants (used throughout these studies at doses obtainable in humans) to bypass the requirement of p53-mediated apoptosis demonstrates the utility of combined antioxidants and chemotherapeutic agents for advanced colorectal cancer and other solid tumors.

Example 16

FIGS. 5a and 5b are bar graphs of the BrDU-labeled cells (percent of total cell nuclei) from colorectal cell xenografts derived from athymic mice treated with saline, vitamin E, PDTC, 5-FU, and the combination of vitamin E and 5-FU, as a measure of the effect of the test compound on proliferation of HCT 116 and HCT 15 cells. FIGS. 6a and 6b are bar chart graphs of TUNEL-positive cells (percent of total cell nuclei) also from xenografts derived from athymic mice treated with saline, vitamin E, PDTC, 5-FU, and the combination of vitamin E and 5-FU, as a measure of the effect of the test compound on apoptosis. Tumor tissues were fixed overnight in 4% (v/v) paraformaldehyde and embedded in paraffin according to standard histological procedures. Sections were pretreated with 10 mM citrate buffer (pH 6.0) and incubated with PC10 monoclonal antibody against BrDU (Boehringer Mannheim). TdT labeling of fragmented DNA (TUNEL) was performed according to manufacturer's instructions. The proliferative index (BrDU) and the apoptotic index (TUNEL) were estimated by the precentage of cells scored under a microscope at 200-fold magnification.

Example 17

As indicated in FIG. 7, PDTC treatment induces C/EBPβ DNA binding activity via a post-translational modification. (A) DKO-1 cell were treated with 70 μM PDTC for the indicated times, nuclear extracts were prepared with a [γ-$^{32}$P]-labeled p21-NF_IL6 oligonucleotide (Lanes 1–9). Specificity assays: Lanes 10–12, competition controls were performed on a nuclear extract derived from DKO-1 cells treated with PDTC for 3 h (lane 5), with excess unlabeled wild-type (lane 11) and mutant (lane 12) oligonucleotide. Lanes 13–15, supershift analyses were performed with C/EBPα (lane 13), β (lane 14), or δ (lane 15) polyclonal antibodies. (B) Parallel DKO-1 cell cultures were treated with PDTC (70 μM) for the indicated times. Poly(A) was isolated and treatment-related variations in C/EBPβ mRNA levels were evaluated by Northern blot analysis. IB15 is shown as a control for equivalent loading and transfer. (C) Parallel DKO-1 cultures were treated with PDTC (70 μM) in the presence of [$^{32}$P]orthophosphate. C/EBPβ from cytosolic and nuclear fractions were purified by immunoprecipitation from cells before (time 0) or at the indicated times after PDTC treatment. Treatment-related variations in the localization of C/EBPβ were analyzed by SDS-PAGE followed by autoradiography or Western blot analysis (100 μg of total cellular protein/lane). (D) DKO-1 cells were cultured in the presence of PDTC (70 μM) for 1 hour and then processed for immunocytochemistry to detect treatment-related differences in the compartmentalization of C/EBPβ protein. In all experiments, parallel cultures treated with preimmune sera or primary anti-C/EBPβ antisera that had been preincubated with in vitro translated C/EBPβ protein demonstrated no fluorescent signal after treatment with the secondary Cy3-conjugated antibody. Representative photomicrographs show anti-C/EBPβ stained cells before and after PDTC treatment.

Example 18

FIG. 8 illustrates the effect of PDTC on endogenous cAMP levels and PKA activity. DKO-1 cells were treated with 70 μM PDTC for the indicated times. Cell lysates were prepared and assayed for (A) endogenous cAMP levels or (B) PKA activity (see Experimental Procedures). The values are expressed as pmol mean per μg protein+s.e.m. and are representative of three experiments carried out in quadruplicate.

Example 19

FIG. 9 illustrates that PDTC phosphorylates C/EBPβ at Ser$^{299}$. (A) Endogenous C/EBPβ from [$^{32}$P]orthophosphate-labeled DKO-1 cells (2 mCi/ml. 3 h) that were treated with either 0 μM (lane 1), 70 μM PDTC (lane 2) or 50 μM forskolin were immunoprecipitated with anti C/EBPβ antibodies. Labeled proteins were visualized by SDS-PAGE followed by autoradiography. (B) Tryptic phosphopeptide maps of in vivo labeled epitope-tagged C/EBPβ. Wild type (WT) and mutant (Ala$^{299}$) C/EBPβ, immunoprecipitated from PDTC treated or untreated DKO-1 cells with the antibody to the FLAG-epitope, were digested with trypsin and the phosphopeptides separated by electrophoresis and thin-layer chromatography and visualized by autoradiography, $X_{1,2}$ were constitutively phosphorylated. The level of phosphopeptide $X_3$ was increased after PDTC treatment in cells transfected with the wild type, but not mutant, protein. The circle indicates the origin. (C) Comparison of the in vivo phosphorylation of wild type and Ala substitution mutants of C/EBPβ from untreated cells and cells treated with PDTC. Autoradiography (top) and C/EBPβ immunoblot (bottom) are shown. (D) Phosphorylation of Ser$^{299}$ within C/EBPβ is essential for protein translocation to the nucleus. DKO-1 cells were transfected with pCMV-C/EBPβ (WT) or pCMV-C/EBPβ (Ala$^{299}$), and treated with PDTC for 3 hours. C/EBPβ protein was visualized by immunocytochemistry as described in Experimental Procedures.

Example 20

FIG. 10 illustrates that PKA phosphorylation of C/EBPβ is required for nuclear translocation. (A) Parallel DKO-1 cell cultures were treated with PDTC (0 or 70 μM) for 3 hours. Poly(A)$^+$ mRNA and protein were isolated from each group and treatment-related variations in C/EBPβ mRNA and protein levels were evaluated by Northern or Western blot analysis. IB15 is shown as a control for equivalent loading and transfer. (B) DKO-l cells were treated with PDTC (0 or 70 μM) or PDTC and mPKI (myristylated protein kinase A inhibitor; 1 μM) for 3 hours. Cells were fixed with paraformaldehyde and C/EBPβ protein visualized by immunofluorescence staining. Treatment of cells with mPKI alone failed to induce nuclear translocation of C/EBPβ (data not shown).

Example 21

FIG. 11 illustrates that carboxymethylation of the catalytic subunit of PP2Ac is inhibited by PDTC. DKO-1 cells were incubated in serum-containing media containing [methyl-$^3$H]S-adenosyl methionine and/or 70 μM PDTC for three hours. Cytosolic or nuclear fractions were prepared and C/EBPβ immunoprecipitated using standard methods. Antibody/antigen complexes were resolved by SDS-PAGE and the presence of PP2Ac was detected by fluorography (overnight). PDTC inhibited carboxymethylation of PP2A subunit in nuclear fractions, and to a lesser extent, in cytosolic fractions.

Example 22

FIG. 12 illustrates that PDTC inhibits methyltransferase activation of PP2Ac. PP2A (a and c dimer) was incubated in the presence of [methyl-3H]S-adenosyl methionine, increasing concentrations of PDTC and partially purified rat methyltransferase for thirty minutes at 37 degrees C. The reaction was terminated by the addition of SDS-sample buffer. Samples were resolved by SDS-PAGE and the presence of methylated PP2A catalytic subunit visualized by fluorography. PDTC selectively inhibits the ability of methyltransferase to carboxylate the catalytic subunit of PP2A in a dose dependent manner.

Example 23

To demonstrate a specific and direct inhibitory effect of PDTC on PP2A activity, DKO-1 cells were initially treated with 17 μM PDTC for three hours. Cell lysates were prepared and treated with the following reagents in the presence of phosphorylated C/EBPβ in which the phosphate is radiolabeled, for ten minutes at 37 degrees C: I2 (a selective PP1 inhibitor), okadaic acid (a selective inhibitor of PP2A and PP1), PDTC, I2 and PDTC, and okadaic acid and PDTC. As shown in FIG. 13, PDTC inhibited phosphatase activity in the DKO-1 extract, resulting in maintenance of the C/EBPβ in its phosphorylated state. This effect is reversible following removal of the antioxidant. This result is consistent with PDTC inhibition of the PP2A phosphatase. In contrast, a PP1 phosphastase specific inhibitor, I2, failed to protect C/EBPβ from dephosphorylation under the same conditions. As expected, the nonspecific phosphatase inhibitor okadaic acid inhibited all DKO-1 phosphatase activity, thus protecting the C/EBPβ from dephosphorylation. These results demonstrate that antioxidants such as PDTC are specific inhibitors of a class of phosphatases, such as PP2A, that are involved in the dephosphorylation of C/EBPβ.

Example 24

The effect of PDTC on cellular proliferation or apoptosis was evaluated in a number of normal and cancer cell lines. The $IC_{50}$ was measured as the concentration of PDTC that inhibited cellular proliferation. The results are provided in Table 1. As indicated, PDTC did not inhibit the cell growth of normal cells, but did substantially inhibit the growth of breast carcinoma cells, gastric carcinoma cells, osteosarcoma cells and pancreatic carcinoma cells.

TABLE 1

Effect of PDTC on Cell Proliferation ($IC_{50}$ required to inhibit cellular proliferation or induce apoptosis)

|  | $IC_{50}$ |
|---|---|
| Normal cells | |
| Keratinocytes | 600 μM |
| Primary colonocytes | 500 μM |
| Primary mammary epithelia | 650 μM |
| Non-transformed rat intestinal epithelial cells | 450 μM |
| Breast carcinoma cells | |
| MCF-7 | 13 μM |
| MCF-10WT | 5 μM |
| MCF-10HRas | 5 μM |
| MDA-MB231 | 10 μM |
| MDA MB-468 | 20 μM |
| Gastric carcinoma cells | |
| Hs746T | 35 μM |
| N-87 | 40 μM |
| Osteosarcoma | |
| Saos-2 | 10 μM |
| Pancreatic carcinoma cells | |
| AsPo1 | 70 μM |
| PANC-1 | 75 μM |
| BxPc3 | 100 μM |

Example 25

To evaluate whether antioxidants induce apoptosis in normal cells, normal and cancerous cells were incubated with 70 μM PDTC for 24 hours and DNA fragmentation assessed as a percentage of a control. As indicated in Tables 2 and 3, the normal cell line (primary colonocytes) did not exhibit significant DNA fragmentation after 24 hours of exposure to PDTC, whereas cancerous cells (Wild type p53 HCA-7, HCT 116, mutant p53 HCT 15, DLD-1, and DKO-3 cells) exhibited substantial DNA fragmentation.

TABLE 2

PDTC Induces Apoptosis in CRC Cells but not Normal Cells in vitro (I)

| | DNA Fragmentation after PDTC Treatment (70 μM) (% Control) | | | |
|---|---|---|---|---|
| Cell Type | 3 h | 6 h | 12 h | 24 h |
| Primary Colonocytes | 101 ± 10 | 109 ± 9 | 107 ± 10 | 130 ± 16 |
| Wild Type p53 HCA-7 | 111 ± 13 | 126 ± 17 | 154 ± 19 | 302 ± 35 |
| HCT 116 | 108 ± 11 | 131 ± 21 | 198 ± 23 | 367 ± 49 | bold values: significantly different from untreated cells (P < 0.01), as determined by AOVA

TABLE 3

PDTC Induces Apoptosis in CRC Cells but not Normal Cells in vitro (II)

| | DNA Fragmentation after PDTC Treatment (70 μM) (% Control) | | | |
|---|---|---|---|---|
| Cell Type | 3 h | 6 h | 12 h | 24 h |
| Primary Colonocytes | 101 ± 10 | 109 ± 9 | 107 ± 10 | 130 ± 16 |
| Mutant p53 HCT 15 | 145 ± 12 | 259 ± 18 | 673 ± 34 | 979 ± 34 |
| DLD-1 | 213 ± 17 | 296 ± 21 | 712 ± 34 | 876 ± 46 |
| DKO-3 | 223 ± 11 | 478 ± 16 | 896 ± 23 | 1116 ± 54 | bold values: significantly different from untreated cells (P < 0.01), as determined by AOVA Example 26

As indicated in Tables 4 and 5, PDTC substantially reduces the toxicity of 5-FU in the murine small intestine and the murine colon. These results indicate that PDTC not only increases the cytotoxic effect of antineoplastic agents, it at the same time has a palliative effect on normal cells that are exposed to cytotoxic agents.

Example 27

Isolation of C/EBPβ/PP2A methyltransferase complex

A novel multicomponent complex consisting of C/EBPβ, PP2A and methyltransferase was isolated and initially characterized. This complex appears to play an important role in the regulation of PP2A and downstream transcriptional events including, but not limited to, cell division and apoptosis.

Co-immunoprecipitation techniques demonstrate for the first time that the transcriptional factor C/EBPβ is complexed with the PP2Ac protein phosphatase. This novel complex appears to play an important role mechanistically in the control of the phosphorylation status of C/EBPβ by PP2A.

Additionally, the C/EBPβ/PP2Ac complex has also been shown to consist of the methyltransferase which carboxymethylates the catalytic subunit of C/EBPβ. Rat brain soluble extracts were fractionated by phenyl-Sepharose and analyzed for methyltransferase activity using exogenous PP2A heterodiver (AC complex). The peak of methyltransferase activity was further fractionated by Source Q (strong anion exchange), and gel filtration chromatography. The partially purified methyltransferase in FIG. 14 represents the peak methyltransferase activity from the gel filtration column. This peak fraction of methylase activity is taken further to DEAE (weak anion exchange) and MonoQ (a different strong anion exchange resin) columns. Both C/EBPβ and PP2A are detectable following these additional steps. Rat brain extracts are shown as a positive control (C/EBPβ and PP2Ac migrate at approximately 45 and 36 kDa on SDS-PAGE).

Modifications and variations of the present invention will be obvious to those skilled in the art from the foregoing detailed description. Such modifications and variations are intended to come within the scope of the appended claims.

We claim:

1. A method to enhance the cytotoxicity of an antineoplastic drug for the treatment of a disorder of abnormal cell proliferation, the method comprising administering an effective amount of the antineoplastic drug to a host in need of such treatment in combination with an effective cytotoxicity-increasing amount of an antioxidant, wherein the antioxidant is a mono-ester or di-ester of probucol.

2. The method according to claim 1 wherein the mono-ester or di-ester of probucol is an ester of succinic acid, glutaric acid, adipic acid, suberic acid, sebacic acid, azelaic acid or maleic acid.

3. The method of claim 1, wherein the antineoplastic agent is selected from the group consisting of Aceglatone; Aclarubicin; Altretamine; Aminoglutethimide; 5-Aminogleavulinic Acid; Amsacrine; Anastrozole; Ancitabine Hydrochloride; 17-1A Antibody; Antilymphocyte Immunoglobulins; Antineoplaston A10; Asparaginase; Pegaspargase; Azacitidine; Azathioprine; Batimastat; Benzoporphyrin Derivative; Bicalutamide; Bisantrene Hydrochloride; Bleomycin Sulphate; Brequinar Sodium; Broxuridine; Busulphan; Campath-IH; Caracemide; Carbetimer; Carboplatin; Carboquone; Carmofur; Carmustine; Chlorambucil; Chlorozotocin; Chromomycin; Cisplatin; Cladribine; Corynebacterium parvum; Cyclophosphamide; Cyclosporin; Cytarabine; Dacarbazine; Dactinomycin; Daunorubicin Hydrochloride; Decitabine; Diaziquone; Dichlorodiethylsulphide; Didemnin B.; Docetaxel; Doxifluridine; Doxorubicin Hychloride; Droloxifene; Echinomycin; Edatrexate; Elliptinium; Elmustine; Enloplatin; Enocitabine; Epirubicin Hydrochloride; Estramustine Sodium Phosphate; Etanidazole; Ethoglucid; Etoposide; Fadrozole Hydrochloride; Fazarabine; Fenretinide; Floxuridine; Fludarabine Phosphate; Fluorouracil; Flutamide; Formestane; Fotemustine; Gallium Nitrate; Gencitabine; Gusperimus; Homoharringtonine; Hydroxyurea; Idarubicin Hydrochloride; Ifosfamide; Ilmofosine; Improsulfan Tosylate; Inolimomab; Interleukin-2; Irinotecan; JM-216; Letrozole; Lithium Gamolenate; Lobaplatin; Lomustine; Lonidamine; Mafosfamide; Meiphalan; Menogaril; Mercaptopurine; Methotrexate; Methotrexate Sodium; Miboplatin; Miltefosine; Misonidazole; Mitobronitol; Mitoguazone Dihydrochioride; Mitolactol; Mitomycin; Mitotane; Mitozanetrone Hydrochloride; Mizoribine; Mopidamol; Muitlaichilpeptide; Muromonab-CD3; Mustine Hydrochloride; Mycophenolic Acid; Mycophenolate Mofetil; Nedaplatin; Nilutamide; Nimustine Hydrochloride; Oxaliplatin; Paclitaxel; PCNU; Penostatin; Peplomycin Sulphate; Pipobroman; Pirarubicin; Piritrexim Isethionate; Piroxantrone Hydrochloride; Plicamycin; porfimer Sodium; Prednimustine; Procarbazine Hydrochloride; Raltitrexed; Ranimustine; Razoxane; Rogletimide; Roquinimex; Sebriplatin; Semustine; Sirolimus; Sizofiran; Sobuzoxane; Sodium Bromebrate; Sparfosic Acid; Sparfosate Sodium; Sreptozocin; Sulofenur; Tacrolimus; Tamoxifen; Tegafur; Teloxantrone Hydrochloride; Temozolomide; Teniposide; Testolactone; Tetrasodium Mesotetraphenylporphine-sulphonate; Thioguanine; Thioinosine; Thiotepa; Topotecan; Toremifene; Treosulfan; Trimetrexate; Trofosfamide; Tumor Necrosis Factor; Ubenimex; Uramustine; Vinblastine Sulphate; Vincristine Sulphate; Vindesine Sulphate; Vinorelbine Tartrate; Vorozole; Zinostatin; Zolimomab Aritox; and Zorubicin Hydrochloride.

4. The method of claim 1, wherein the abnormal cell proliferation is a hyperproliferative or preneoplastic lesion.

5. The method according to claim 1, wherein the antineoplastic drug is carboplatin.

6. The method according to claim 1, wherein the antineoplastic drug is cisplatin.

7. The method according to claim 1, wherein the antineoplastic drug is doxorubicin.

8. The method according to claim 1, wherein the antineoplastic drug is daunorubicin.

9. The method according to claim 1, wherein the mono- or di-ester of probucol is the mono-succinic acid ester.

10. The method according to claim 1, wherein the mono- or di-ester of probucol is the mono-glutaric acid ester.

11. The method according to claim 1, wherein the mono- or di-ester of probucol is the mono-adipic acid ester.

12. The method according to claim 1, wherein the mono- or di-ester of probucol is the mono-suberic acid ester.

13. The method according to claim 1, wherein the mono- or di-ester of probucol is the mono-azelaic acid ester.

14. The method according to claim 1, wherein the mono- or di-ester of probucol is the mono-maleic acid ester.

* * * * *